US010155047B2

(12) United States Patent
Satchi-Fainaro et al.

(10) Patent No.: US 10,155,047 B2
(45) Date of Patent: Dec. 18, 2018

(54) POLYMERS HAVING THERAPEUTICALLY ACTIVE AGENTS CONJUGATED THERETO, PROCESSES OF PREPARING SAME AND USES THEREOF

(71) Applicant: Ramot at Tel-Aviv University Ltd., Tel-Aviv (IL)

(72) Inventors: Ronit Satchi-Fainaro, Tel-Aviv (IL); Ela Markovsky, Rehovot (IL); Hemda Baabur-Cohen, Tel-Aviv (IL)

(73) Assignee: Ramot at Tel-Aviv University Ltd., Tel-Aviv (IL)

( * ) Notice: Subject to any disclaimer, the term of this patent is extended or adjusted under 35 U.S.C. 154(b) by 0 days.

(21) Appl. No.: 15/447,257

(22) Filed: Mar. 2, 2017

(65) Prior Publication Data

US 2017/0182176 A1  Jun. 29, 2017

Related U.S. Application Data

(63) Continuation of application No. 14/382,776, filed as application No. PCT/IL2013/050195 on Mar. 5, 2013, now Pat. No. 9,687,562.

(60) Provisional application No. 61/606,557, filed on Mar. 5, 2012.

(51) Int. Cl.
| | |
|---|---|
| A61K 31/337 | (2006.01) |
| A61K 31/704 | (2006.01) |
| A61K 47/48 | (2006.01) |
| A61K 38/48 | (2006.01) |

(52) U.S. Cl.
CPC ...... *A61K 47/48315* (2013.01); *A61K 31/337* (2013.01); *A61K 31/704* (2013.01); *A61K 38/484* (2013.01); *A61K 47/481* (2013.01); *A61K 47/482* (2013.01); *A61K 47/48176* (2013.01); *A61K 47/48246* (2013.01)

(58) Field of Classification Search
None
See application file for complete search history.

(56) References Cited

U.S. PATENT DOCUMENTS

| | | | |
|---|---|---|---|
| 6,803,438 | B1 | 10/2004 | Brocchini et al. |
| 6,884,817 | B2 | 4/2005 | Li et al. |
| 6,949,537 | B2 | 9/2005 | Garlich et al. |
| 7,803,903 | B2 | 9/2010 | Kratz |
| 8,586,019 | B2 | 11/2013 | Satchi-Fainaro et al. |
| 8,658,149 | B2 | 2/2014 | Satchi-Fainaro et al. |
| 2002/0197261 | A1 | 12/2002 | Li et al. |
| 2005/0257114 | A1 | 11/2005 | Gorshe |
| 2005/0287114 | A1 | 12/2005 | Wang et al. |
| 2007/0104719 | A1 | 5/2007 | Carter et al. |
| 2008/0112919 | A1 | 5/2008 | Satchi-Fainaro et al. |
| 2008/0279778 | A1 | 11/2008 | Van et al. |
| 2009/0010887 | A1 | 1/2009 | Ben-Sasson |
| 2010/0022615 | A1 | 1/2010 | Fegley et al. |
| 2011/0135618 | A1 | 6/2011 | Koch et al. |
| 2011/0286923 | A1 | 11/2011 | Satchi-Fainaro et al. |
| 2014/0079638 | A1 | 3/2014 | Satchi-Fainaro et al. |
| 2014/0134111 | A1 | 5/2014 | Satchi-Fainaro et al. |
| 2015/0017115 | A1 | 1/2015 | Satchi-Fainaro et al. |
| 2015/0328330 | A1 | 11/2015 | Satchi-Fainaro et al. |

FOREIGN PATENT DOCUMENTS

| | | |
|---|---|---|
| CN | 101707869 | 5/2010 |
| CN | 102131509 | 7/2011 |
| WO | WO 03/086178 | 10/2003 |
| WO | WO 03/086382 | 10/2003 |
| WO | WO 2004/062588 | 7/2004 |
| WO | WO 2006/012355 | 2/2006 |
| WO | WO 2006/084054 | 8/2006 |
| WO | WO 2007/090094 | 8/2007 |
| WO | WO 2008/034124 | 3/2008 |
| WO | WO 2008/094834 | 8/2008 |
| WO | WO 2008/124735 | 10/2008 |
| WO | WO 2008/141110 | 11/2008 |
| WO | 2009/133545 A2 * | 11/2009 |
| WO | WO 2009/141823 | 11/2009 |
| WO | WO 2009/141826 | 11/2009 |
| WO | WO 2009/141827 | 11/2009 |
| WO | WO 2013/132485 | 9/2013 |

OTHER PUBLICATIONS

Hoes et al. (Journal of Controlled Release, 37-54, 1993).*
Ulbrich et al. (Journal of Drug Targeting, vol. 12(8), 477-489, Sep. 2004).*
Office Action dated May 8, 2017 From The Patent Office of the State Intellectual Property Office of the People's Republic of China Re. Application No. 201380018242.7 and Its Translation Into English. (9 Pages).
Scomparin et al. "Novel Folated and Non-Folated Pullulan Bioconjugates for Anticancer Drug Delivery", European Journal of Pharmaceutical Sciences, 42(5): 547-558, Available Online Mar. 1, 2011.
Communication Pursuant to Article 94(3) EPC Dated Feb. 23, 2017 From the European Patent Office Re. Application No. 09750278.5. (7 Pages).
Communication Pursuant to Article 94(3) EPC Dated Jan. 23, 2017 From the European Patent Office Re. Application No. 09750179.3. (6 Pages).
Communication Pursuant to Article 94(3) EPC Dated Jun. 30, 2015 From the European Patent Office Re. Application No. 09750278.5.
Communication Pursuant to Article 94(3) EPC Dated Nov. 30, 2015 From the European Patent Office Re. Application No. 09750179.3.
Communication Pursuant to Article 94(3) EPC Dated Jan. 31, 2017 From the European Patent Office Re. Application No. 09750275.1. (5 Pages).

(Continued)

*Primary Examiner* — Alma Pipic

(57) ABSTRACT

Polymeric conjugates of a polymeric backbone formed of a plurality of backbone units and having attached to portions of the backbone units two or more therapeutically active agents, or one or more therapeutically active agents and a NCAM targeting moiety, are disclosed. Uses of such polymeric conjugates in treating and/or monitoring cancer and/or medical conditions associated with angiogenesis are also disclosed.

Figure 1A:
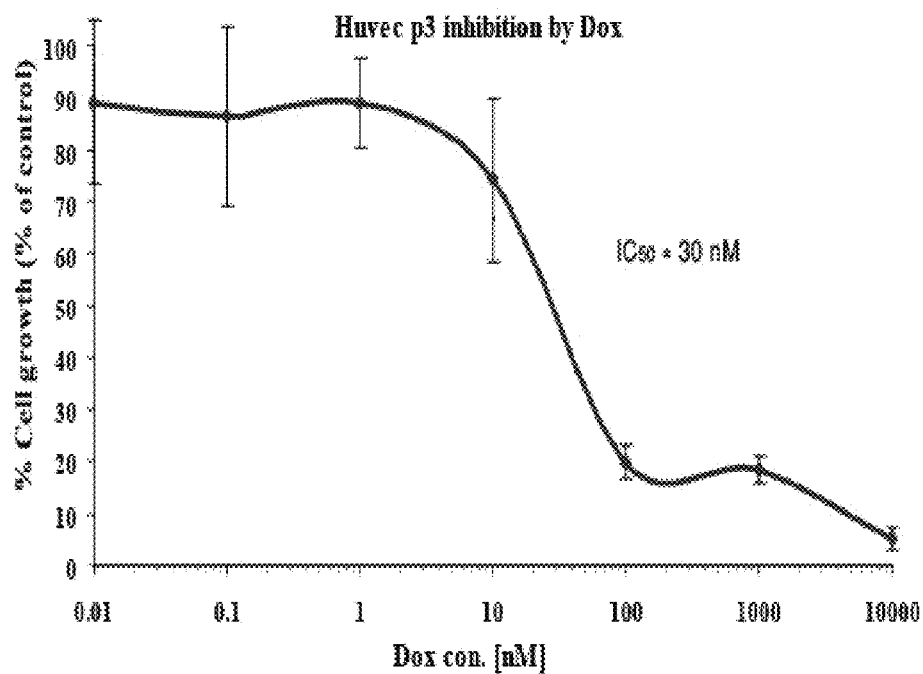

5 Claims, 44 Drawing Sheets
(34 of 44 Drawing Sheet(s) Filed in Color)
Specification includes a Sequence Listing.

(56) References Cited

OTHER PUBLICATIONS

Communication Pursuant to Rule 164(1) EPC [Partial Supplementary European Search Report] Dated Oct. 14, 2015 From the European Patent Office Re. Application No. 13758298.7.
Communication Pursuant to Rule 164(1) EPC and the Supplementary Partial European Search Report Dated Nov. 17, 2014 From the European Patent Office Re. Application No. 09750275.1.
Examination Report dated Dec. 20, 2016 From the Government of India, Patent Office, Intellectual Property Building Re. Application No. 2557/MUMNP/2010. (11 Pages).
Hearing Notice Dated Jun. 17, 2016 From the Government of India, Patent Office, Intellectual Property Building Re. Application No. 2558/MUMNP/2010.
International Preliminary Report on Patentability dated Dec. 2, 2010 From the International Bureau of WIPO Re. Application No. PCT/IL2009/000507.
International Preliminary Report on Patentability dated Dec. 2, 2010 From the International Bureau of WIPO Re. Application No. PCT/IL2009/000510.
International Preliminary Report on Patentability dated Dec. 2, 2010 From the International Bureau of WIPO Re. Application No. PCT/IL2009/000511.
International Preliminary Report on Patentability dated Sep. 18, 2014 From the International Bureau of WIPO Re. Application No. PCT/IL2013/050195.
International Search Report and the Written Opinion dated Dec. 2, 2009 From the International Searching Authority Re. Application No. PCT/IL09/00510.
International Search Report and the Written Opinion dated Nov. 5, 2009 From the International Searching Authority Re. Application No. PCT/IL09/00511.
International Search Report and the Written Opinion dated Jun. 16, 2013 From the International Searching Authority Re. Application No. PCT/IL2013/050195.
International Search Report and the Written Opinion dated Nov. 25, 2009 From the International Searching Authority Re. Application No. PCT/IL09/00507.
Notice of Reexamination dated Feb. 16, 2015 From the Patent Reexamination Board of State Intellectual Property Office of the People's Republic of China Re. Application No. 200980128587.1 and Its Translation Into English.
Notice of Reexamination dated Jul. 29, 2014 From the Patent Reexamination Board of State Intellectual Property Office of the People's Republic of China Re. Application No. 200980128587.1 and Its Translation Into English.
Office Action dated Aug. 16, 2016 From The Patent Office of the State Intellectual Property Office of the People's Republic of China Re. Application No. 201380018242.7 and Its Translation Into English.
Office Action dated Dec. 21, 2015 From The Patent Office of the State Intellectual Property Office of the People's Republic of China Re. Application No. 201380018242.7 and Its Translation Into English.
Official Action dated May 1, 2014 From the US Patent and Trademark Office Re. U.S. Appl. No. 14/158,881.
Official Action dated Mar. 4, 2013 From the US Patent and Trademark Office Re. U.S. Appl. No. 12/993,856.
Official Action dated Oct. 5, 2015 From the US Patent and Trademark Office Re. U.S. Appl. No. 14/816,228.
Official Action dated Apr. 7, 2014 From the US Patent and Trademark Office Re. U.S. Appl. No. 14/082,224.
Official Action dated Nov. 13, 2014 From the US Patent and Trademark Office Re. U.S. Appl. No. 14/082,224.
Official Action dated Dec. 15, 2014 From the US Patent and Trademark Office Re. U.S. Appl. No. 14/158,881.
Official Action dated Apr. 18, 2013 From the US Patent and Trademark Office Re. U.S. Appl. No. 12/993,855.
Official Action dated May 21, 2015 From the US Patent and Trademark Office Re. U.S. Appl. No. 14/082,224.
Official Action dated Aug. 24, 2016 From the US Patent and Trademark Office Re. U.S. Appl. No. 14/382,776.
Official Action dated Jan. 31, 2013 From the US Patent and Trademark Office Re. U.S. Appl. No. 12/993,853.
Reexamination Decision (Decision No. 96781) Dated Sep. 16, 2015 From the Patent Reexamination Board of the State Intellectual Property Office of the People's Republic of China Re. Application No. 200980128587.1 and Its Translation Into English.
Restriction Official Action dated Dec. 3, 2012 From the US Patent and Trademark Office Re. U.S. Appl. No. 12/993,853.
Restriction Official Action dated Feb. 5, 2013 From the US Patent and Trademark Office Re. U.S. Appl. No. 12/993,855.
Restriction Official Action dated Oct. 11, 2012 From the US Patent and Trademark Office Re. U.S. Appl. No. 12/993,856.
Restriction Official Action dated Jun. 23, 2014 From the US Patent and Trademark Office Re. U.S. Appl. No. 14/242,901.
Supplementary European Search Report and the European Search Opinion dated Mar. 10, 2016 From the European Patent Office Re. Application No. 13758298.7.
Supplementary European Search Report and the European Search Opinion dated Sep. 10, 2014 From the European Patent Office Re. Application No. 09750179.3.
Supplementary European Search Report and the European Search Opinion dated Mar. 19, 2015 From the European Patent Office Re. Application No. 09750275.1.
Supplementary European Search Report and the European Search Opinion dated Jul. 21, 2014 From the European Patent Office Re. Application No. 09750278.5.
Translation of Decision on Rejection dated Mar. 12, 2013 From the State Intellectual Property Office of the People's Republic of China Re. Application No. 200980128587.1.
Translation of Office Action dated Aug. 1, 2012 From the State Intellectual Property Office of the People's Republic of China Re. Application No. 200980128587.1.
Translation of Office Action dated Jan. 5, 2012 From the State Intellectual Property Office of the People's Republic of China Re. Application No. 200980128588.6.
Translation of Office Action dated Sep. 26, 2011 From the State Intellectual Property Office of the People's Republic of China Re. Application No. 200980128587.1.
Alavi et al. "Chemoresistance of Endothelial Cells Induced by Basic Fibroblast Growth Factor Depends on Raf-1-Mediated Inhibition of the Proapoptotic Kinase, ASK1", Cancer Research, XP055136030, 67(6): 2766-2772, Mar. 15, 2007. Abstract, Fig.2C.
Baabur-Cohen et al. "Recent Progress in Polymer Therapeutics as Nanomedicines", Handbook of Harnessing Biomaterials in Nanomedicine: Preparation, Toxicity, and Applications, Chap.4: 77-122, 2012.
Baltali et al. "Paclitaxel and Doxorubicin Combination in the First-Line Treatment of Metastatic Breast Cancer", Tumori, 88(3): 200-203, 2002.
Chen et al. "Synthesis and Biological Evaluation of Dimeric RGD Peptide-Paclitaxel Conjugate as A Model for Integrin-Targeted Drug Delivery", Journal of Medicinal Chemistry, 48: 1098-1106, 2005. p. 1098, r-h col., Para Full 1 of the col., Fig.1.
Cheng et al. "Combination Chemotherapy of Doxorubicin and Paclitaxel for Hepatocellular Carcinoma in Vitro and in Vivo", Journal of Cancer Research and Clinical Oncology 136(2): 267-274, Feb. 1, 2010.
Duncan "Polymer Conjugates as Anticancer Nanomedicines", Nature Reviews Cancer, XP055216015, 6(9): 688-701, Sep. 2006.
Duncan et al. "Polymer-Drug Conjugates, PDEPT and PELT: Basic Principles for Design and Transfer From the Laboratory to Clinic", Journal of Controlled Release, XP027296078, 74(1-3): 135-146, Jul. 6, 2001.
Eldar-Boock et al. "Integrin-Assisted Drug Delivery of Nano-Scaled Polymer Therapeutics Bearing Paclitaxel", Biomaterials, XP028369082, 32(15): 3862-3874, May 2011.
Greco et al. "Combination Therapy: Opportunities and Challenges for Polymer-Drug Conjugates as Anticancer Nanomedicines", Advanced Drug Delivery Reviews, 61: 1203-1213, 2009.

(56) References Cited

OTHER PUBLICATIONS

Hruby et al. "Hydroxybisphosphonate-Containing Polymeric Drug-Delivery Systems Designed for Targeting Into Bone Tissue", Journal of Applied Polymer Science, XP008076287, 101(5): 3192-3201, Jan. 1, 2006. Abstract, p. 3193, col. 2, Last Line, p. 3200, col. 2, First Line.

Jensen et al. "Targeting the Neural Cell Adhesion Molecule in Cancer", Cancer Letters, XP022310543, 258(1): 9-21, Oct. 18, 2007.

Lee et al. "Anthracycline Chemotherapy Inhibits HIF-1 Transcriptional Activity and Tumor-Induced Mobilization of Circulating Angiogenic Cells", Proc. Natl. Acad. Sci, USA, PNAS, XP055135983, 106(7): 2353-2358, Feb. 17, 2009. Abstract.

Marsili et al. "Interaction of DDSDEEN Peptide With N-CAM Protein. Possible Mechanism Enhancing Neuronal Differentiation", Peptides, 29: 2232-2242, 2008.

Meerum Terwogt et al. "Phase I Clinical and Pharmacokinetic Study of PNU166945, A Novel Water-Soluble Polymer-Conjugated Prodrug of Paclitaxel", Anti-Cancer Drug, XP008124180, 12(4): 315-323, Apr. 1, 2001. Fig.1.

Miller et al. "A Novel Bi-Specific Targeting Agent Based on A Polymer-Alendronate-Taxane Conjugate to Target Metastatic Prostate Carcinomas", Proceedings of the American Association for Cancer Research Annual Meeting, XP009179745, 49: 84-85, # 369, Apr. 2008. & 99th Annual Meeting of the American Association for Cancer Research, AACR, San Diego, CA, USA, Apr. 12-16, 2008. Title, Abstract.

Miller et al. "Targeting Bone Metastases With A Bispecific Anticancer and Antiangiogenic Polymer-Alensronate-Taxane Conjugate", Angewandte Chemie International Edition, XP002680271, 48(16): 2949-2954, Apr. 6, 2009. 'HPMA-Alendronate-TNP470 Conjugate, for Treating Bone Cancer', Title, p. 2949, First Line of col. 2, p. 2949, Last 5 Lines, p. 2950, First Line.

Mitra et al. "Comparison of Polymeric Conjugates of Mono- and Bi-Cyclic RGD Peptide for Targeting Tumor Angiogenesis", 2006 National Biotechnology Conference, The AAPS Journal, 8(S1): # 127, 2006. § 1, 3-4.

Mitra et al. "Polymeric Conjugates of Mono- and Bi-Cyclic AlphaVBeta3 Binding Peptides for Tumor Targeting", Journal of Controlled Release, 114: 175-183, 2006.

Mitra et al. "Polymer-Peptide Conjugates for Angiogenesis Targeted Tumor Radiotherapy", Nuclear Medicine and Biology, 33: 43-52, 2006.

O'Hare et al. "Polymeric Drug-Carriers Containing Doxorubicin and Melanocyte-Stimulating Hormone: In Vitro and In Vivo Evaluation Against Murine Melanoma", Journal of Drug Targeting, 1: 217-229, 1993.

Pan et al. "Backbone Degradable Multiblock N-(2-Hydroxypropyl)Methacrylamide Copolymer Conjugates Via Reversible Addition Fragmentation Chain Transfer Polymerization and Thiol-Ene Coupling Reaction", Biomacromolecules, 12(1): 247-252, Jan. 10, 2011.

Pan et al. "Water-Soluble HPMA Copolymer—Prostaglandin E1, Conjugates Conatining A Cathepsin K Sensitive Spacer", Journal of Drug Targeting, XP008140389, 14(6): 425-435, 2006. Abstract.

Rihova et al. "Clinical Implications of N-(2-Hydroxypropyl)Methacrylamide Copolymers", Current Pharmaceutical Biotechnology, XP008124188, 4(5): 311-322, Oct. 1, 2003. p. 313, col. 1, Penultimate, p. 314, col. 1 Last Line, p. 316, Fig.4.

Satchi-Fainaro et al. "Synthesis and Characterization of A Catalytic Antibody-HPMA Copolymer-Conjugate as A Tool for Tumor Selective Prodrug Activation", Bioorganic & Medicinal Chemistry, 10(9): 3023-3029, 2002.

Satchi-Fainaro et al. "Targeting Angiogenesis With A Conjugate of HPMA Copolymer and TNP-470", Nature Medicine, XP002542562, 10(3): 255-261, Mar. 2004. 'HPMA—TNP470 Conjugates', Abstract.

Segal et al. "Design and Development of Polymer Conjugates as Anti-Angiogenic Agents", Advanced Drug Delivery Reviews, XP026698380, 61(13): 1159-1176, Nov. 12, 2009. Sections 3, 4, p. 1164-1168.

Segal et al. "Enhanced Anti-Tumor Activity and Safety Profile of Targeted Nano-Scaled HPMA Copolymer-Alendronate-TNP-470 Conjugate in the Treatment of Bone Malignances", Biomaterials, 32(19): 4450-4463, Jul. 2011.

Segal et al. "Synthesis and Characterization of A Novel Combined Targeted Anticancer and Antiangiogenic Polymer Therapeutics", Proceedings of the American Association for Cancer Research Annual Meeting, San Diego, CA, USA, Apr. 12-16, 2008, XP055335479, 68(9/Suppl.): # 1102, May 1, 2008.

Segal et al. "Targeting Angiogenesis-Dependent Calcified Neoplasms Using Combines Polymer Therapeutics", PLoS ONE, XP002727812, 4(4): e5233-1-e5233-16, Apr. 21, 2009. Abstract, p. e5233, col. 2, First Full Para, Supporting Info.

Seymour et al. "Hepatic Drug Targeting: Phase I Evaluation of Polymer-Bound Doxorubicin", Journal of Clinical Oncology, 20(6): 1668-1676, Mar. 15, 2002.

Sledge et al. "Phase III Trial of Doxorubicin, Paclitaxel, and the Combination of Doxorubicin and Paclitaxel as Front-Line Chemotherapy for Metastatic Breast Cancer: An Intergroup Trial (E1193)", Journal of Clinical Oncology, 21(4): 588-592, Feb. 15, 2003.

Uludag "Bisphosphonates as A Foundation of Drug Delivery to Bone", Current Pharmaceutical Design, 8: 1929-1944, 2002.

Van Hagen et al. "Evaluation of A Radiolabelled Cyclic DTPA-RGD Analogue for Tumour Imaging and Radionuclide Therapy", International Journal of Cancer, 90(4): 186-198, Aug. 2000.

Wan et al. "Targeting Endothelial Cell Using HPMA Copolymer-Doxorubicin-RGD Conjugates", Proceedings of the 30th Annual Meeting of the International Symposium on Controlled Release Bioactive Materials, XP009178957, 30: 491-492, #491, Jan. 1, 2003.

Wang et al. "Paclitaxel at Ultra Low Concentrations Inhibits Angiogenesis Without Affecting Cellular Microtube Assembly", Anti-Cancer Drugs, 14: 13-19, 2003.

Wang et al. "Synthesis and Evaluation of Water-Soluble Polymeric Bont-Targeted Drug Delivery Systems", Bioconjugate Chemistry, XP002290582, 14: 853-859, Jan. 2003. 'Polymer—Fluorescein—Alendronate Conjugate', Abstract, Last Line of Conclusion.

Zhang "Poly (L-Glutamic Acid)-Paclitaxel Conjugates for Cancer Treatment", Biomedical Science, Engineering and Technology, XP055216033, Chap.24: 587-603, Jan. 20, 2012. Compounds PG-PTX.

Communication Pursuant to Article 94(3) EPC Dated Mar. 6, 2018 From the European Patent Office Re. Application No. 13758298.7. (7 Pages).

Etrych et al. "Conjugates of Doxorubicin With Graft HPMA Copolymers for Passive Tumor Targeting", Journal of Controlled Release, XP025714817, 132(3): 184-192, Available Online Apr. 29, 2008.

Etrych et al. "N-(2-Hydroxypropyl)Methacrylamide-Based Polymer Conjugates With pH-Controlled Activation of Doxorubicin. I. New Synthesis, Physicochemical Characterization and Preliminary Biological Evaluation", Journal of Applied Polymer Science, XP055455188, 109(5): 3050-3061, Published Online May 20, 2008.

Etrych et al. "Synthesis of HPMA Copolymers Containing Doxorubicin Bound Via A Hydrazone Linkage. Effect of Spacer on Drug Release and In Vitro Cytotoxicity", Macromolecular Bioscience, XP008076237, 2(1): 43-52, Jan. 2002.

Grange et al. "Combined Delivery and Magnetic Resonance Imaging of Neural Cell Adhesion Molecule-Targeted Doxorubicin-Containing Liposomes in Experimentally Induced Kaposi's Sarcoma", Cancer Research, XP055072022, 70(6): 2180-2190, Published Online Mar. 9, 2010.

\* cited by examiner

Isobolograms at IC40,60,80 of PTX-DOX Combinations HeLa

FIG. 7A
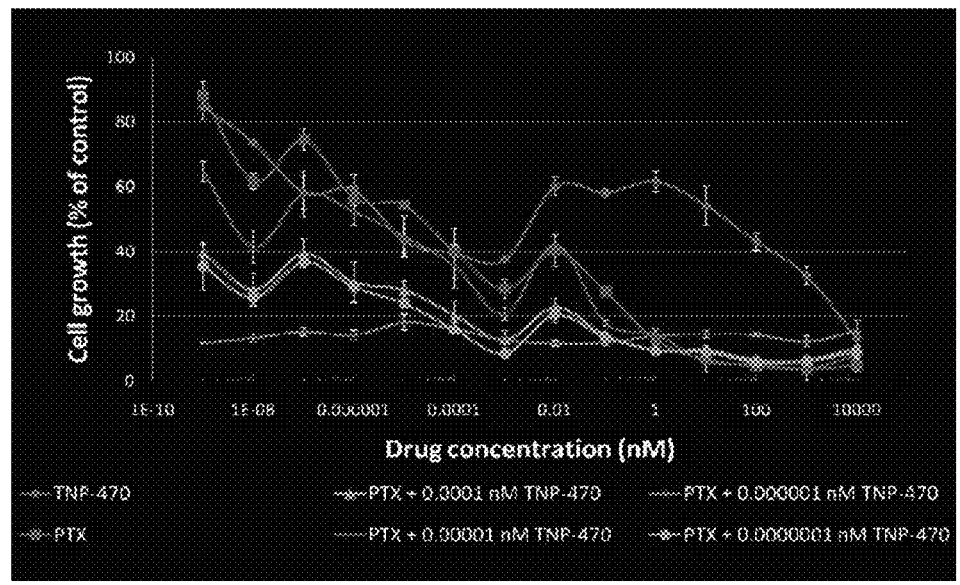
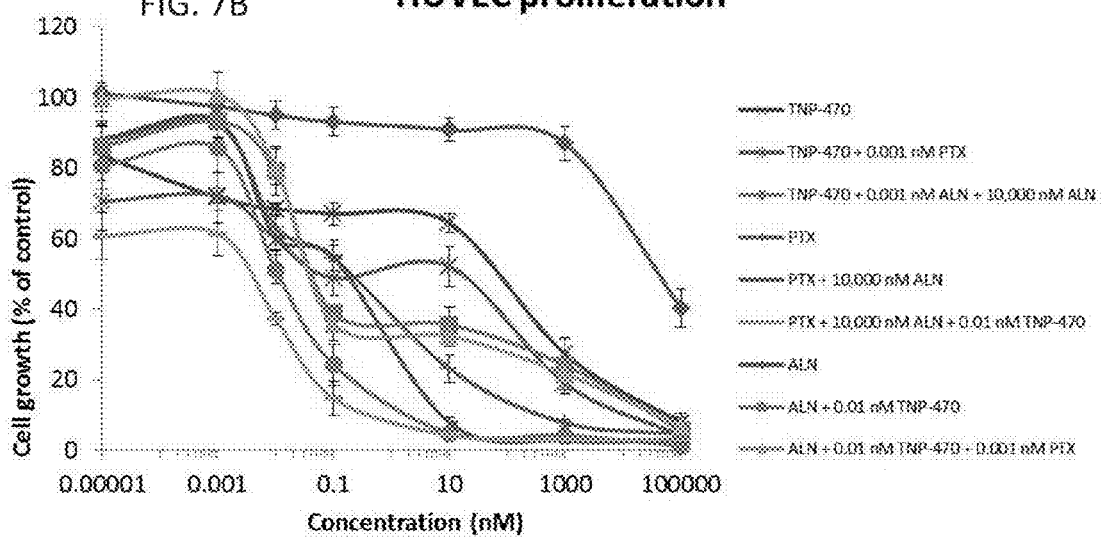

Methacryloyl chloride    Glycine-OH                    MA-Gly-OH

Boc-FK-PABC-PTX

FK-PABC-PTX    MA-GFLG-NHS    → MA-GFLG-FK-PABC-PTX

PGA-PTX-DOX

FIG. 23A
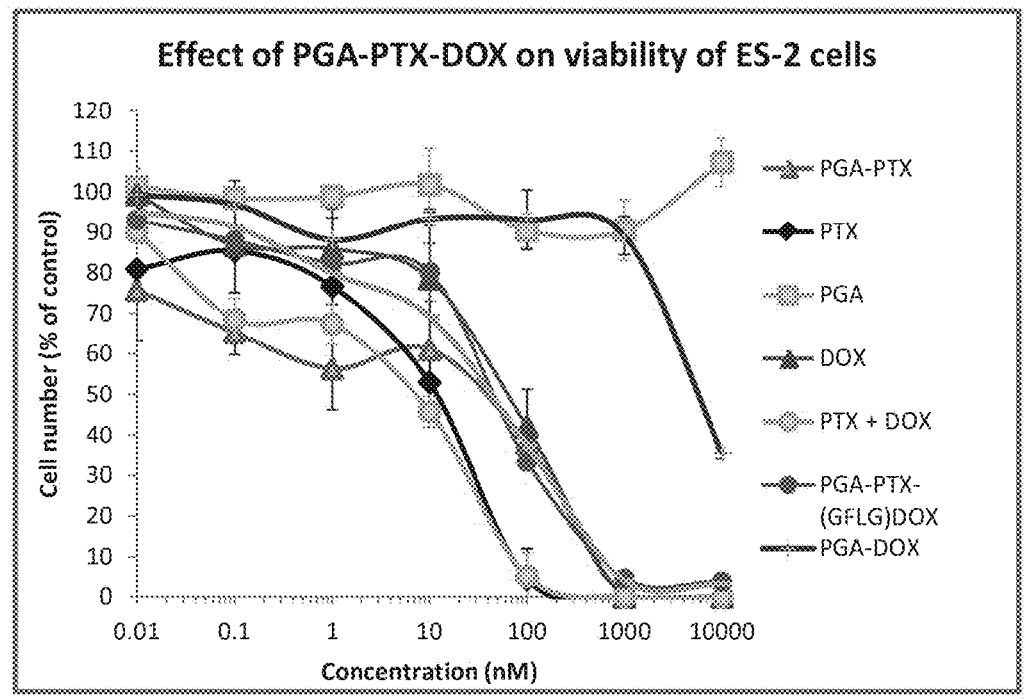
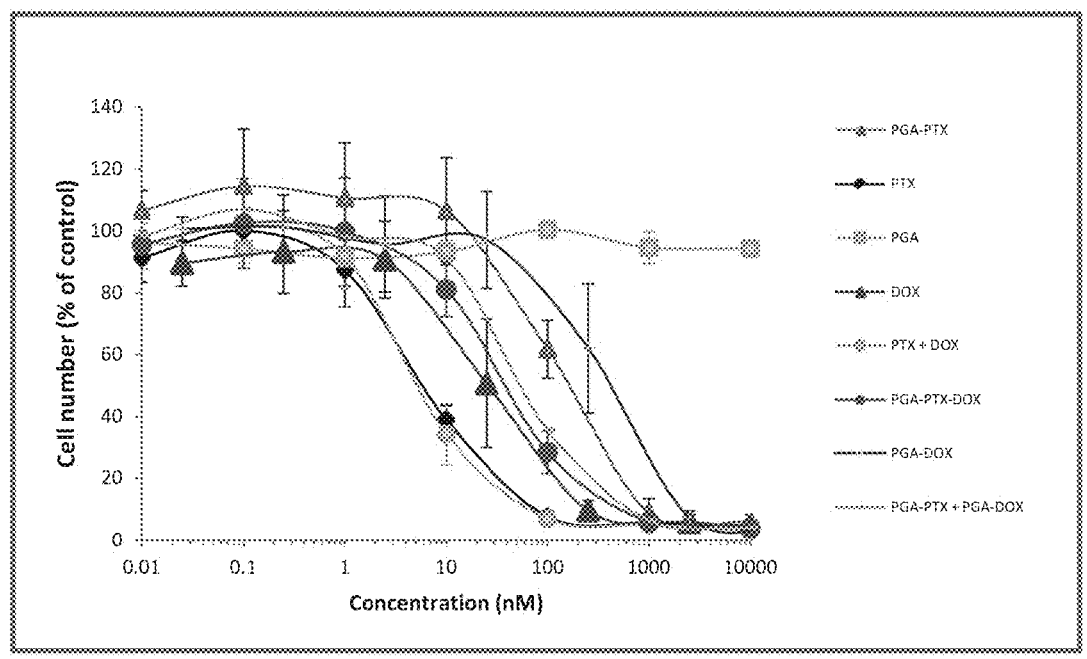
FIG. 23B

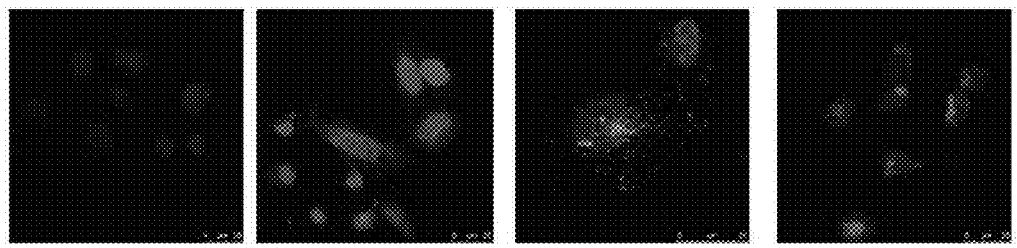
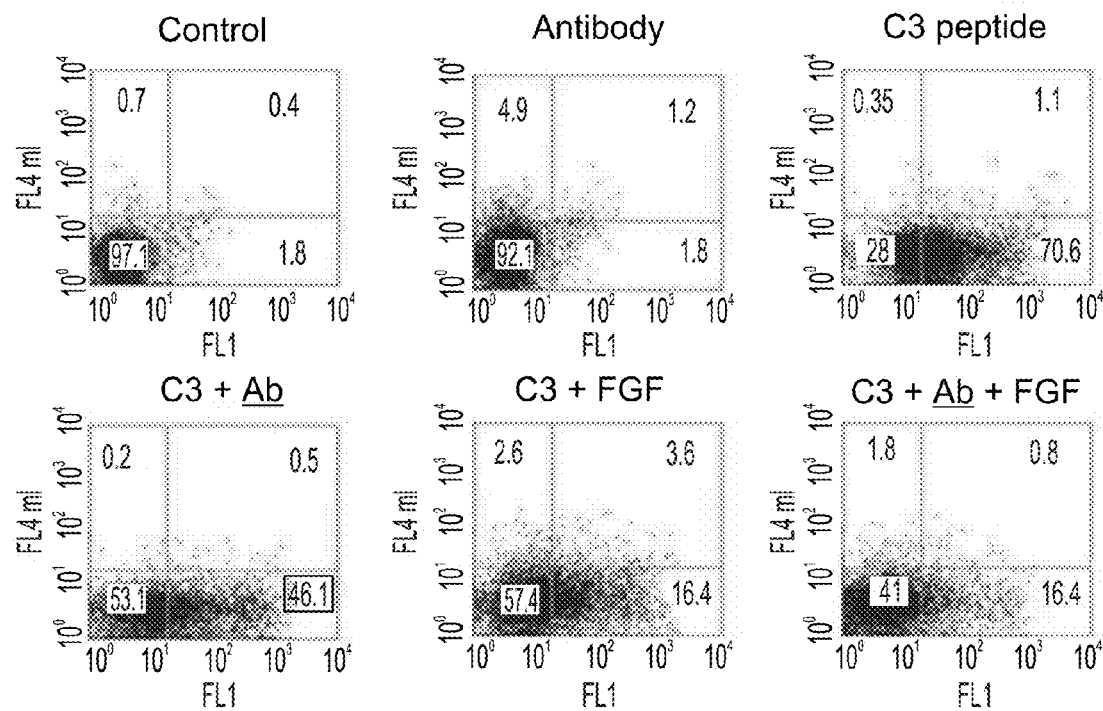

SEQUENCE LISTING

<160> NUMBER OF SEQ ID NOS: 30

<210> SEQ ID NO 1
<211> LENGTH: 8
<212> TYPE: PRT
<213> ORGANISM: Artificial sequence
<220> FEATURE:
<223> OTHER INFORMATION: Synthetic peptide

<400> SEQUENCE: 1

Gly Asp Asp Ser Asp Glu Glu Asn
1               5

<210> SEQ ID NO 2
<211> LENGTH: 8
<212> TYPE: PRT
<213> ORGANISM: Artificial sequence
<220> FEATURE:
<223> OTHER INFORMATION: Synthetic peptide

<400> SEQUENCE: 2

Gly Glu Ser Asp Asp Glu Asn Asp
1               5

<210> SEQ ID NO 3
<211> LENGTH: 12
<212> TYPE: PRT
<213> ORGANISM: Artificial sequence
<220> FEATURE:
<223> OTHER INFORMATION: Synthetic peptide

<400> SEQUENCE: 3

Gly Ala Ser Lys Lys Pro Lys Arg Asn Ile Lys Ala
1               5                   10

<210> SEQ ID NO 4
<211> LENGTH: 12
<212> TYPE: PRT
<213> ORGANISM: Artificial sequence
<220> FEATURE:
<223> OTHER INFORMATION: Synthetic peptide

<400> SEQUENCE: 4

Gly Ala Ser Lys Lys Pro Ala Ala Asn Ile Lys Ala
1               5                   10

<210> SEQ ID NO 5
<211> LENGTH: 7
<212> TYPE: PRT
<213> ORGANISM: Artificial sequence
<220> FEATURE:
<223> OTHER INFORMATION: Synthetic peptide

<400> SEQUENCE: 5

Asp Asp Ser Asp Glu Glu Asn
1               5

<210> SEQ ID NO 6
<211> LENGTH: 11
<212> TYPE: PRT
<213> ORGANISM: Artificial sequence
<220> FEATURE:
<223> OTHER INFORMATION: Synthetic peptide

<400> SEQUENCE: 6

Ala Ser Lys Lys Pro Lys Arg Asn Ile Lys Ala
1               5                   10

```
<210> SEQ ID NO 7
<211> LENGTH: 3
<212> TYPE: PRT
<213> ORGANISM: Artificial sequence
<220> FEATURE:
<223> OTHER INFORMATION: Synthetic peptide

<400> SEQUENCE: 7

Arg Gly Asp
1

<210> SEQ ID NO 8
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<223> OTHER INFORMATION: A cyclic peptide
<220> FEATURE:
<221> NAME/KEY: misc_feature
<222> LOCATION: (4)..(5)
<223> OTHER INFORMATION: D stereo isomer

<400> SEQUENCE: 8

Arg Gly Asp Phe Lys
1               5

<210> SEQ ID NO 9
<211> LENGTH: 11
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (2)..(10)
<223> OTHER INFORMATION: Disulfide bridge
<220> FEATURE:
<221> NAME/KEY: misc_feature
<222> LOCATION: (4)..(8)
<223> OTHER INFORMATION: Disulfide bridge

<400> SEQUENCE: 9

Ala Cys Asp Cys Arg Gly Asp Cys Phe Cys Gly
1               5                   10

<210> SEQ ID NO 10
<211> LENGTH: 11
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (2)..(6)
<223> OTHER INFORMATION: Cyclic peptide
<220> FEATURE:
<221> NAME/KEY: misc_feature
<222> LOCATION: (5)..(5)
<223> OTHER INFORMATION: D stereo isomer
<220> FEATURE:
<221> NAME/KEY: misc_feature
<222> LOCATION: (7)..(11)
<223> OTHER INFORMATION: Cyclic peptide
<220> FEATURE:
<221> NAME/KEY: misc_feature
<222> LOCATION: (10)..(10)
<223> OTHER INFORMATION: D stereo isomer
```

```
<400> SEQUENCE: 10

Glu Arg Gly Asp Phe Lys Arg Gly Asp Phe Lys
1               5                   10

<210> SEQ ID NO 11
<211> LENGTH: 2
<212> TYPE: PRT
<213> ORGANISM: Artificial sequence
<220> FEATURE:
<223> OTHER INFORMATION: An example of a linker having cathepsin-B
      cleavable site
<220> FEATURE:
<221> NAME/KEY: misc_feature
<222> LOCATION: (1)..(1)
<223> OTHER INFORMATION: Citrulline

<400> SEQUENCE: 11

Xaa Val
1

<210> SEQ ID NO 12
<211> LENGTH: 2
<212> TYPE: PRT
<213> ORGANISM: Artificial sequence
<220> FEATURE:
<223> OTHER INFORMATION: An example of a linker having cathepsin-B
      cleavable site

<400> SEQUENCE: 12

Phe Lys
1

<210> SEQ ID NO 13
<211> LENGTH: 2
<212> TYPE: PRT
<213> ORGANISM: Artificial sequence
<220> FEATURE:
<223> OTHER INFORMATION: An example of a linker having cathepsin-B
      cleavable site

<400> SEQUENCE: 13

Val Arg
1

<210> SEQ ID NO 14
<211> LENGTH: 2
<212> TYPE: PRT
<213> ORGANISM: Artificial sequence
<220> FEATURE:
<223> OTHER INFORMATION: An example of a linker having cathepsin-B
      cleavable site

<400> SEQUENCE: 14

Phe Arg
1

<210> SEQ ID NO 15
<211> LENGTH: 4
<212> TYPE: PRT
<213> ORGANISM: Artificial sequence
<220> FEATURE:
<223> OTHER INFORMATION: An example of a linker having cathepsin-B
      cleavable site

<400> SEQUENCE: 15

Gly Phe Leu Gly
1
```

```
<210> SEQ ID NO 16
<211> LENGTH: 4
<212> TYPE: PRT
<213> ORGANISM: Artificial sequence
<220> FEATURE:
<223> OTHER INFORMATION: An example of a linker having cathepsin-B
      cleavable site

<400> SEQUENCE: 16

Gly Phe Ala Leu
1

<210> SEQ ID NO 17
<211> LENGTH: 4
<212> TYPE: PRT
<213> ORGANISM: Artificial sequence
<220> FEATURE:
<223> OTHER INFORMATION: An example of a linker having cathepsin-B
      cleavable site

<400> SEQUENCE: 17

Ala Leu Ala Leu
1

<210> SEQ ID NO 18
<211> LENGTH: 3
<212> TYPE: PRT
<213> ORGANISM: Artificial sequence
<220> FEATURE:
<223> OTHER INFORMATION: An example of a linker having cathepsin-B
      cleavable site

<400> SEQUENCE: 18

Gly Leu Gly
1

<210> SEQ ID NO 19
<211> LENGTH: 3
<212> TYPE: PRT
<213> ORGANISM: Artificial sequence
<220> FEATURE:
<223> OTHER INFORMATION: An example of a linker having cathepsin-B
      cleavable site

<400> SEQUENCE: 19

Gly Phe Gly
1

<210> SEQ ID NO 20
<211> LENGTH: 6
<212> TYPE: PRT
<213> ORGANISM: Artificial sequence
<220> FEATURE:
<223> OTHER INFORMATION: An example of a linker having cathepsin-B
      cleavable site

<400> SEQUENCE: 20

Gly Phe Leu Gly Phe Lys
1               5

<210> SEQ ID NO 21
<211> LENGTH: 1
<212> TYPE: PRT
<213> ORGANISM: Artificial sequence
<220> FEATURE:
<223> OTHER INFORMATION: An example of a linker having cathepsin-B
      cleavable site
```

```
<400> SEQUENCE: 21

Arg
1

<210> SEQ ID NO 22
<211> LENGTH: 2
<212> TYPE: PRT
<213> ORGANISM: Artificial sequence
<220> FEATURE:
<223> OTHER INFORMATION: An example of a linker having cathepsin-B
      cleavable site

<400> SEQUENCE: 22

Arg Arg
1

<210> SEQ ID NO 23
<211> LENGTH: 14
<212> TYPE: PRT
<213> ORGANISM: Artificial sequence
<220> FEATURE:
<223> OTHER INFORMATION: An example of a linker having cathepsin-B
      cleavable site

<400> SEQUENCE: 23

Glu Glu Glu Glu Glu Glu Asp Asp Asp Asp Asp Asp Asp
1               5                   10

<210> SEQ ID NO 24
<211> LENGTH: 4
<212> TYPE: PRT
<213> ORGANISM: Artificial sequence
<220> FEATURE:
<223> OTHER INFORMATION: A non-limiting example of a linker having
      cathepsin K cleavable site
<220> FEATURE:
<221> NAME/KEY: misc_feature
<222> LOCATION: (4)..(4)
<223> OTHER INFORMATION: Norleucine

<400> SEQUENCE: 24

Gly Gly Pro Xaa
1

<210> SEQ ID NO 25
<211> LENGTH: 3
<212> TYPE: PRT
<213> ORGANISM: Artificial sequence
<220> FEATURE:
<223> OTHER INFORMATION: Example of a linker

<400> SEQUENCE: 25

Gly Leu Gly
1

<210> SEQ ID NO 26
<211> LENGTH: 3
<212> TYPE: PRT
<213> ORGANISM: Artificial sequence
<220> FEATURE:
<223> OTHER INFORMATION: Example of a linker

<400> SEQUENCE: 26

Gly Phe Gly
1

<210> SEQ ID NO 27
```

```
<211> LENGTH: 4
<212> TYPE: PRT
<213> ORGANISM: Artificial sequence
<220> FEATURE:
<223> OTHER INFORMATION: Example of a linker

<400> SEQUENCE: 27

Gly Leu Phe Gly
1

<210> SEQ ID NO 28
<211> LENGTH: 4
<212> TYPE: PRT
<213> ORGANISM: Artificial sequence
<220> FEATURE:
<223> OTHER INFORMATION: Example of a linker

<400> SEQUENCE: 28

Gly Phe Leu Gly
1

<210> SEQ ID NO 29
<211> LENGTH: 2
<212> TYPE: PRT
<213> ORGANISM: Artificial sequence
<220> FEATURE:
<223> OTHER INFORMATION: Example of a linker

<400> SEQUENCE: 29

Phe Lys
1

<210> SEQ ID NO 30
<211> LENGTH: 6
<212> TYPE: PRT
<213> ORGANISM: Artificial sequence
<220> FEATURE:
<223> OTHER INFORMATION: Example of a linker

<400> SEQUENCE: 30

Gly Phe Leu Gly Phe Lys
1               5
```

POLYMERS HAVING THERAPEUTICALLY ACTIVE AGENTS CONJUGATED THERETO, PROCESSES OF PREPARING SAME AND USES THEREOF

RELATED APPLICATIONS

This application is a continuation of U.S. patent application Ser. No. 14/382,776, filed on Sep. 4, 2014, which is a National Phase of PCT Patent Application No. PCT/IL2013/050195 having International Filing Date of Mar. 5, 2013, which claims the benefit of priority of U.S. Provisional Patent Application No. 61/606,557 filed on Mar. 5, 2012. The contents of the above applications are all incorporated by reference as if fully set forth herein in their entirety.

SEQUENCE LISTING STATEMENT

The ASCII file, entitled 69137SequenceListing.txt, created on Mar. 1, 2017, comprising 6,547 bytes, submitted concurrently with the filing of this application is incorporated herein by reference.

FIELD AND BACKGROUND OF THE INVENTION

The present invention, in some embodiments thereof, relates to chemical conjugates and to uses thereof and, more particularly, but not exclusively, to polymeric conjugates having attached thereto a therapeutically active agent and an additional therapeutically active agent and/or a targeting moiety, to processes of preparing such conjugates and to uses thereof.

A polymeric drug delivery system can be designed for passive or active targeting of tumors. Passive targeting refers to the exploitation of the natural (passive) distribution pattern of a drug-carrier in vivo. The latter is based upon the phenomenon named the "enhanced permeability and retention (EPR) effect", and attributed to two factors: (I) the disorganized pathology of angiogenic tumor vasculature with its discontinuous endothelium, leading to hyperpermeability to circulating macromolecules, and (II) the lack of effective tumor lymphatic drainage, which leads to subsequent macromolecular accumulation. The active approach relies upon the selective localization of a ligand at a cell-specific receptor.

A well-designed polymeric drug delivery system, whether it is targeting the tumor site passively or actively, improves the therapeutic index of anti-angiogenic and chemotherapeutic agents by increasing the half-life of low molecular weight drugs, their selective tumor accumulation, their water-solubility and their time of exposure to the tumor vasculature (i.e. to the tumor endothelial cells), while reducing their toxicity.

Angiogenesis is a biological process that involves the sprouting of new blood vessels from pre-existing ones and plays a crucial role in disease development and progression. Pathological angiogenesis has been demonstrated in several diseases, including atherosclerosis, cancer, hypertension, rheumatoid arthritis, diabetes and diabetes related complications such as diabetic retinopathy.

Since tumor growth and metastasis are particularly dependent on the degree of angiogenesis, many drugs have been developed, which target different steps in the multi-step tumor angiogenesis process. However, most of these drugs were shown to be cytostatic rather than cytotoxic and thus do not cause a substantial reduction of tumor volume during the first stage of treatment. Currently approved anti-cancer therapies with recognized anti-angiogenic properties mainly include monoclonal antibodies directed against specific pro-angiogenic factors and/or their receptors (e.g., Avastin, Erbitux, Vectibix, Herceptin); small molecule tyrosine kinase inhibitors (TKIs) of multiple pro-angiogenic growth factor receptors (e.g., Tarceva, Nexavar, Sutent, Iressa); and inhibitors of mTOR (mammalian target of rapamycin) (e.g., Torisel).

Neural cell adhesion molecule (NCAM, CD56) is a cell adhesion molecule structurally belonging to the immunoglobulin superfamily. It is expressed on most brain tumors. In several other tumor types, NCAM expression was shown to be associated with more aggressive biological behavior, increased metastatic capacity and expression of stem-cell markers. NCAM was found to be expressed on tumor endothelial cells, but not on normal endothelial cells (Bussolati et al., Exp Cell Res, 2006). Recently, it was proven that in Wilms' tumor, a common pediatric solid malignancy of the kidney, the cancer stem cells (CSC) population is uniquely characterized by the expression of NCAM (Pode-Shakked et al., J Cell Mol Med, 2008). CSC have been characterized by the expression of NCAM in other cancers as well, including hepatocellular carcinoma, hepatoblastoma and lung carcinoma (Fiegel et al., J Histochem Cytochem, 2004, Xu et al., Carcinogenesis, 2009). Therefore, NCAM provides a specific biomarker than can be exploited to target the cancer stem cells and tumor endothelial cells.

The microtubule-interfering agent Paclitaxel (PTX) is a clinically well-established and highly-effective anti-neoplastic drug used as a monotherapy and in combination therapy mainly for the treatment of prostate, breast, ovarian, and non-small cell lung cancers and it is the drug of choice for the treatment of metastatic breast cancer. It has also shown anti-angiogenic and pro-apoptotic properties [Oldham et al. 2000 *Int. J Oncol.* 16:125-132]. However, due to the hydrophobic nature of the drug, solubilizing agents such as Cremophor EL or ethanol are required for its administration. PTX causes severe adverse side effects such as neutropenia, neuropathies, and when solubilized in Cremophor EL causes hypersensitivity reactions. In addition, only a small amount of the drug localizes in the tumor and the drug is substrate to efflux pumps in particular p-glycoprotein, resulting in multiple drug resistance.

Doxorubicin (DOX) is one of the most potent antineoplastic drugs prescribed alone or in combination with other agents, remaining the compound of its class that has the widest spectrum of activity. Doxorubicin is commonly used in the treatment of Wilms' tumor, as well as various solid tumors and hematological malignancies. Although DOX is recognized as a potent antineoplastic agent, its cardiotoxic effects are the main reason for the dose limited administration. Other common side effects associated with its use are acute nausea and vomiting, stomatitis, gastrointestinal disturbances, alopecia, baldness, neurologic disturbances and bone marrow aplasia.

Conjugation of anti-cancer drugs to copolymers, such as HPMA copolymer or PGA, has been suggested so as to restrict the passage through the blood brain barrier and to prolong the circulating half-life of the drugs, hence inhibiting the growth of tumor endothelial and epithelial cells by exposing the cells to the conjugated drugs in the circulation for a longer time compared to the free drugs.

U.S. Pat. No. 6,884,817 teaches compositions comprising a chemotherapeutic and/or anti-angiogenic drug, conjugated to a water-soluble polyamino acid or soluble metal chelator.

The conjugate paclitaxel-polyglutamate OPAXIO™ (paclitaxel poliglumex, CT-2103) (Formerly known as XYOTAX™) showed promising results in phase III trials and is currently being evaluated for marketing approval.

U.S. patent application Ser. No. 12/117,678 having Publication No. 2008/0279778 also teaches polyglutamate polymers conjugated to a plurality of drugs for use in drug targeting, stabilizing and imaging applications. A HPMA copolymer conjugate of paclitaxel has also been described by Meerum Terwogt et al. [*Anticancer drugs* 2001; 12:315-323].

WO 03/086382 teaches conjugates of water-soluble polymers and the anti-angiogenic agent TNP-470, and their use as anti-tumor agents, in particular their use as carriers of TNP-470 into tumor vessels, and their effect on the neurotoxicity of TNP-470. WO 2006/084054 teaches that an HPMA copolymer-TNP-470 conjugate (caplostatin) can be used in combination with an anti-EGF monoclonal antibody for treating an angiogenic disease.

WO 03/086178 teaches a method for decreasing or inhibiting disorders associated with vascular hyperpermeability by the administration of an effective amount of an anti-angiogenic compound or a compound capable of increasing cell-cell contacts by stabilizing tight junction's complexes and increasing contact with the basement membrane. According to the teachings of WO 03/086178, HPMA copolymer-TNP-470 inhibited vascular endothelial growth factor (VEGF)-induced vessel hyperpermeability and inhibited angiogenesis both in vitro and in vivo.

Integrins are a class of receptors involved in the mechanism of cell adhesion. Since the 1980s it is well recognized that integrins play a key role in cell matrix interactions and hence in angiogenesis.

The integrins are heterodimeric transmembrane glycoproteins that compose a diverse family of 19 α and eight β subunits. An integrin with a well-characterized involvement in angiogenesis and tumor invasiveness is $α_vβ_3$. $α_vβ_3$ integrins are known to bind the RGD sequence (Arg-Gly-Asp), which constitutes the recognition domain of different proteins, such as laminin, fibronectin and vitronectin. The RGD sequence represents the minimal amino acid domain, in several extracellular matrix proteins, which has been demonstrated to be the binding site of the transmembrane integrins proteins family [Bazzoni et al. 1999, *Current Opinion in Cell Biology*; (11) pp. 573-581].

It has been demonstrated that RGD-containing peptides, either isolated from phage peptides library or biochemically synthesized, were able to compete with extracellular matrix proteins on binding to integrins [Haubner et al. 1997, *Angew. Chem. Int. Ed. Engl.*; (36) pp. 1374-1389]. Tumor-induced angiogenesis can be targeted in vivo by antagonizing the $α_vβ_3$ integrin with small peptides containing the RGD amino acid sequence.

It has been further found that the substrate specificity of RGD-containing peptides results from the different conformations of the RGD sequence in different matrix proteins. For example, the bis-cyclic peptide E-[c(RGDfK)$_2$] is a ligand-based vascular-targeting agent that binds to integrin $α_vβ_3$ (Eldar-Boock et al, Biomaterials 32(15):3862-3874, 2011).

Chen et al. reported [J. Med. Chem. 2005; 48:1098-1106] the synthesis and antitumor activity of paclitaxel (PTX) conjugated with a bis-cyclic RGD (E[RGDyK]$_2$) in a metastatic breast cancer cell line.

Mitra et al. report [*Journal of Controlled Release* 2006; 28: 175-183] the biodistribution and tumor targeting properties of N-(2-hydroxypropyl)methacrylamide (HPMA) copolymer based conjugates of mono-(RGDfK) and doubly cyclized (RGD4C) $α_vβ_3$ binding peptides.

WO 2006/012355 teaches an anti-angiogenic polymer conjugate for treatment of solid tumors comprising a chemical moiety targeting cell-surface proteins of endothelial cells at an angiogenic site. The chemical moiety taught in the application may be a ligand such as RGD4C or RGDfK for a cell-surface receptor, such as, for example, an integrin. The polymer conjugate taught by WO 2006/012355 may further comprise at least one side chain comprising a chelator capable of chelating a pharmaceutically acceptable radioactive label. Wan et al. [2003 *Proc. Int'l Symp. Control. Rel. Bioact. Mater.* Vol 30: 491-492] teach targeting endothelial cells using HPMA copolymer-doxorubicin-RGD conjugates.

Bisphosphonates, such as alendronate, are molecules used to treat osteoporosis, bone metastases and to prevent bone fractures. These compounds exhibit an exceptionally high affinity to the bone mineral hydroxyapatite, and therefore are known to be used also as a targeting moiety (Uludag, H. *Curr Pharm Des* 2002; 8: 1929-1944).

Alendronate is considered potent for the treatment of bone related diseases and cancer-associated hypercalcemia. It was shown to have antitumor effect in several in vivo cancer models through several different mechanisms [Tuomela et al. 2008, *BMC Cancer* 8:81; Molinuevo et al. 2007, *Eur J Pharmacol* 562:28-33; Hashimoto et al. 2005, *Cancer Res* 65: 540-545]. In addition, alendronate was found to have anti-angiogenic activity through (i) suppression of VEGF-induced Rho activation in an ovarian cancer model [Hashimoto et al. 2007, *Biochem Biphys Res Commun* 354: 478-484], (ii) inhibition of farnesyl pyrophosphate synthase, in the mevalonate pathway [Russell RG 2007, *Pediatrics* 119 Suppl 2: S150-162]; and (iii) regulation of cellular level of MMP-2 expression in osteosarcoma cell lines [Cheng et al. 2004, *Pediatr Blood Cancer* 42; 410-415].

WO 2004/062588 teaches water soluble polymeric conjugate for bone targeted drug delivery with improved pharmacokinetics parameters and better water solubility of the loaded drugs. The polymeric drug delivery systems taught by this application are based on hydroxypropyl methacrylate (HPMA) copolymer conjugates of bone-targeting drugs such as alendronate and D-Asp$_8$ together with a bone-related therapeutic agent (e.g., tetracycline).

PK2 (FCE28069) is a HPMA copolymer-doxorubicin-galactosamine conjugate, which was designed as a treatment for hepatocellular carcinoma or secondary liver disease [Seymour et al. *Journal of Clinical Oncology* 2002; 20: 1668-1676]. Galactosamine binds to the hepatic asialoglycoprotein receptor (ASGPR) thus serving as a specific hepatic targeting moiety. These components are linked to the HPMA copolymer via an enzymatically-biodegradable linker which permits the release of free doxorubicin within the liver, thus increasing the drug concentration in its site of action. The enzymatic degradable linker is a tetrapeptide spacer (Gly-Phe-Leu-Gly; GFLG), designed for cleavage by lysosomal cathepsins.

O'hare et al. [*Journal of Drug Targeting* 1993; 1:217-229] have synthesized HPMA copolymers containing doxorubicin and melanocyte stimulating hormone (MSH) as a melanoma specific targeting moiety. Both the doxorubicin and the melanocyte stimulating hormone were linked to the HPMA polymer via an enzymatically biodegradable linker.

Hruby et al. [*Journal of Applied Polymer Science* 2006; 101:3192-3201] have synthesized novel polymeric drug-delivery systems designed for bone targeting of anti-neoplastics based on biocompatible HPMA copolymers containing hydroxybisphosphonate targeting moieties and the model drugs radiotherapeutics $^{125}$I, imaging agent $^{111}$In, or the anticancer drug Doxorubicin.

WO 2009/141823 discloses conjugates of polymers or copolymers (e.g., HPMA) having attached thereto an anti-angiogenic agent (e.g., PTX) and a bisphosphonate bone targeting agent such as alendronate, and uses thereof.

WO 2009/141827 discloses conjugates of hydroxypropyl methacrylamide (HPMA) copolymer-derived copolymers having attached thereto TNP-470 and a high load (e.g., higher than 3 mol %) of alendronate (ALN), prepared by RAFT polymerization.

WO 2009/141826 discloses conjugates of a polymer (e.g., PGA) having attached thereto an angiogenesis targeting moiety (e.g., RGD-containing peptide) and an anti-cancer agent or anti-angiogenic agent (e.g., PTX), and uses thereof.

The teachings of WO 2009/141823, WO 2009/141826 and WO 2009/141827 are incorporated by reference as if fully set forth herein.

The "reversible addition-fragmentation chain transfer" (RAFT) polymerization technique typically involves the use of thiocarbonylthio compounds, such as dithioesters, dithiocarbamates, trithiocarbonates, and xanthates in order to mediate the polymerization via a reversible chain-transfer process. This allows access to polymers with low polydispersity and high functionality.

Additional background art includes Satchi-Fainaro et al., 2002, *Bioorganic & Medicinal Chemistry*, 10 (9), 3023-3029; Marsili et al., 2008, Peptides 29, 2232-2242; Segal et al. *PLoS One* 2009, 4(4):e5233; Eldar-Boock et al. *Biomaterials* 2011, 32(15):3862-3874; Pan et al., Biomacromolecules. 2011; 12(1):247-52.

SUMMARY OF THE INVENTION

The present inventors have now devised and successfully prepared and practiced polymeric conjugates in which two or more therapeutically active agents, particularly such agents which act synergistically, are attached to a polymeric backbone. The present inventors have further devised polymeric conjugates in which one or more therapeutically active agents and an NCAM targeting moiety are attached to the polymer.

According to an aspect of some embodiments of the present invention there is provided a polymeric conjugate comprising a polymeric backbone comprised of a plurality of backbone units and being represented by Formula I:

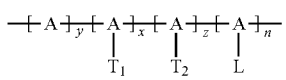

Formula I wherein:
A is a backbone unit within the polymeric backbone;
A-T1 is a backbone unit within the polymeric backbone having attached thereto paclitaxel;
A-T2 is a backbone unit within the polymeric backbone having attached thereto a therapeutically active agent selected from the group consisting of doxorubicin and TNP-470;
A-L is a backbone unit having attached thereto a targeting moiety;
y ranges from 50 to 99.9 mol percent;
x ranges from 0.1 to 20 mol percent; and
z ranges from 0.1 to 20 mol percent; and n ranges from 0 to 10 mol percents,
provided that:
when n is 0, z ranges from 0.1 to 20 mol percents; and
when z is 0, n ranges from 0.1 to 10 mol percents and the targeting moiety is a ligand of a cell-surface receptor expressed in tumor cells and/or endothelial cells, and the cell surface receptor is neural cell adhesion molecule (NCAM).

According to some embodiments of the present invention, the targeting moiety is a ligand of a cell-surface receptor expressed in tumor cells and/or endothelial cells.

According to some embodiments of the present invention, the cell surface receptor is a neural cell adhesion molecule (NCAM) and the targeting moiety is a NCAM-targeting peptide.

According to some embodiments of the present invention, L is a peptide comprising an amino acid sequence as set forth in SEQ ID NO:6.

According to some embodiments of the present invention, L is a peptide having an amino acid sequence as set forth in SEQ ID NO:3.

According to some embodiments of the present invention, the cell-surface receptor is an angiogenesis-associated receptor and the targeting moiety is an RGD-containing moiety.

According to some embodiments of the present invention, z ranges from 0.1 to 20 mol percents.

According to some of these embodiments of the present invention, T2 is doxorubicin.

According to some of these embodiments of the present invention, T2 is TNP-470.

According to some embodiments of the present invention, the plurality of backbone units further comprises -[A-T3]$_k$- units, whereas T3 is alendronate and k ranges from 0.1 to 20 mol percents.

According to some embodiments of the present invention, the conjugate further comprises a labeling moiety attached thereto.

According to some embodiments of the present invention, the labeling moiety is attached to a terminus of the polymeric backbone.

According to some embodiments of the present invention, the plurality of backbone units further comprises -[A-P]m units, whereas: P is the labeling moiety; A-P is a backbone unit having the labeling moiety attached thereto; and m ranges from 0.1 to 50 mol percents.

According to some embodiments of the present invention, when n ranges from 0.1 to 10 mol percents, the labeling moiety is attached to the targeting moiety.

According to some embodiments of the present invention, the plurality of backbone units forms a polymeric backbone corresponding to a polymeric backbone of polyglutamic acid (PGA).

According to some embodiments of the present invention, the plurality of backbone units forms a polymeric backbone corresponding to a polymeric backbone of poly(hydroxyalkylmethacrylamide) (HPMA) copolymer.

According to some embodiments of the present invention, T1 is attached to the backbone unit via a biocleavable linker.

According to some embodiments of the present invention, the biocleavable linker is a hydrolizable linker (e.g., an ester bond).

According to some embodiments of the present invention, the biocleavableable linker is an enzymatically cleavable linker.

According to some embodiments of the present invention, the enzymatically cleavable linker is cleaved by an enzyme which is overexpressed in tumor tissues.

According to some embodiments of the present invention, T1 is attached to the backbone unit and/or to the linker via a spacer.

According to some embodiments of the present invention, z ranges from 0.1 to 20 mol percents, T2 is doxorubicin, and the doxorubicin is attached to the backbone unit via a biocleavable linker.

According to some embodiments of the present invention, the biocleavable linker is an enzymatically cleavable linker.

According to some embodiments of the present invention, the enzymatically cleavable linker is cleaved by an enzyme which is overexpressed in tumor tissues.

According to some embodiments of the present invention, the linker comprises the amino acid sequence -Gly-Phe-Leu-Gly-.

According to some embodiments of the present invention, the linker is an acid-cleavable linker.

According to some embodiments of the present invention, the linker comprises a hydrazone moiety.

According to some embodiments of the present invention, x is greater than 1 mol percent.

According to some embodiments of the present invention, z is greater than 1 mol percent.

Figure 18:
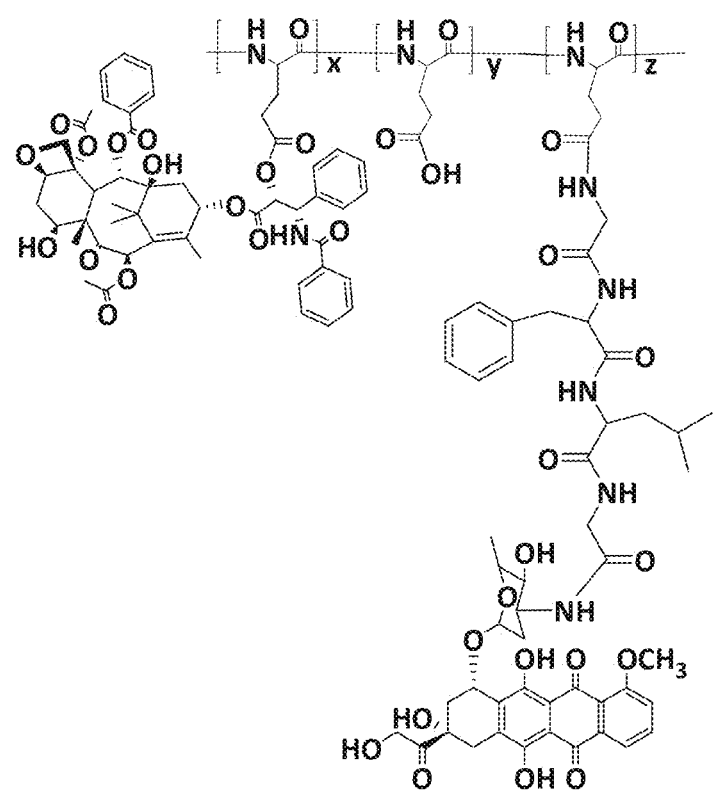

According to some embodiments of the present invention, z ranges from 0.1 to 20 mol percents, T2 is doxorubicin and the polymeric backbone corresponds to a polymeric backbone of polyglutamic acid (PGA). Chemical structures of exemplary such conjugates are depicted in FIGS. 18 and 19D.

According to some embodiments of the present invention, n ranges from 0.1 to 10 mol percents, and the polymeric backbone corresponds to a polymeric backbone of polyglutamic acid (PGA). A structure of an exemplary such conjugate is presented in FIG. 31.

According to some embodiments of the present invention, the conjugate further comprises a labeling moiety attached thereto.

According to an aspect of some embodiments of the present invention there is provided a pharmaceutical composition comprising, as an active ingredient, any of the conjugates described herein and a pharmaceutically acceptable carrier.

According to some embodiments of the present invention, the pharmaceutical is packaged in a packaging material and identified in print, in or on the packaging material, for use in the treatment of cancer or of a medical condition associated with angiogenesis.

According to an aspect of some embodiments of the present invention there is provided a conjugate as described herein, for use in a method of treating cancer or a medical condition associated with angiogenesis.

According to an aspect of some embodiments of the present invention there is provided method of treating cancer or a medical condition associated with angiogenesis in a subject in need thereof, the method comprising administering to the subject a therapeutically effective amount of any of the conjugates described herein.

According to an aspect of some embodiments of the present invention there is provided a use of any of the conjugates described herein in the manufacture of a medicament for use in the treatment of cancer or a medical condition associated with angiogenesis.

According to some embodiments of the present invention, the medical condition associated with angiogenesis is selected from the group consisting of atherosclerosis, hypertension, rheumatoid arthritis, diabetes and diabetes related complications.

According to an aspect of some embodiments of the present invention there is provided the cancer is selected from the group consisting of renal cell carcinoma, Wilm's tumor, breast cancer, ovarian cancer, osteosarcoma, glioblastoma, and lung adenocarcinoma.

According to an aspect of some embodiments of the present invention there is provided a conjugate comprising a polymeric backbone comprised of a plurality of backbone units, wherein the polymeric backbone corresponds to a polymeric backbone of polyglutamic acid and at least a portion of the backbone units has doxorubicin attached thereto through a linker that comprises a hydrazone moiety, and a process of preparing same.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWING(S)

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

Figure 1B:
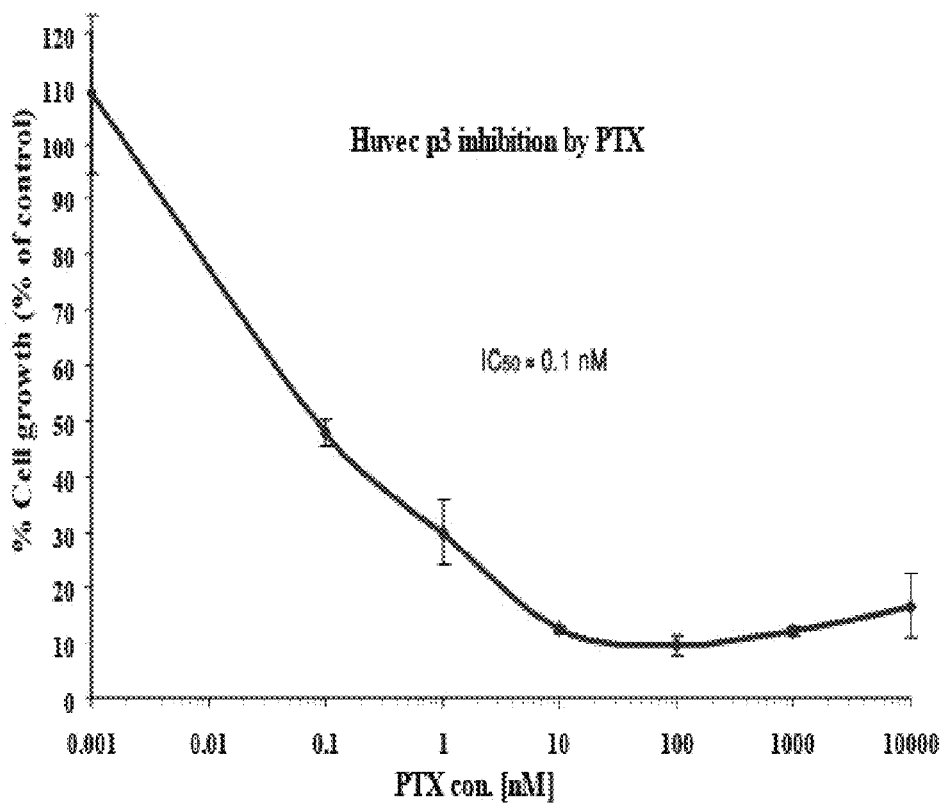
Figure 2A:
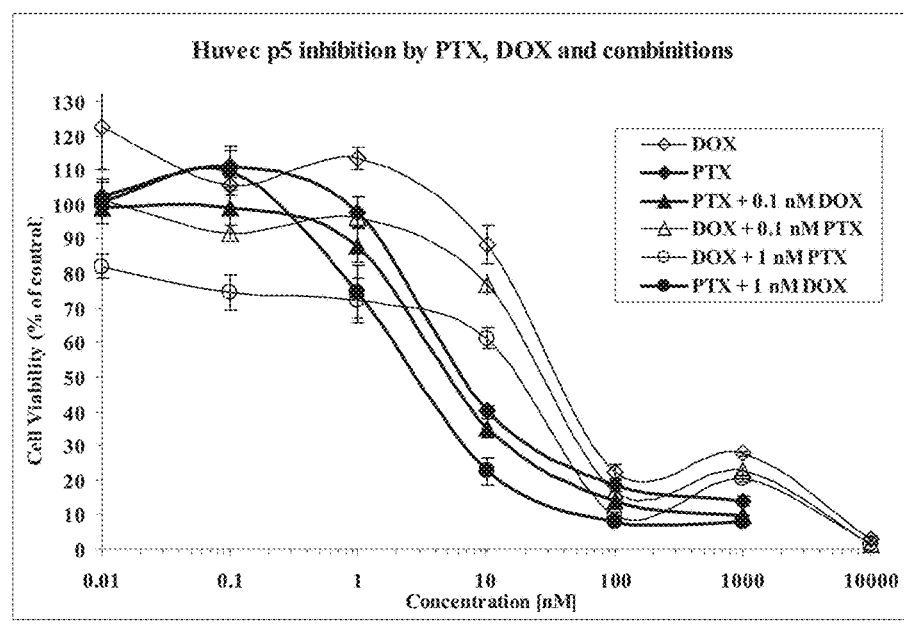
Figure 2B:
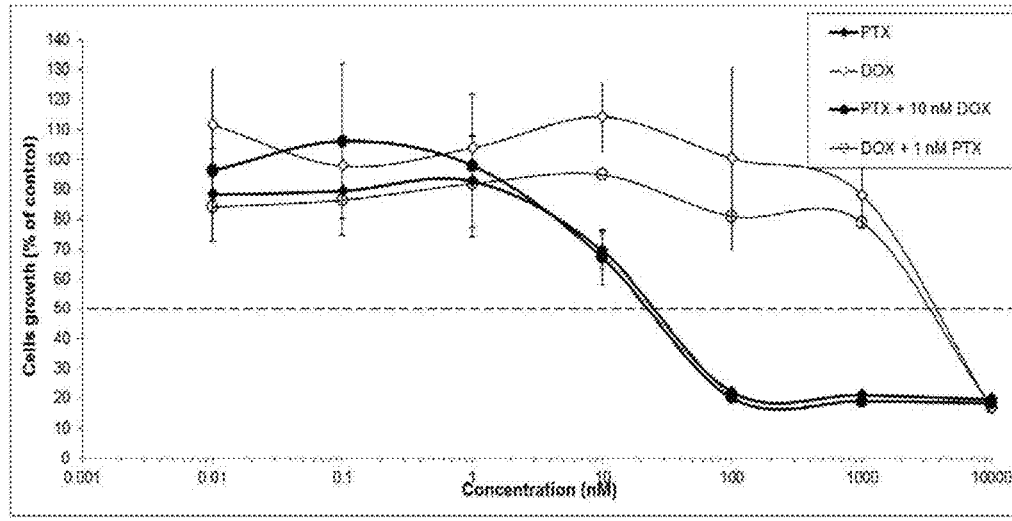
Figure 3A:
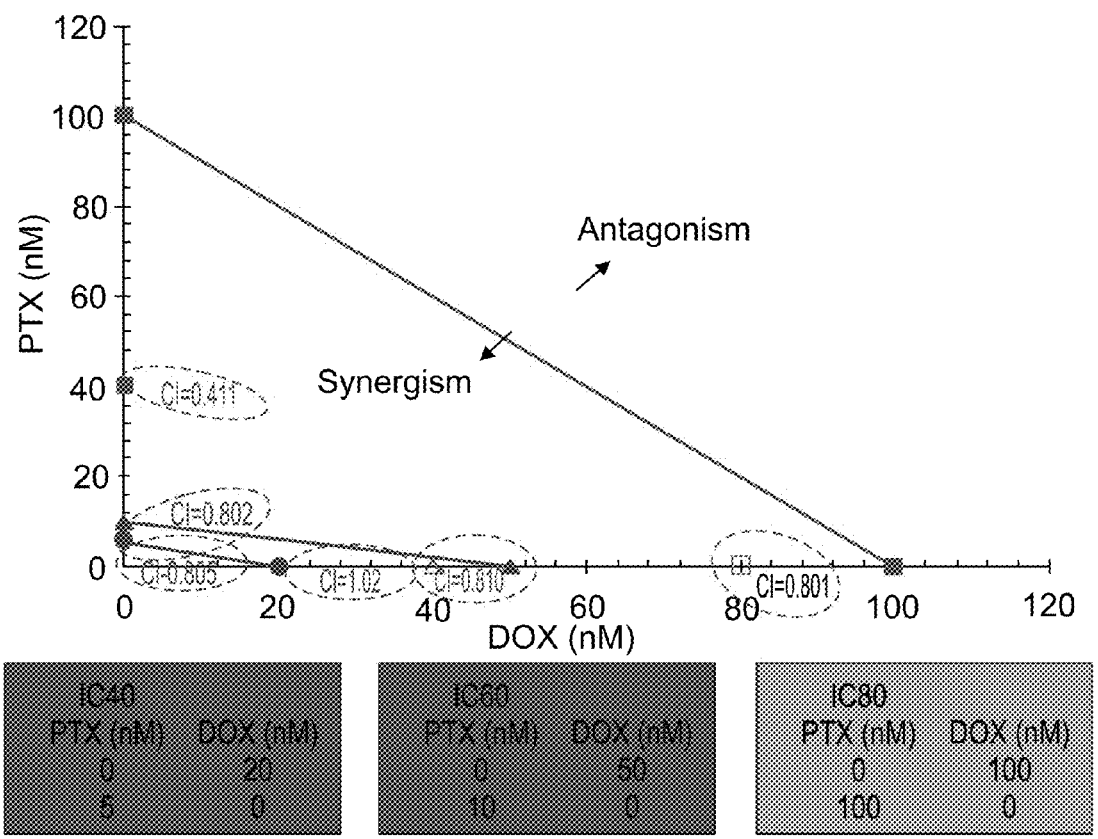
Figure 3B:
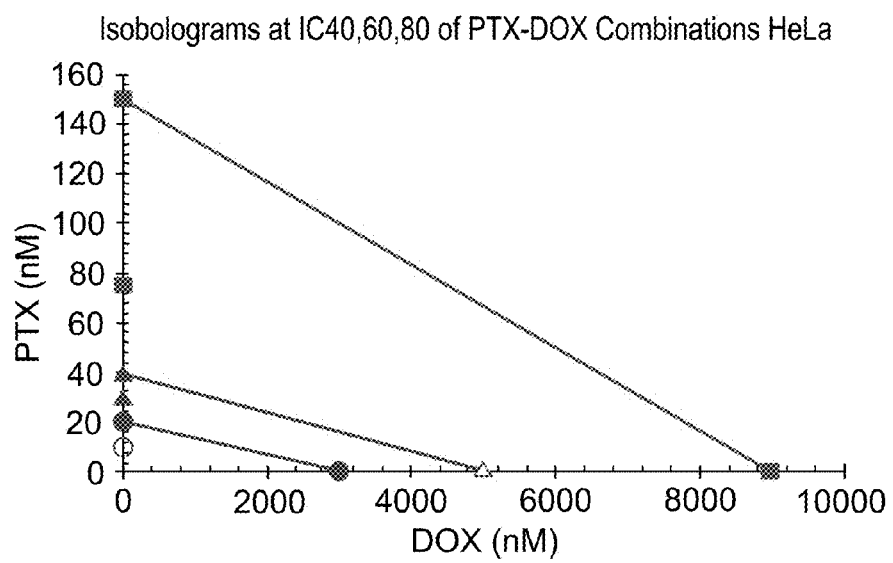
Figure 4A:
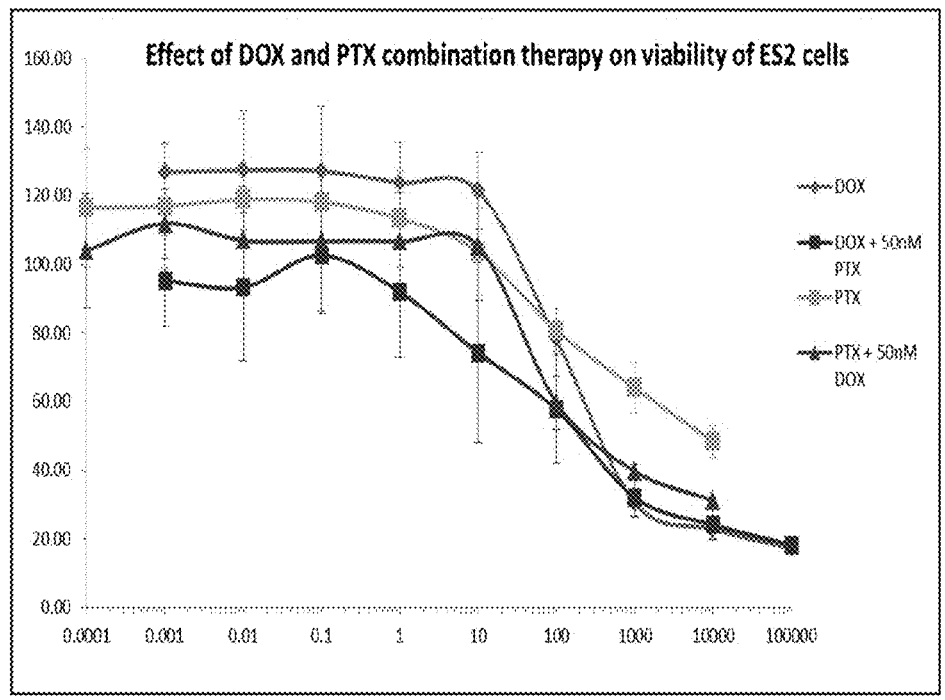
Figure 4B:
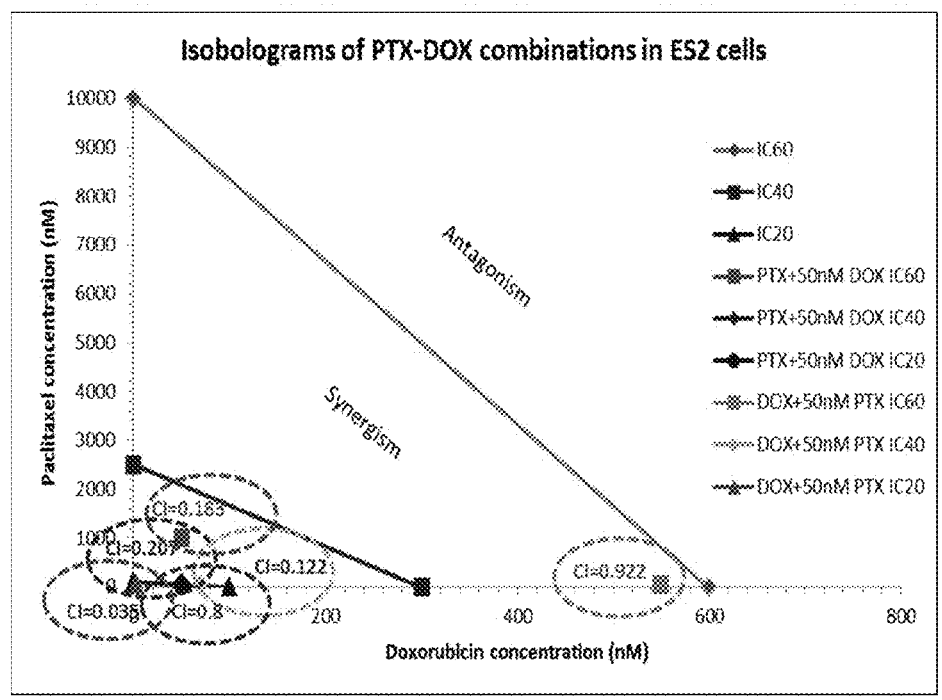
Figure 5A:
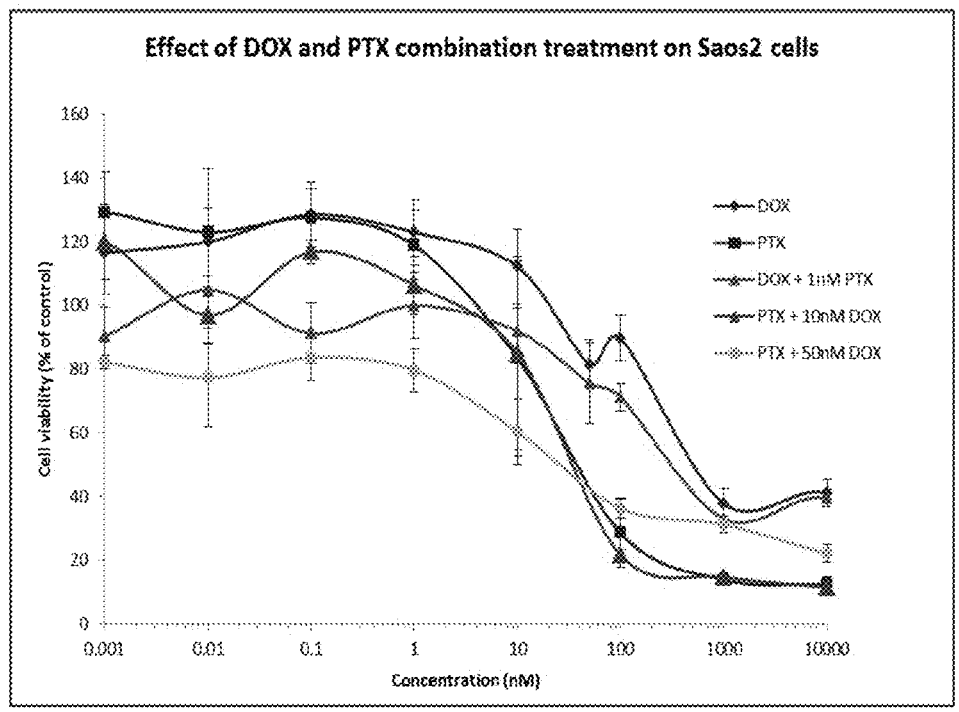
Figure 5B:
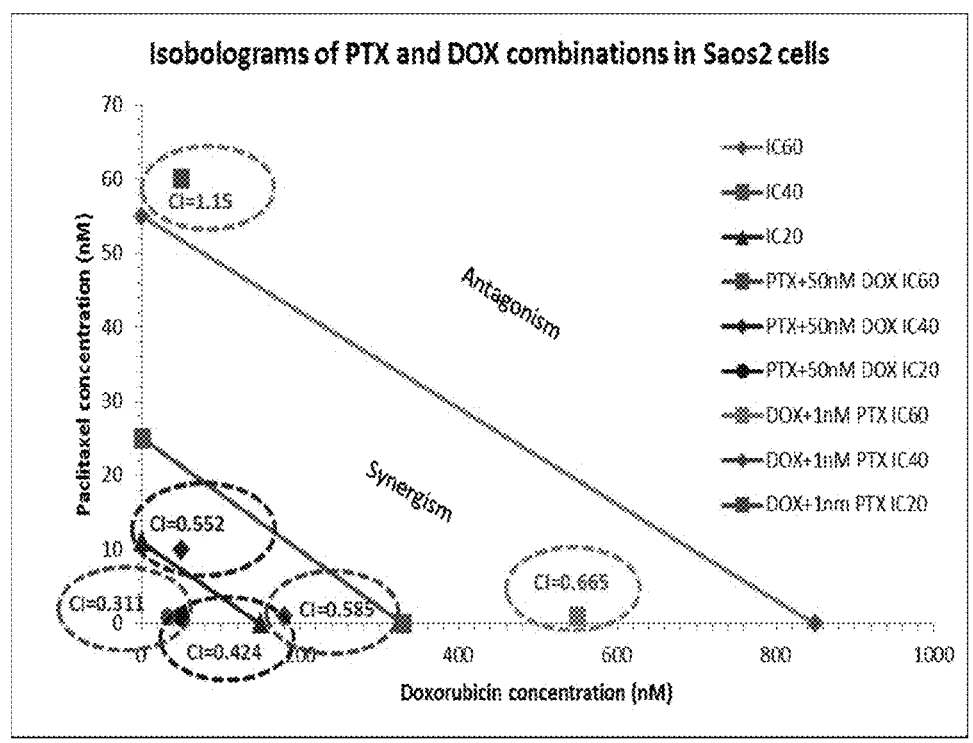
Figure 6A:
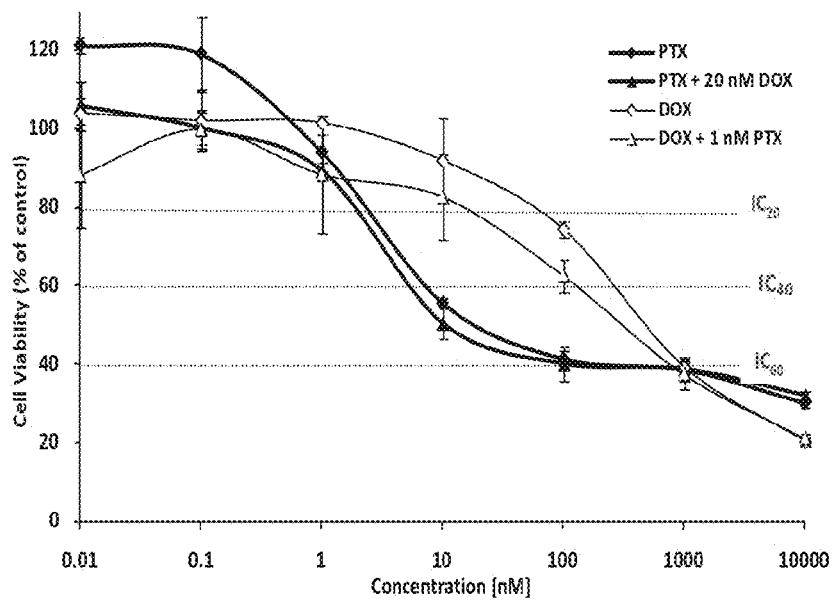
Figure 6B:
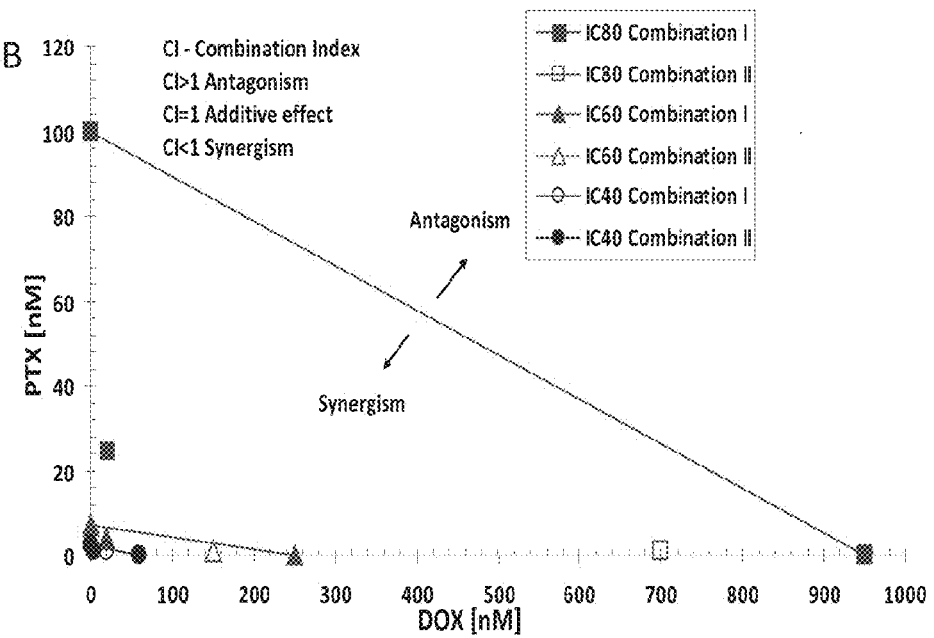
Figure 8A:
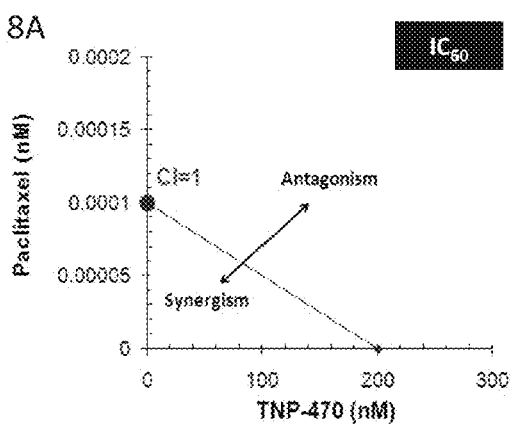
Figure 8B:
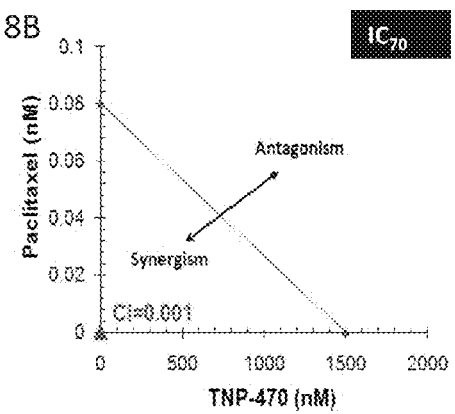
Figure 8C:
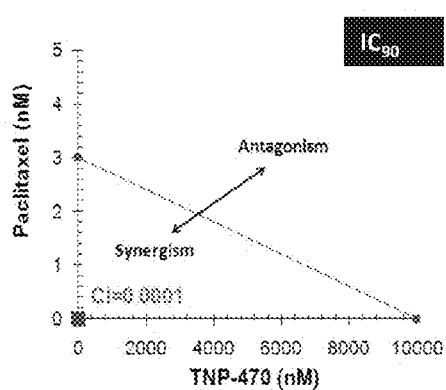
Figure 9:
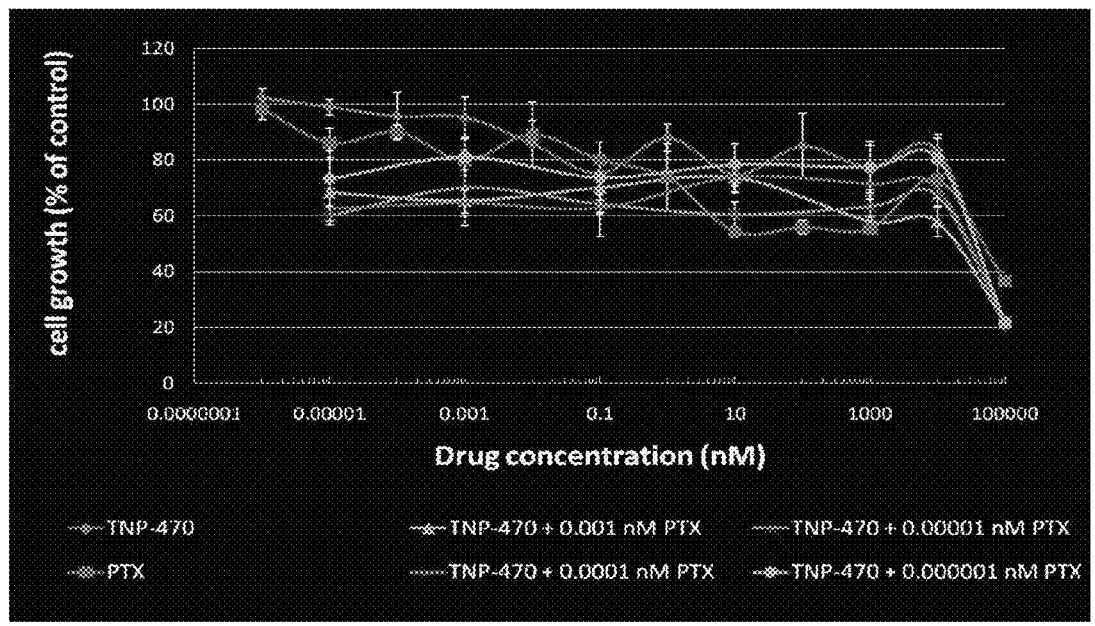
Figure 10:
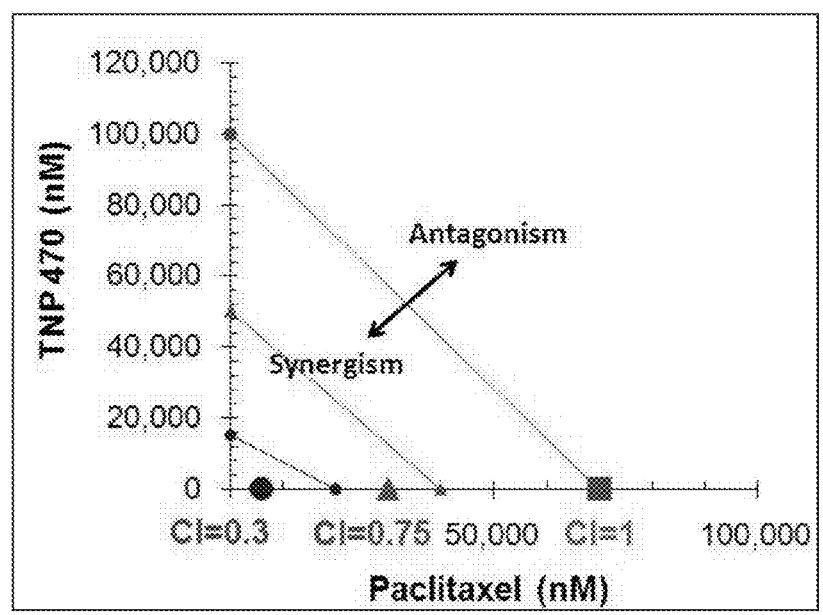
Figure 11A:
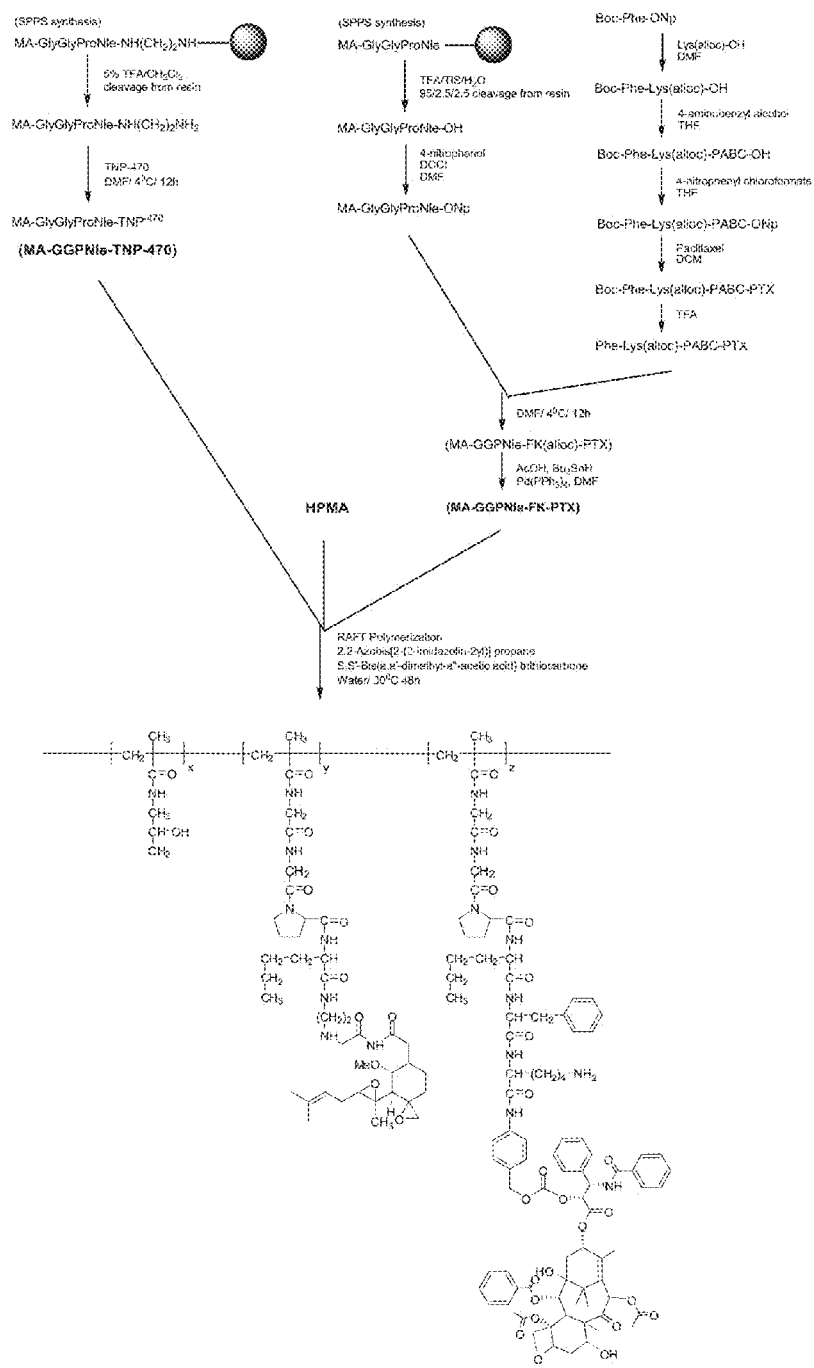
Figure 11B:
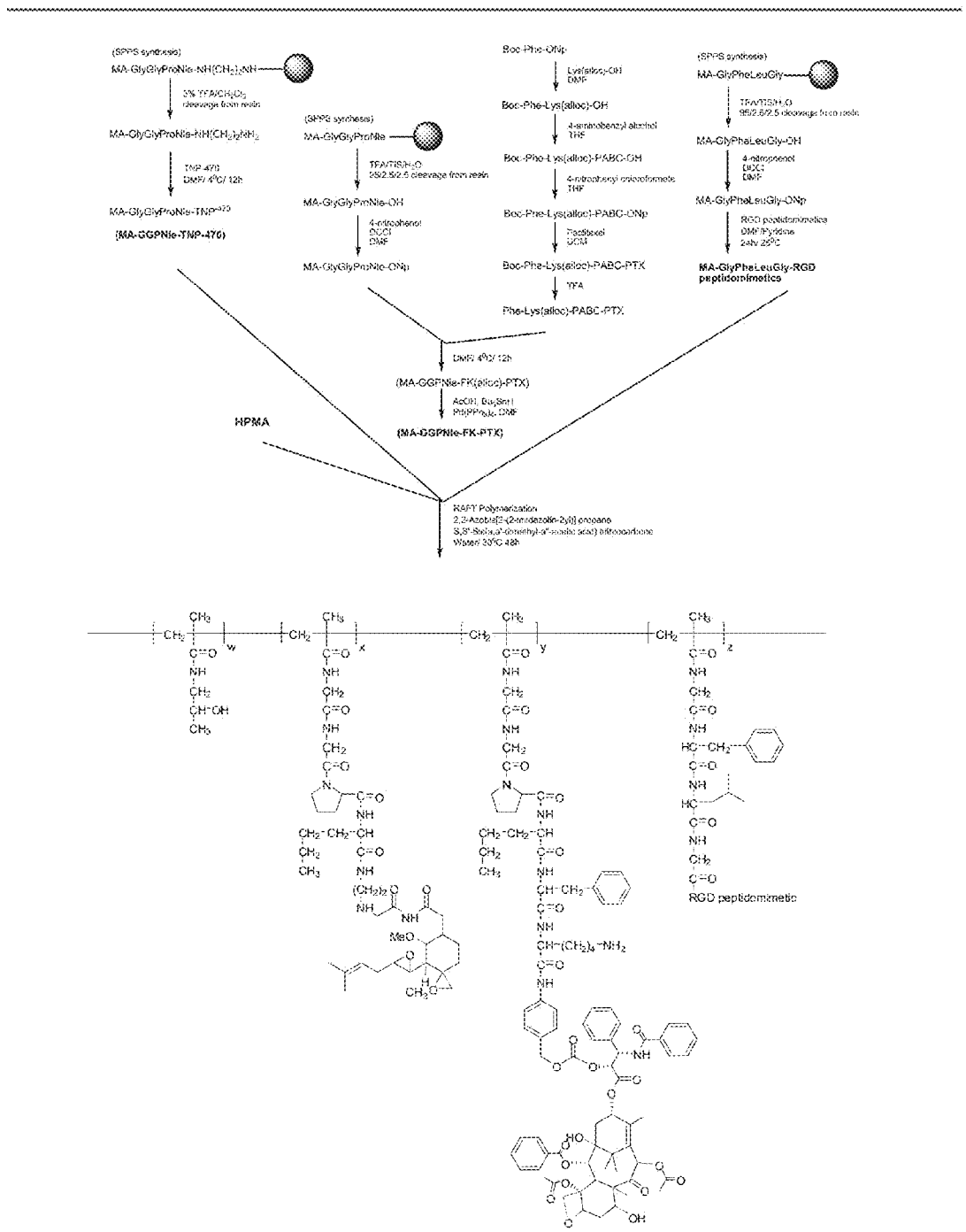
Figure 11C:
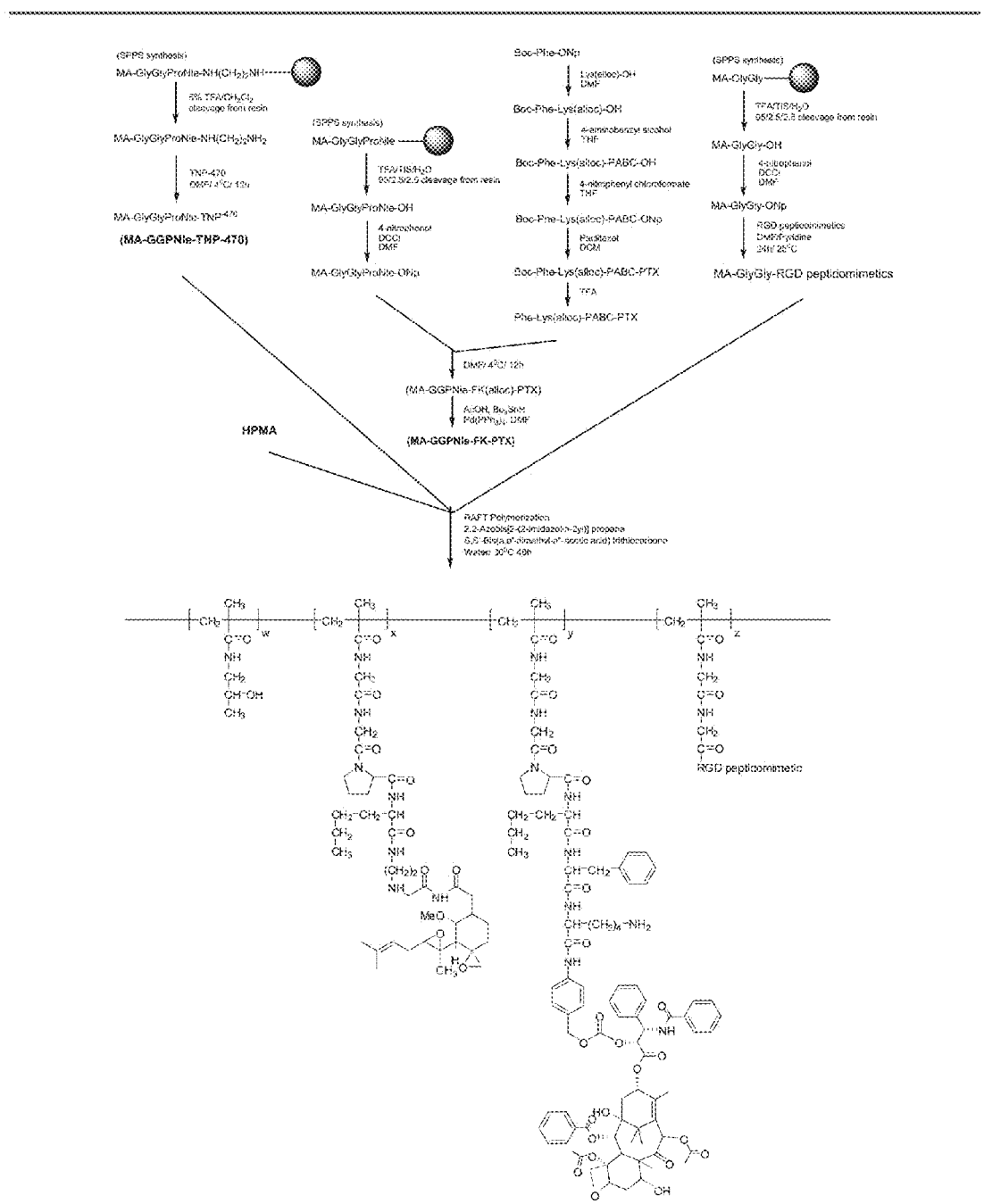
Figure 11D:
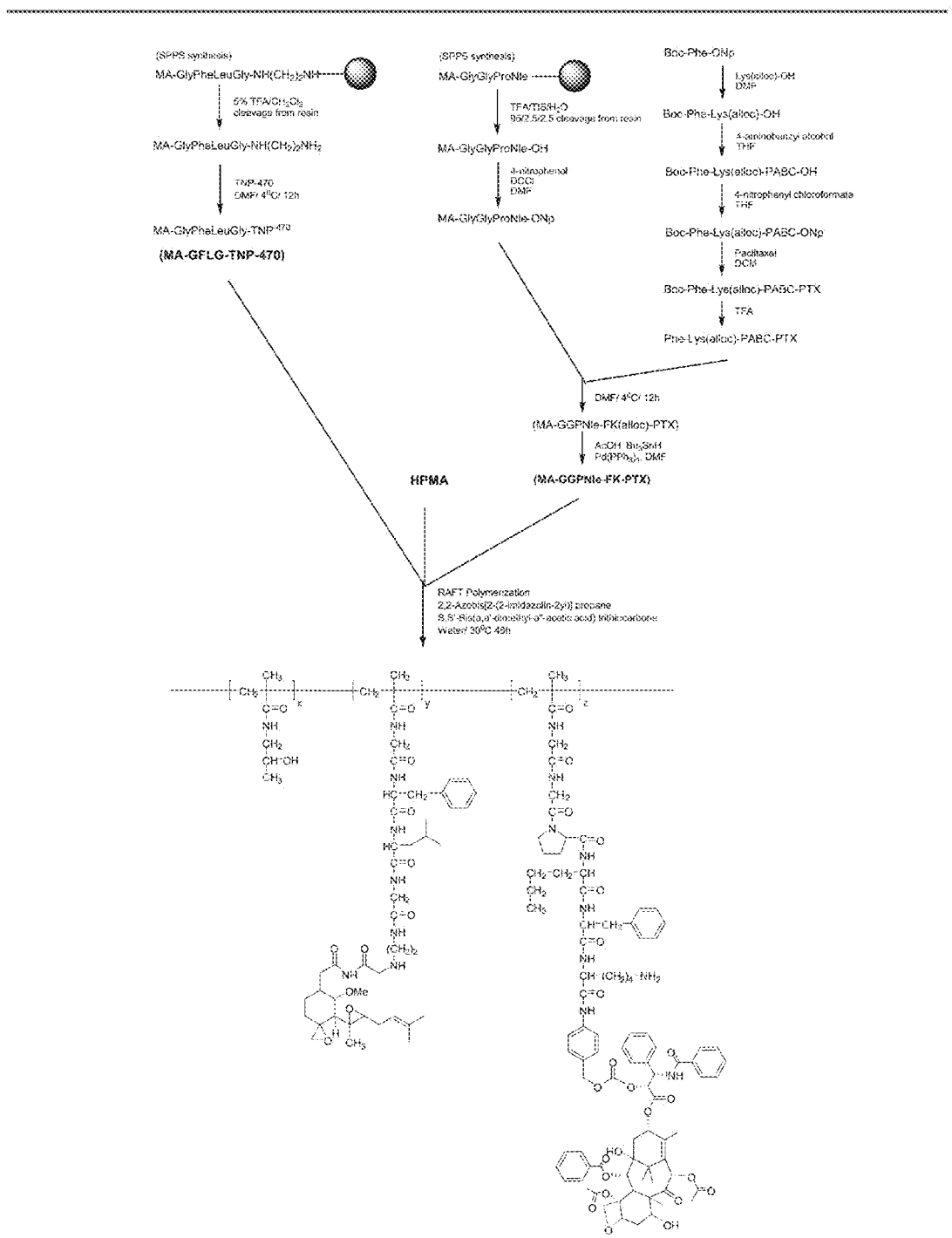
Figure 11E:
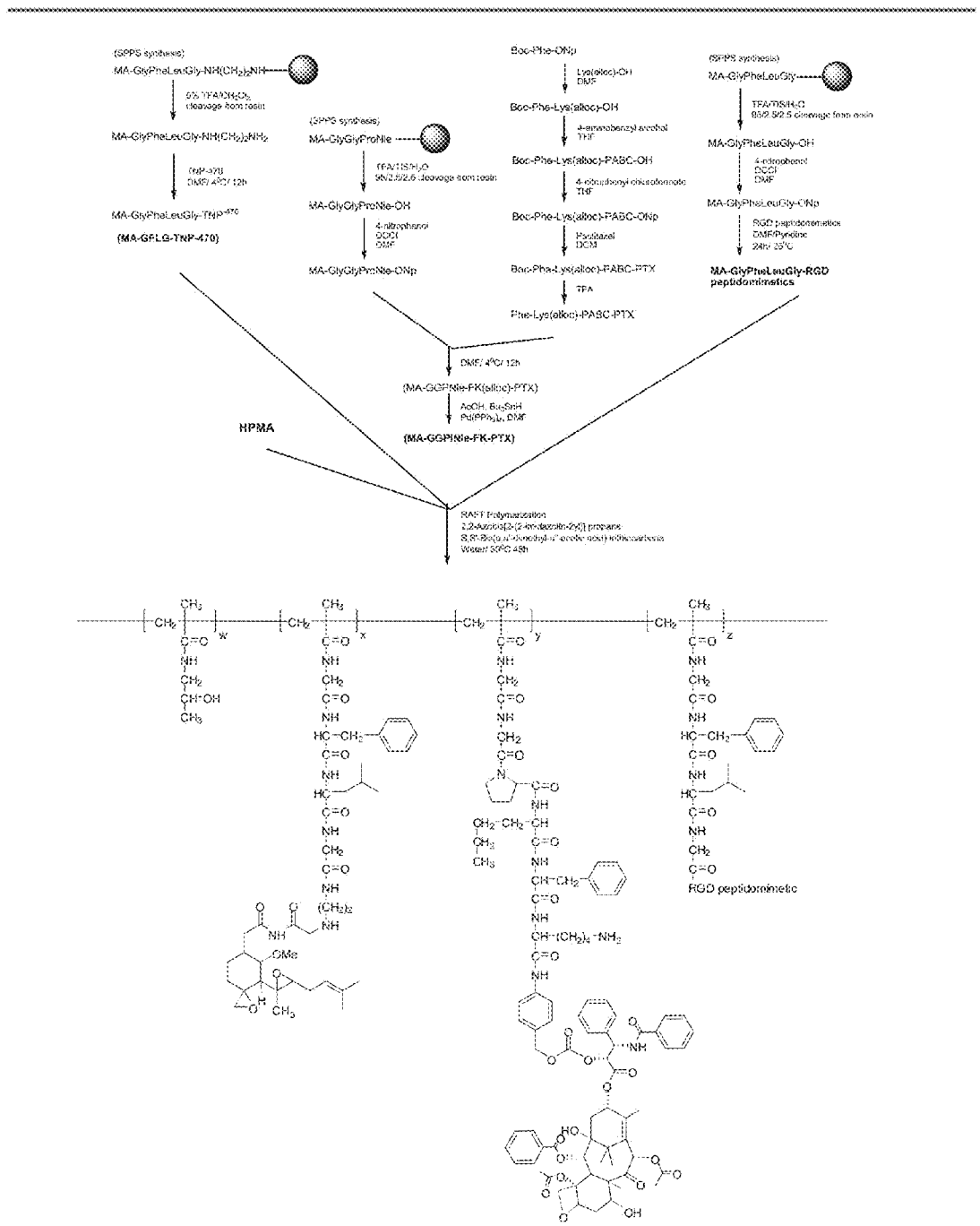
Figure 11F:
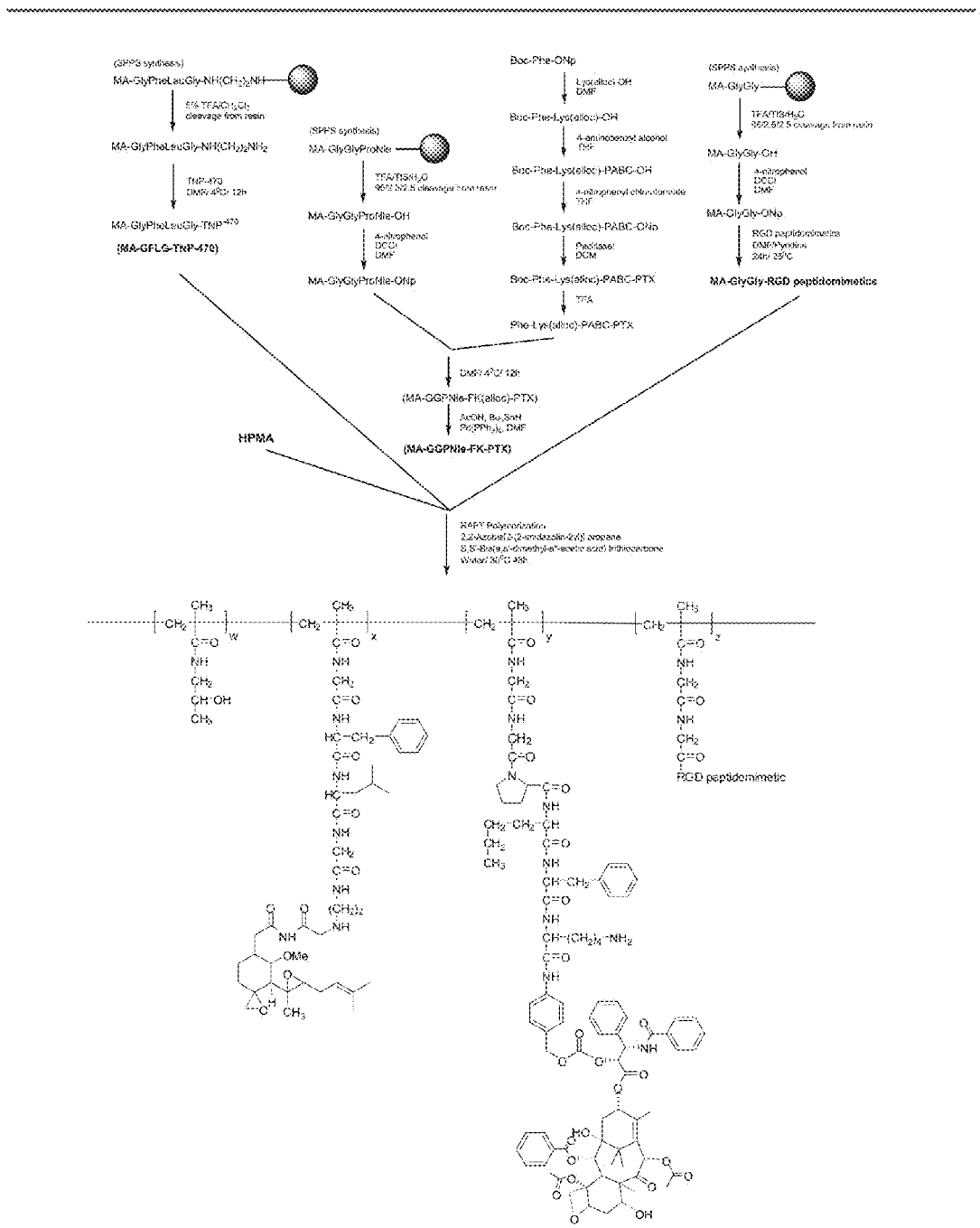
Figure 12A:
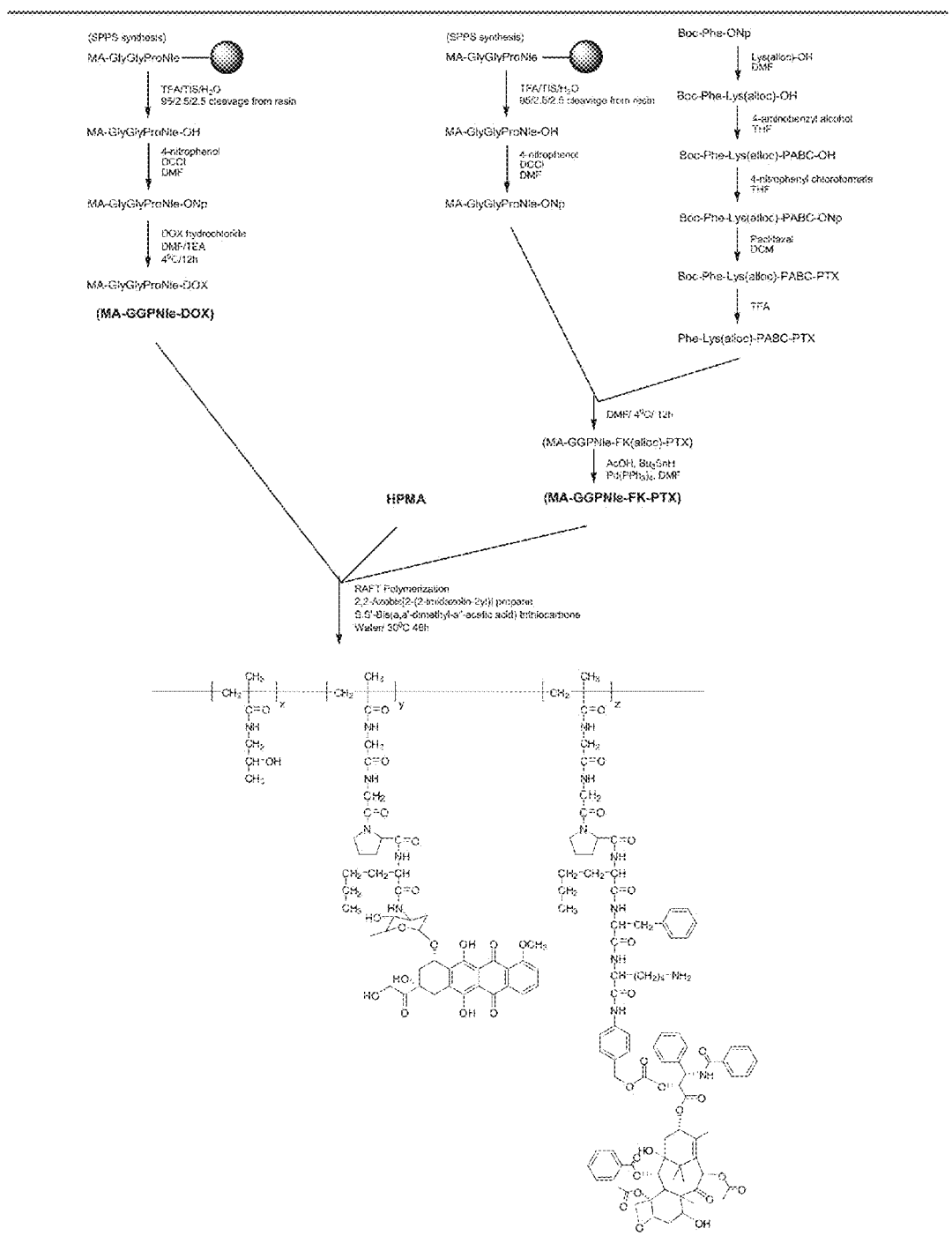
Figure 12B:
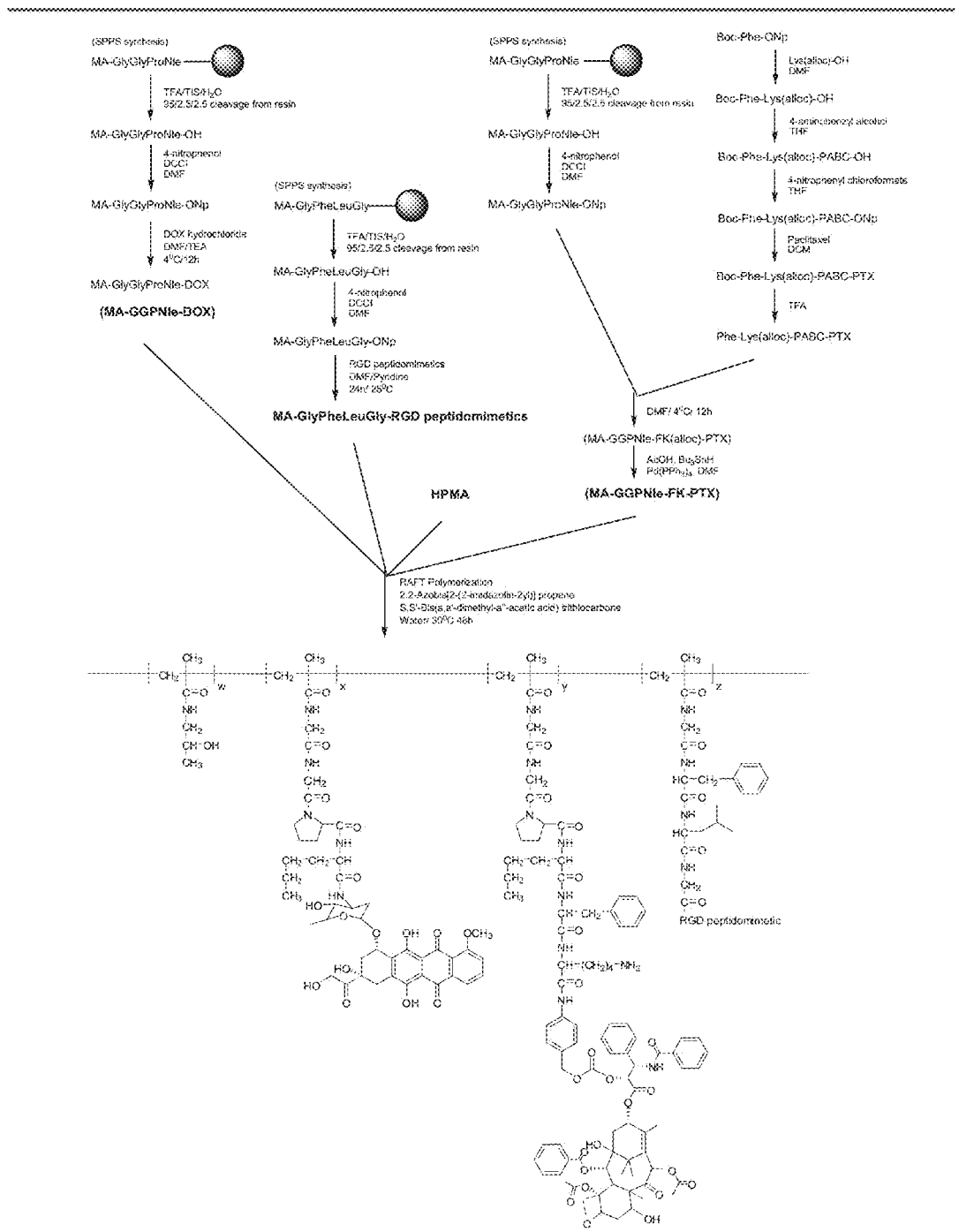
Figure 12C:
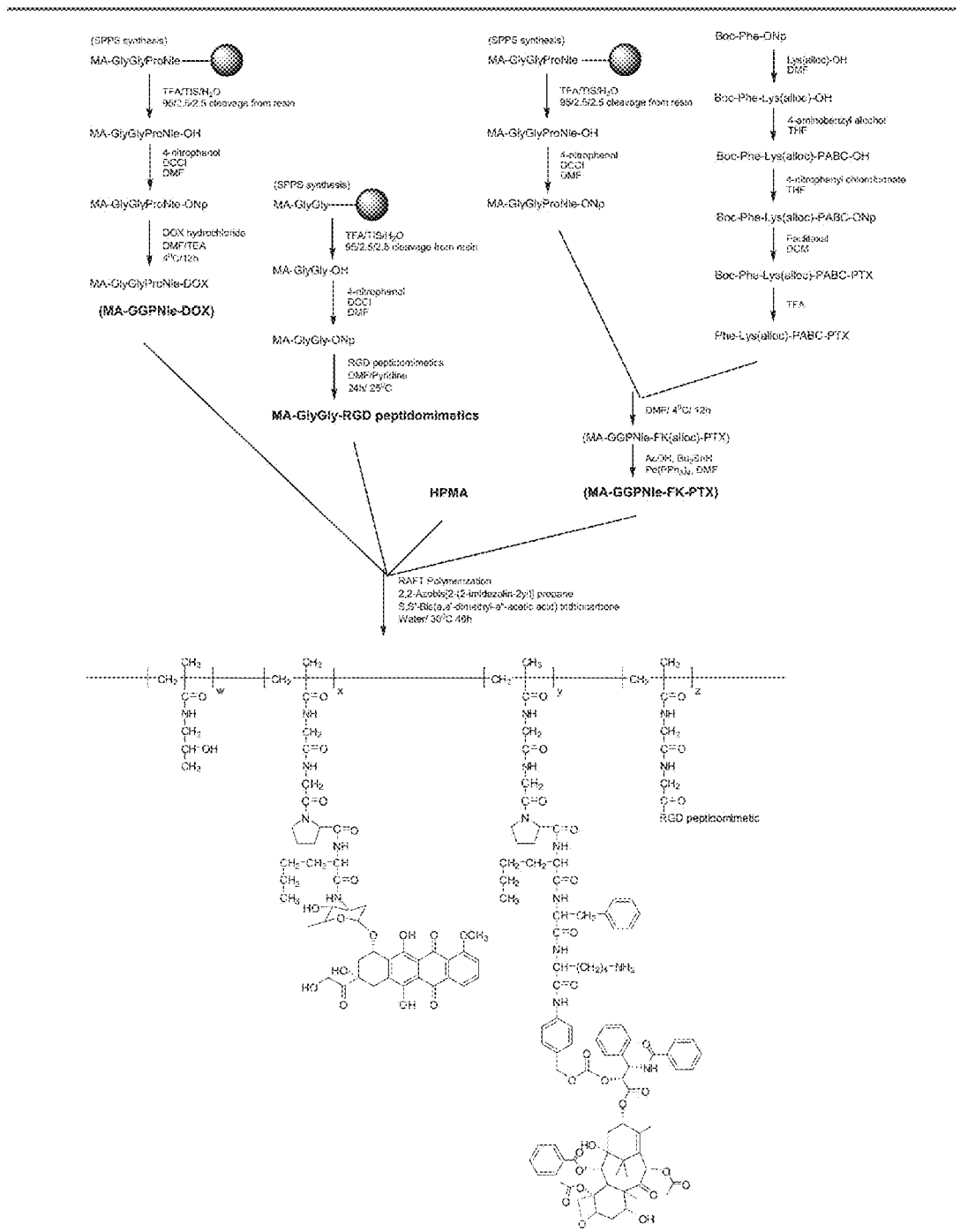
Figure 12D:
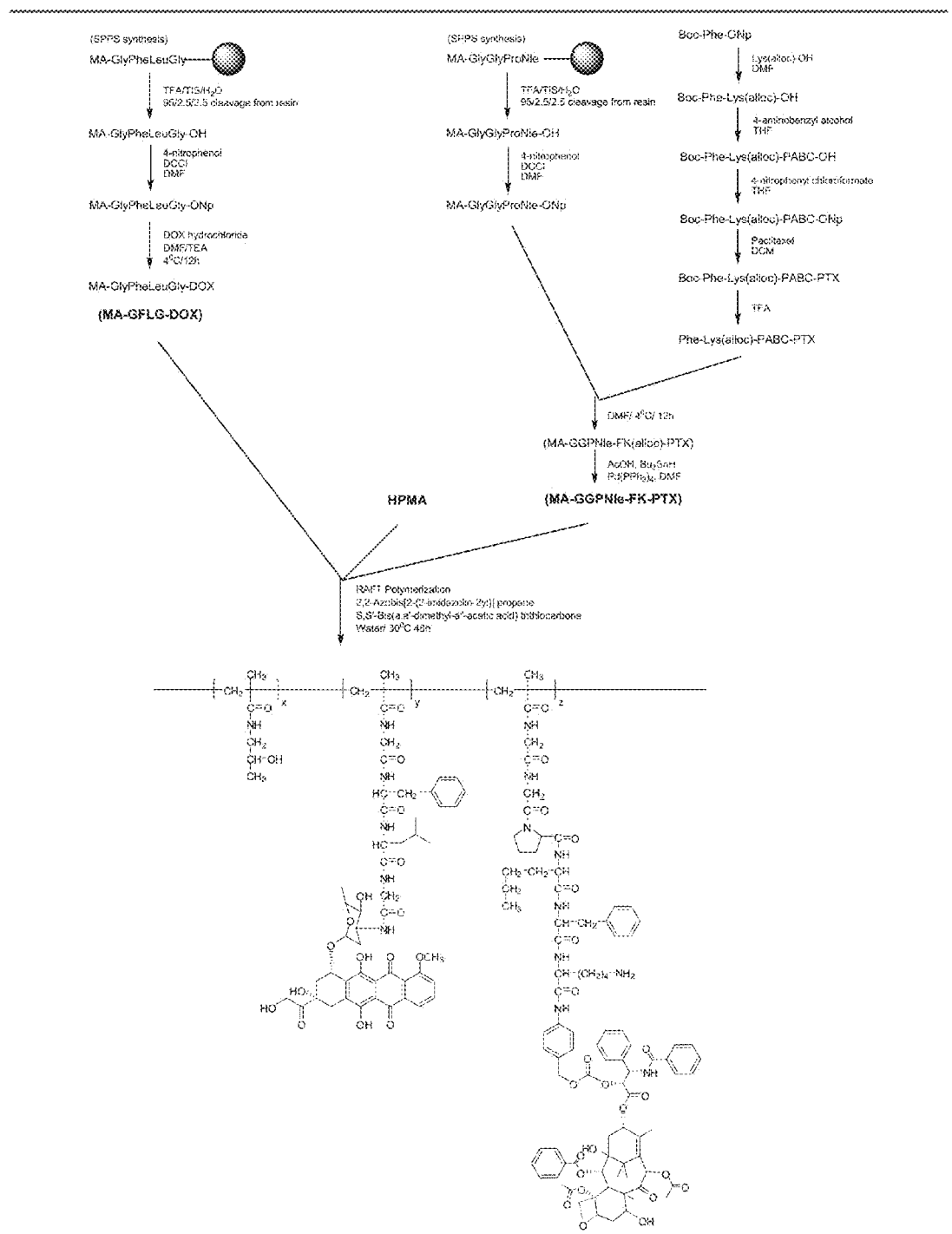
Figure 12E:
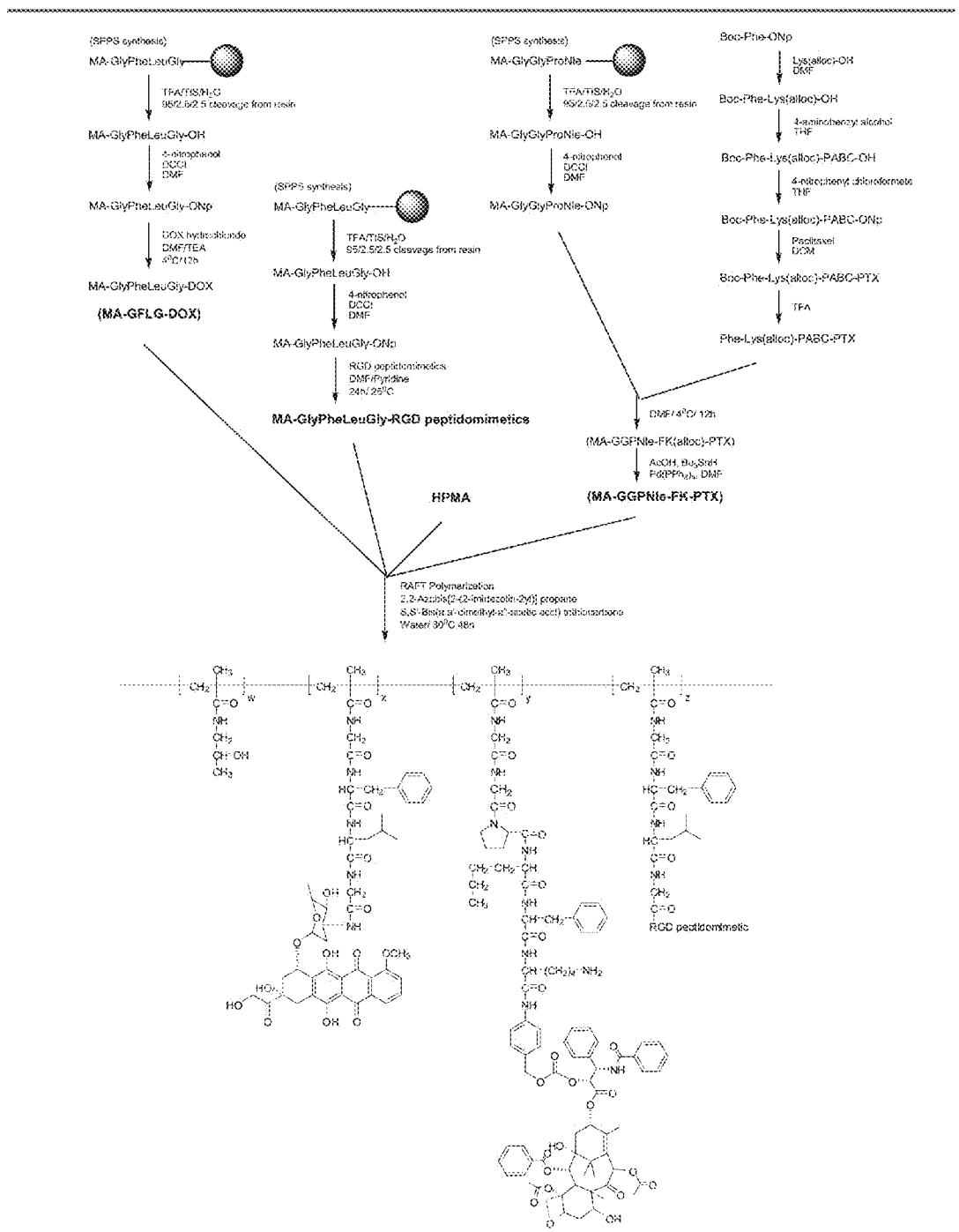
Figure 12F:
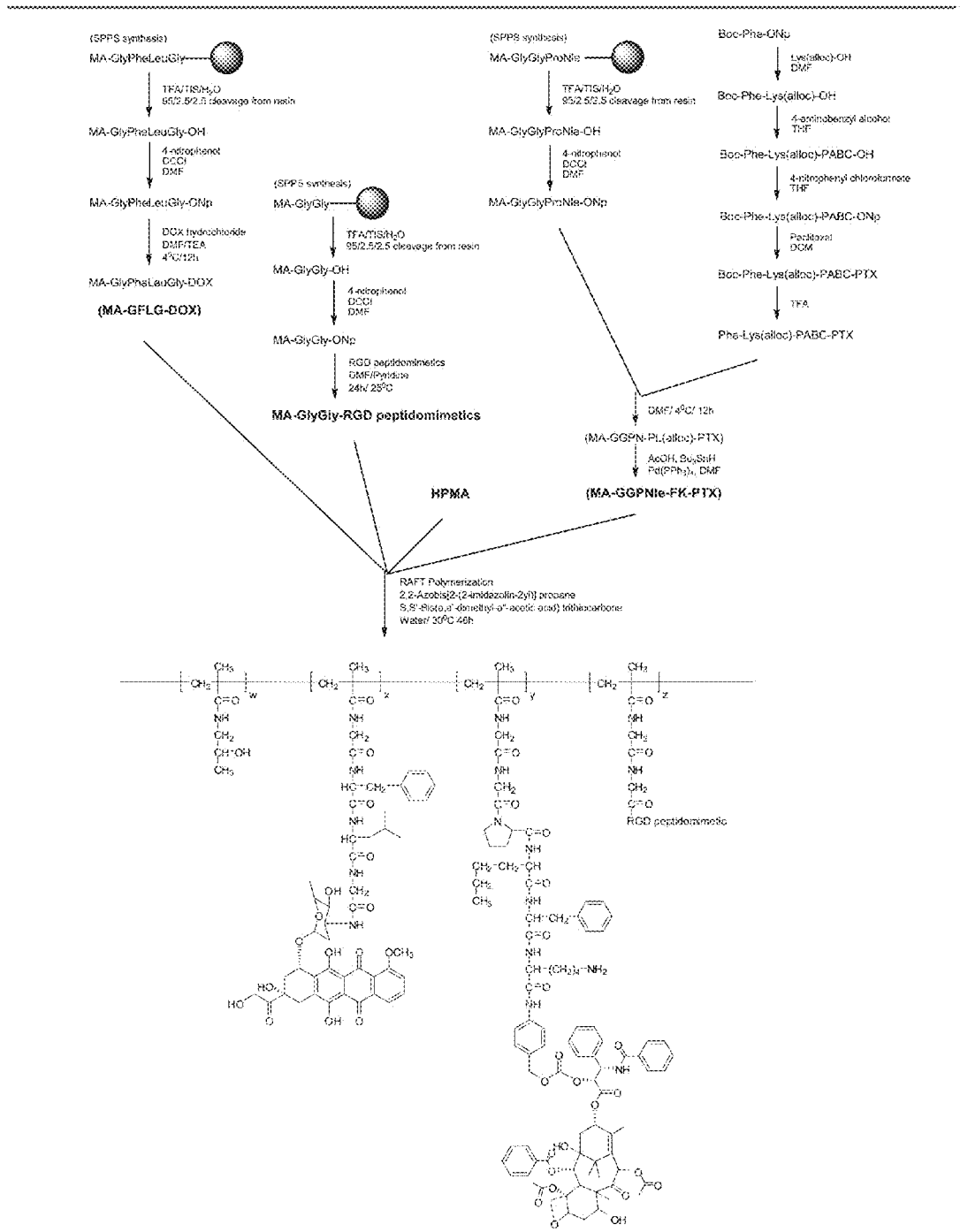
Figure 13A:
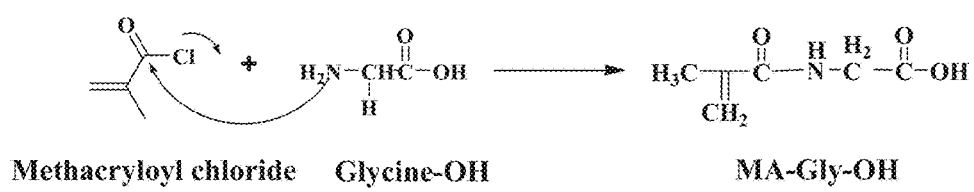
Figure 13B:
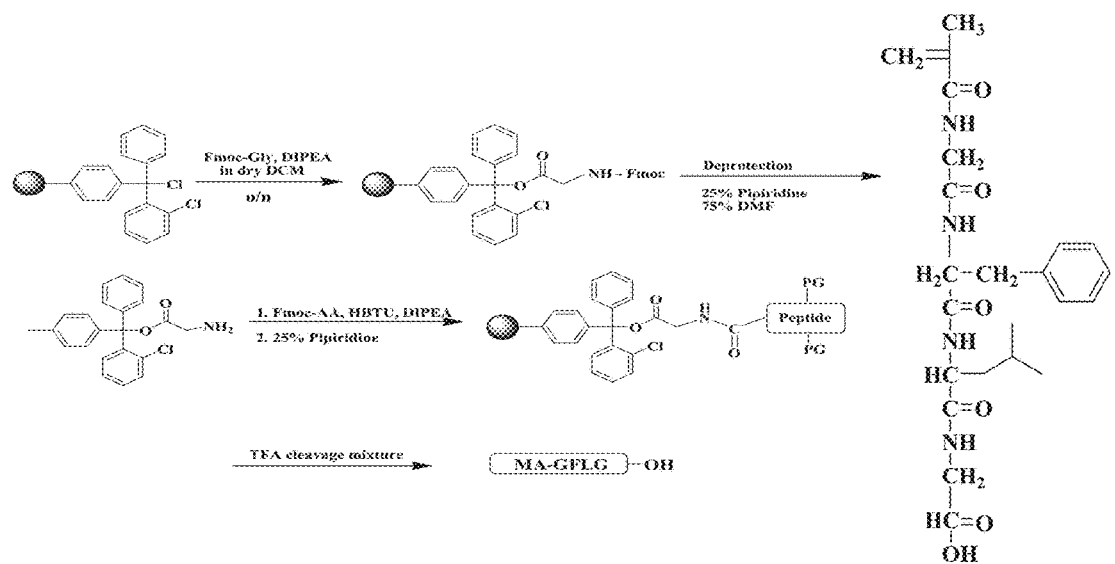
Figure 14A:
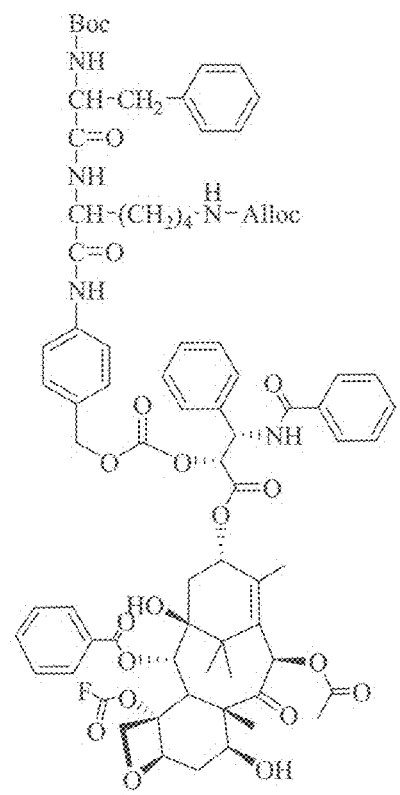
Figure 14B:
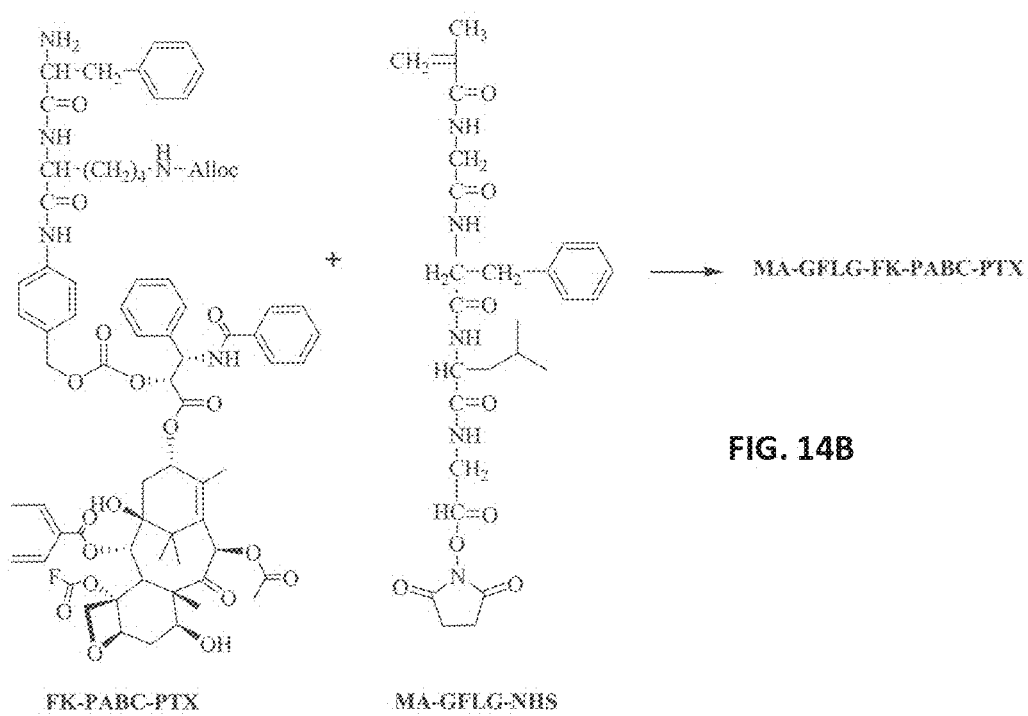
Figure 15:
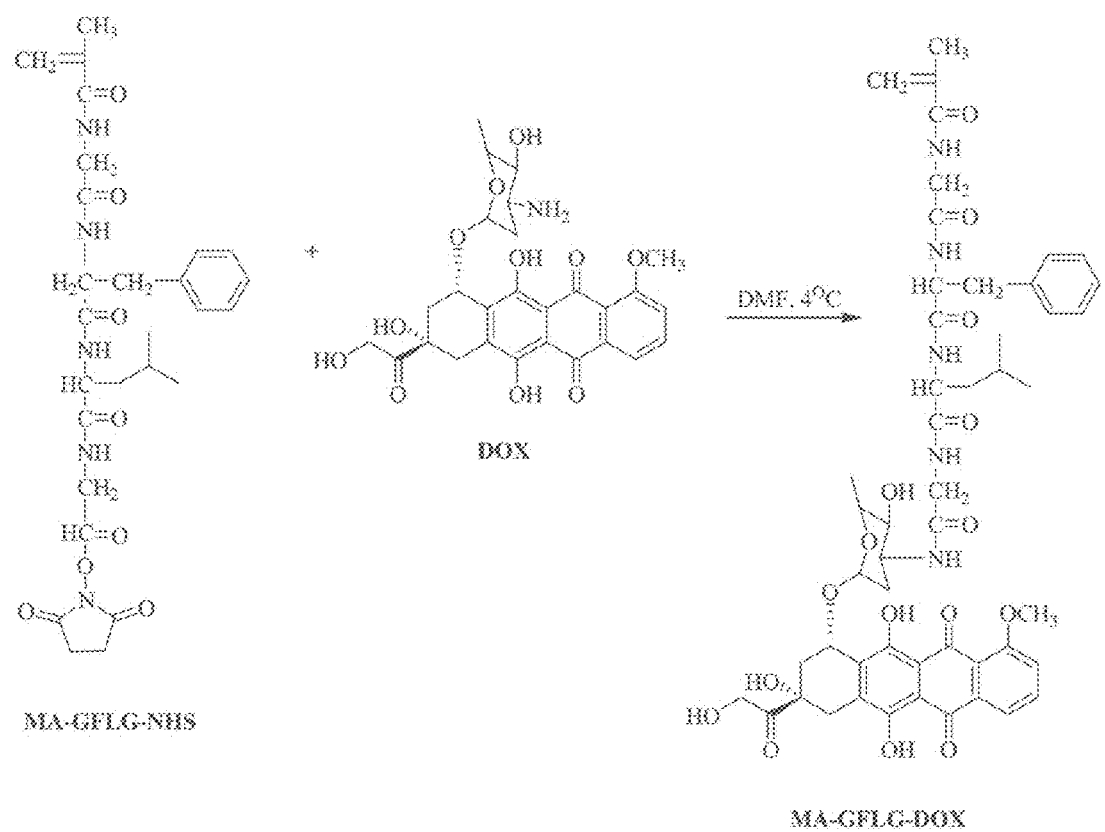
Figure 16A:
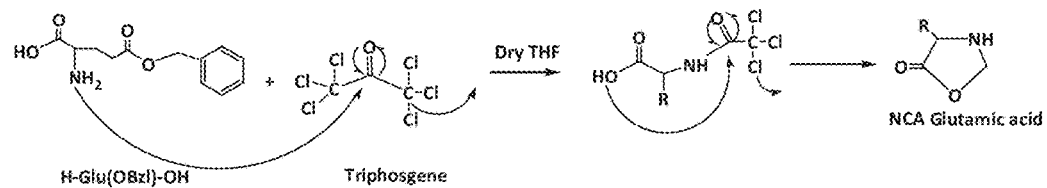
Figure 16B:
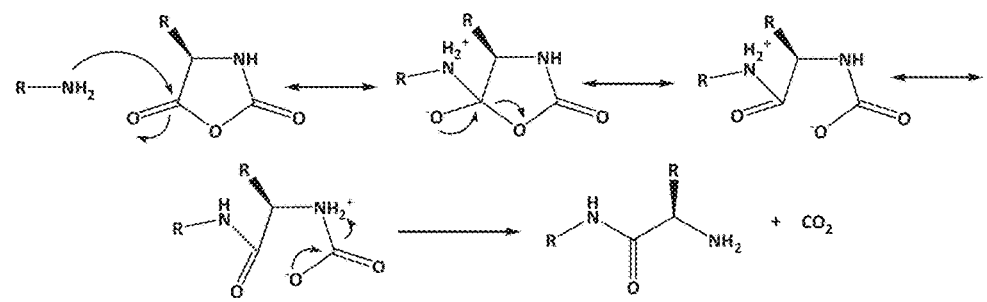
Figure 17:
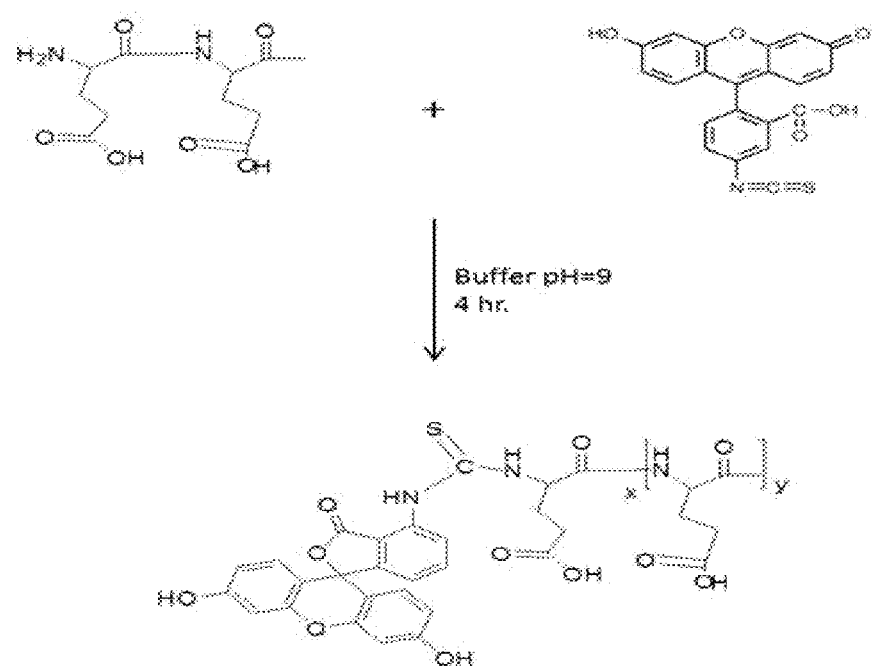
Figure 20A:
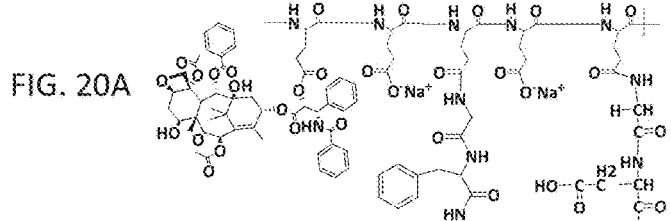
Figure 20B:
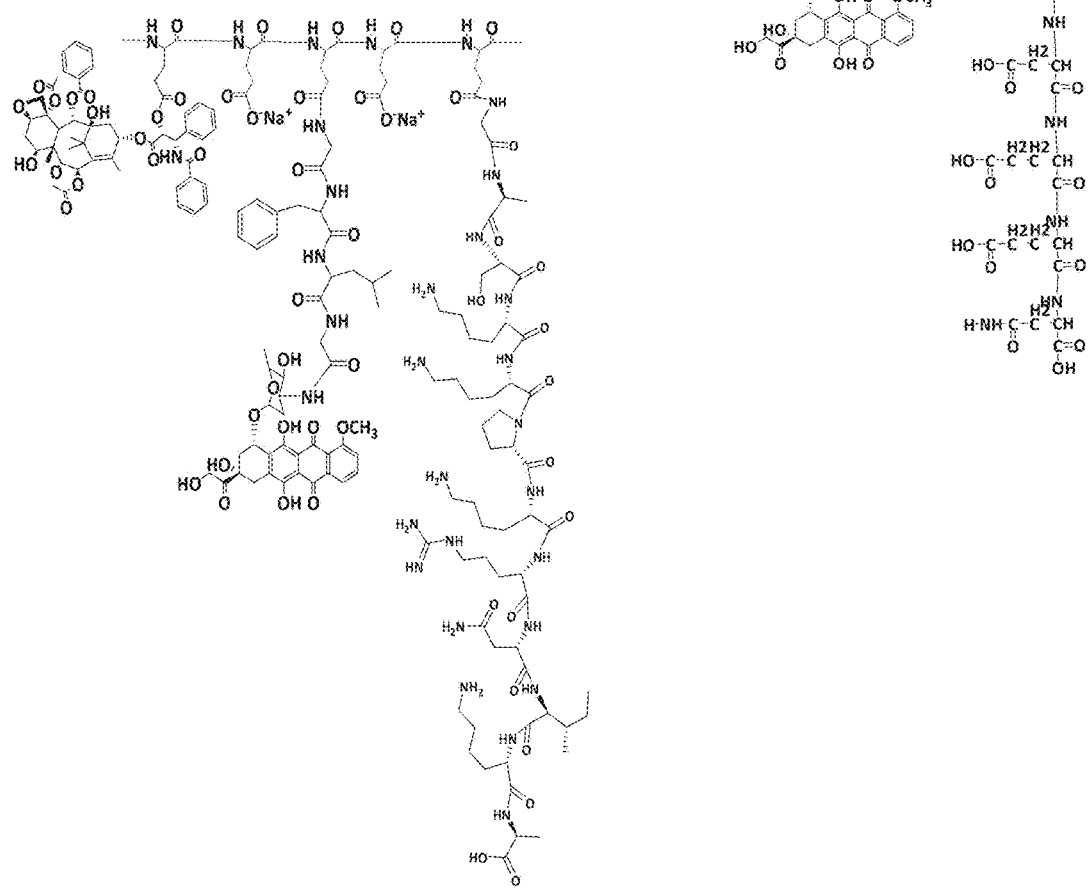
Figure 20C:
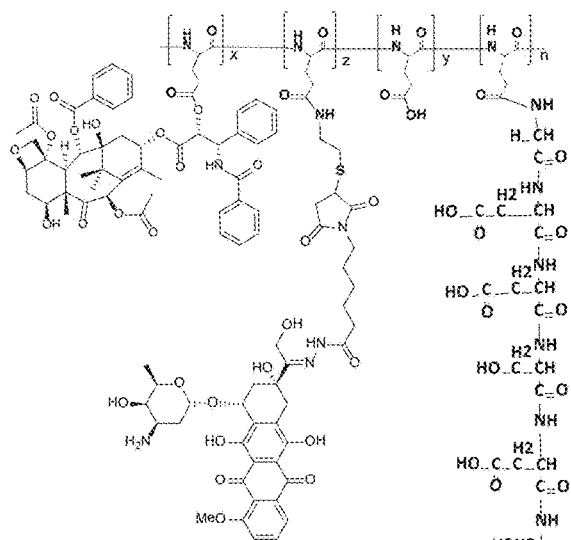
Figure 21:
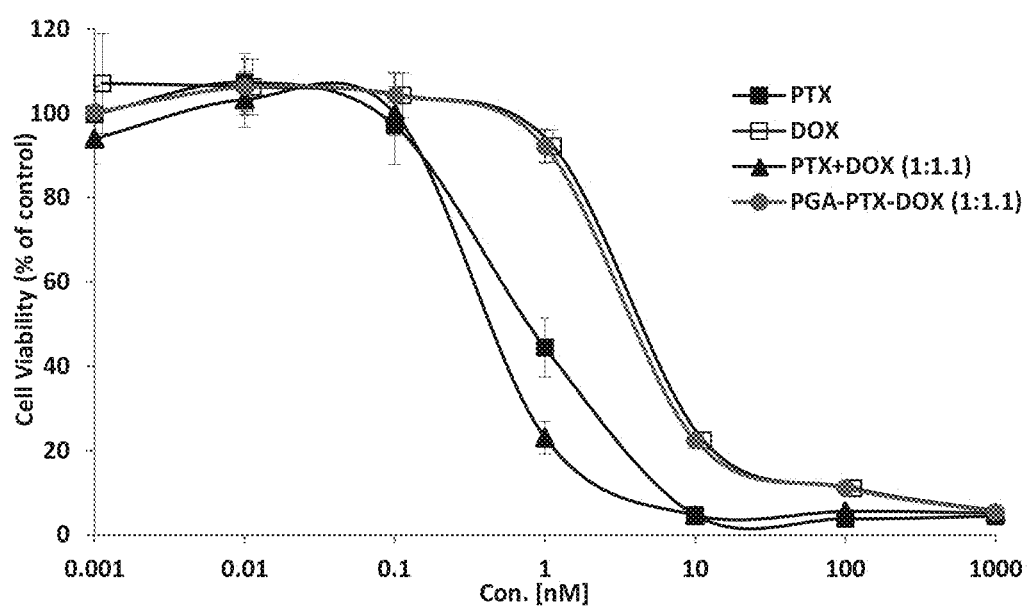
Figure 22A:
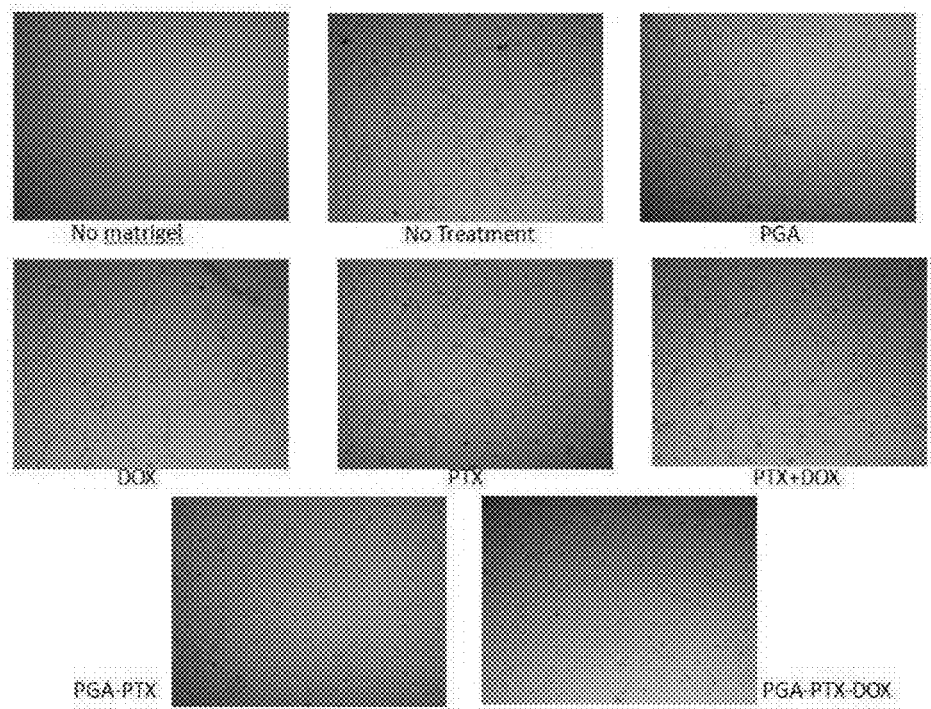
Figure 22B:
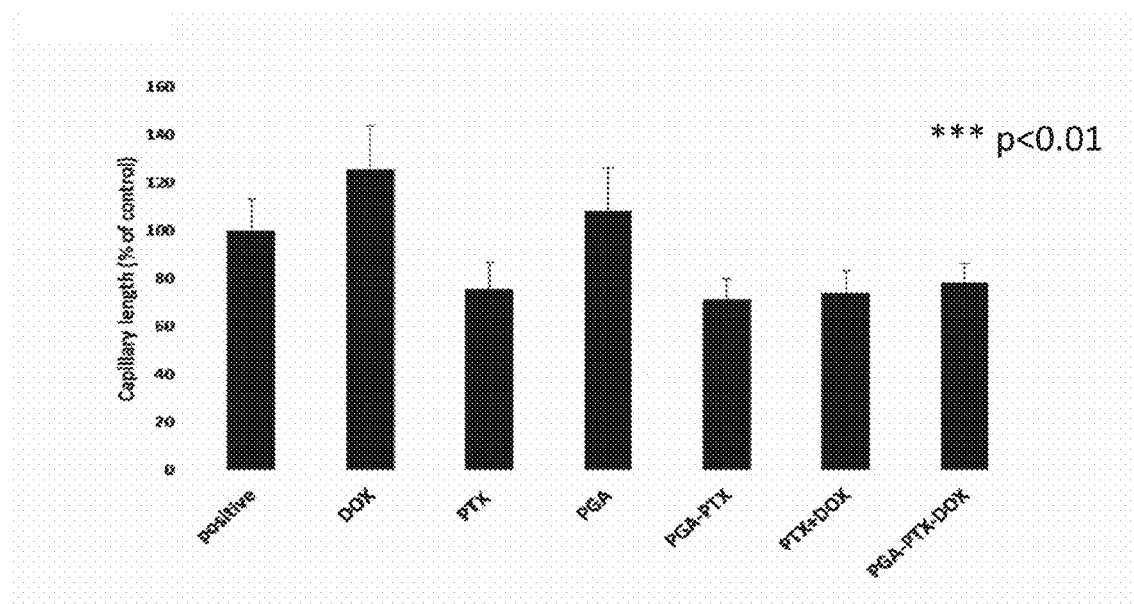
Figure 24:
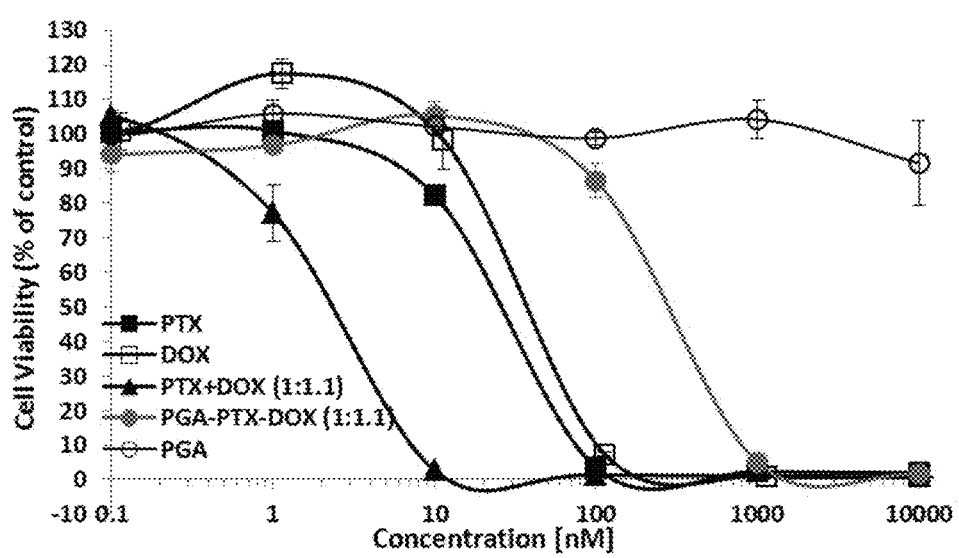
Figure 25:
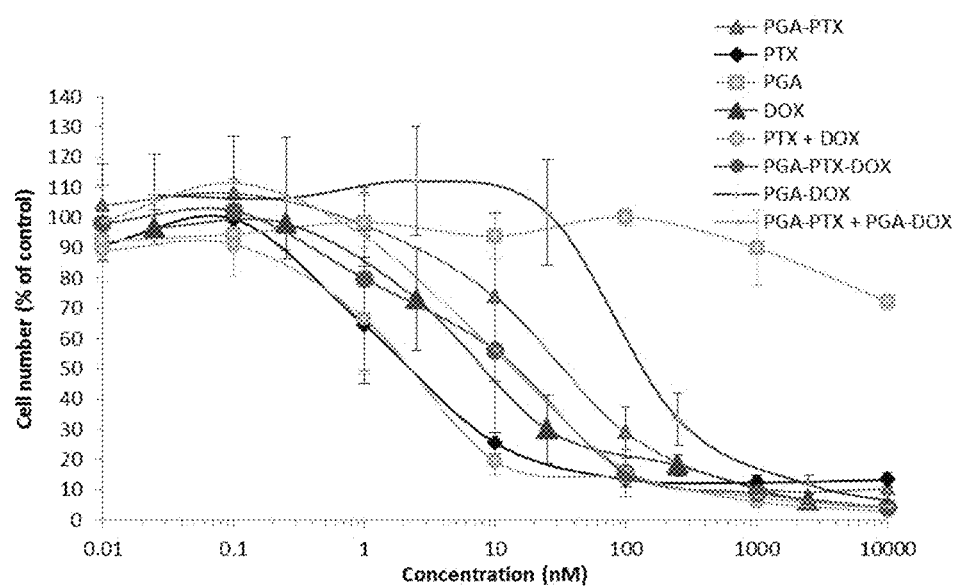
Figure 26:
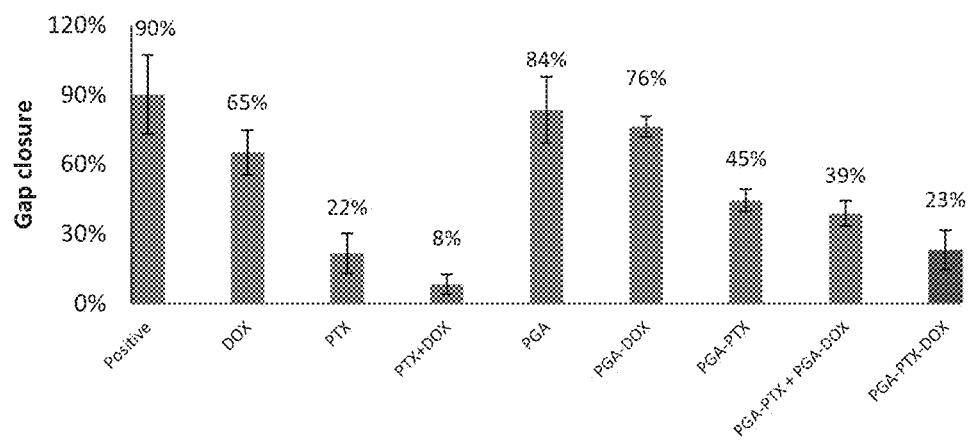
Figure 27:
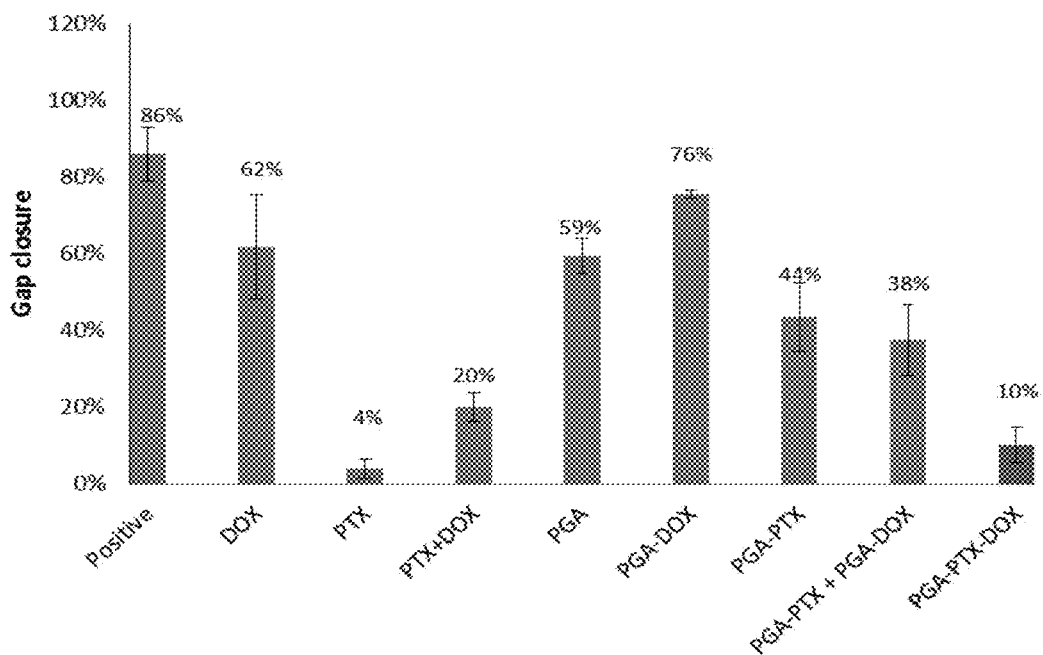
Figure 28:
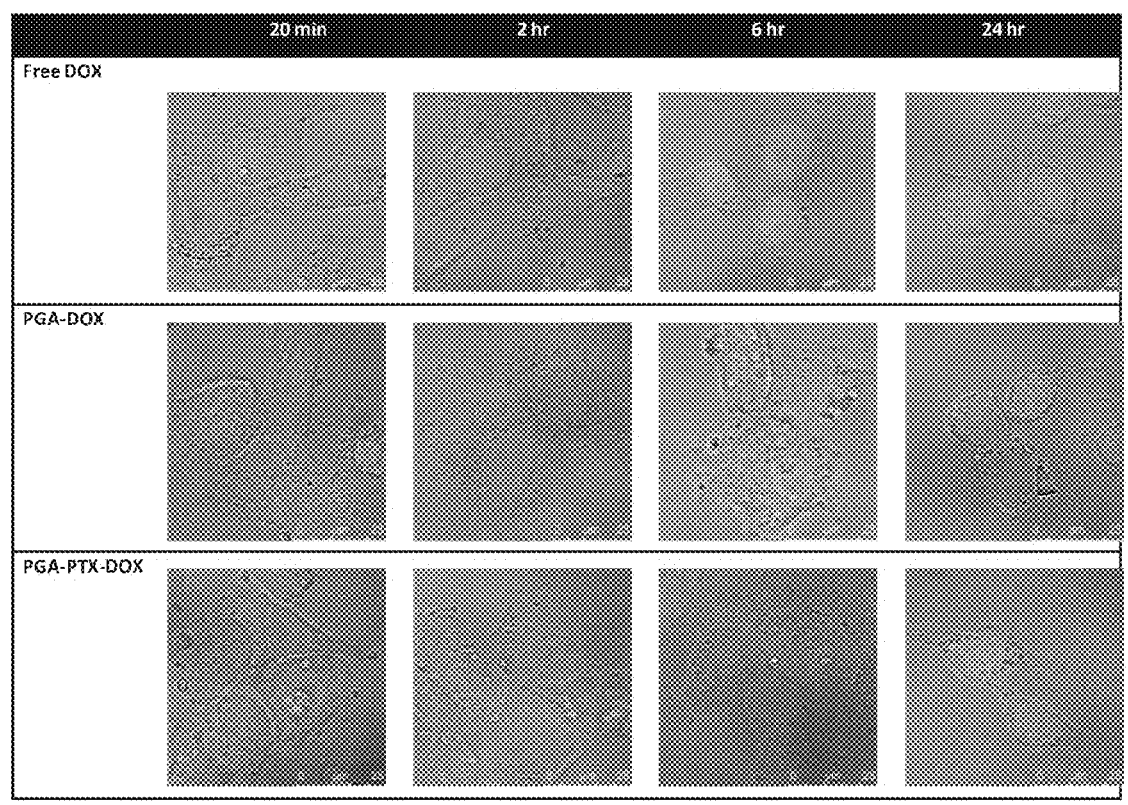
Figure 29A:
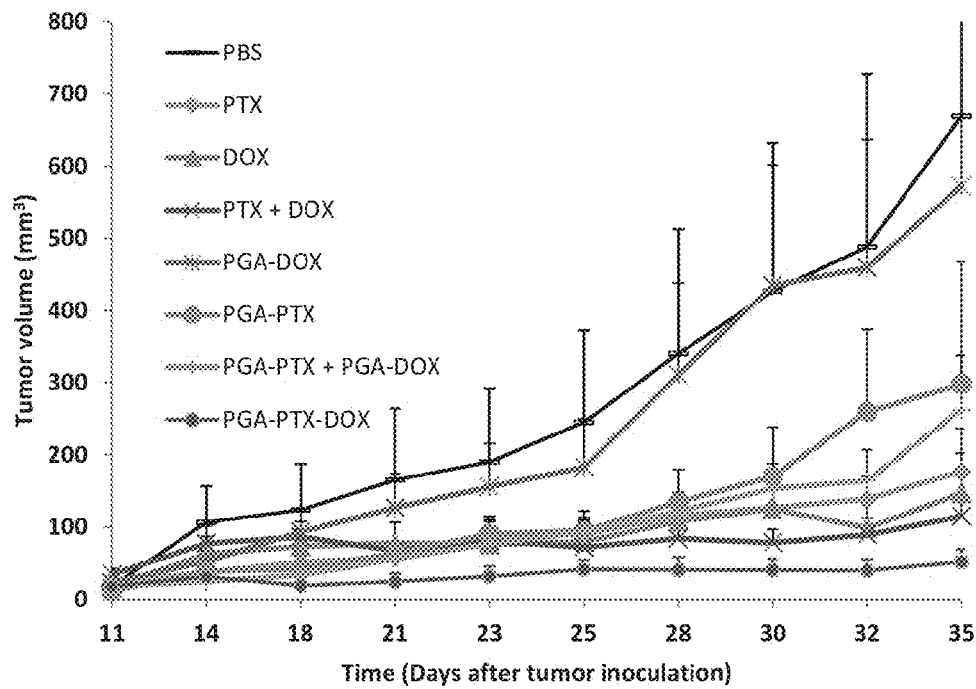
Figure 29B:
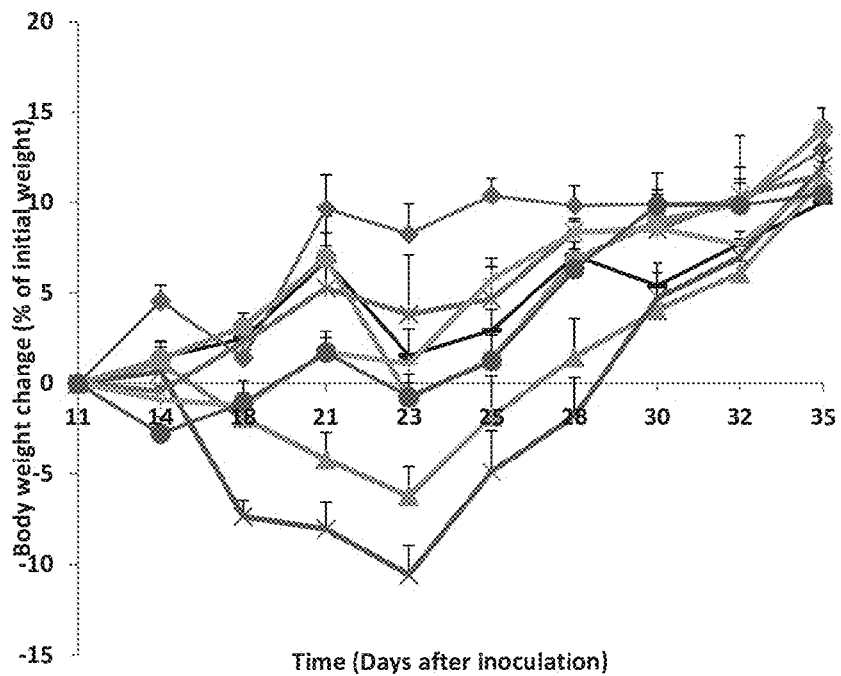
Figure 30:
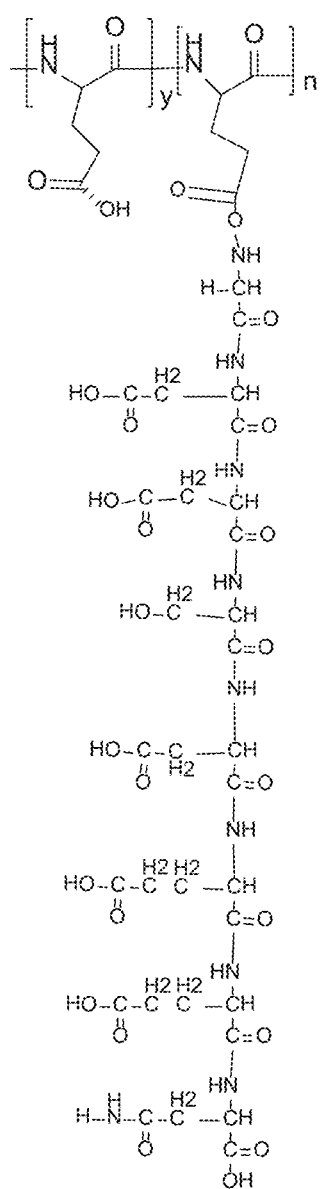
Figure 31:
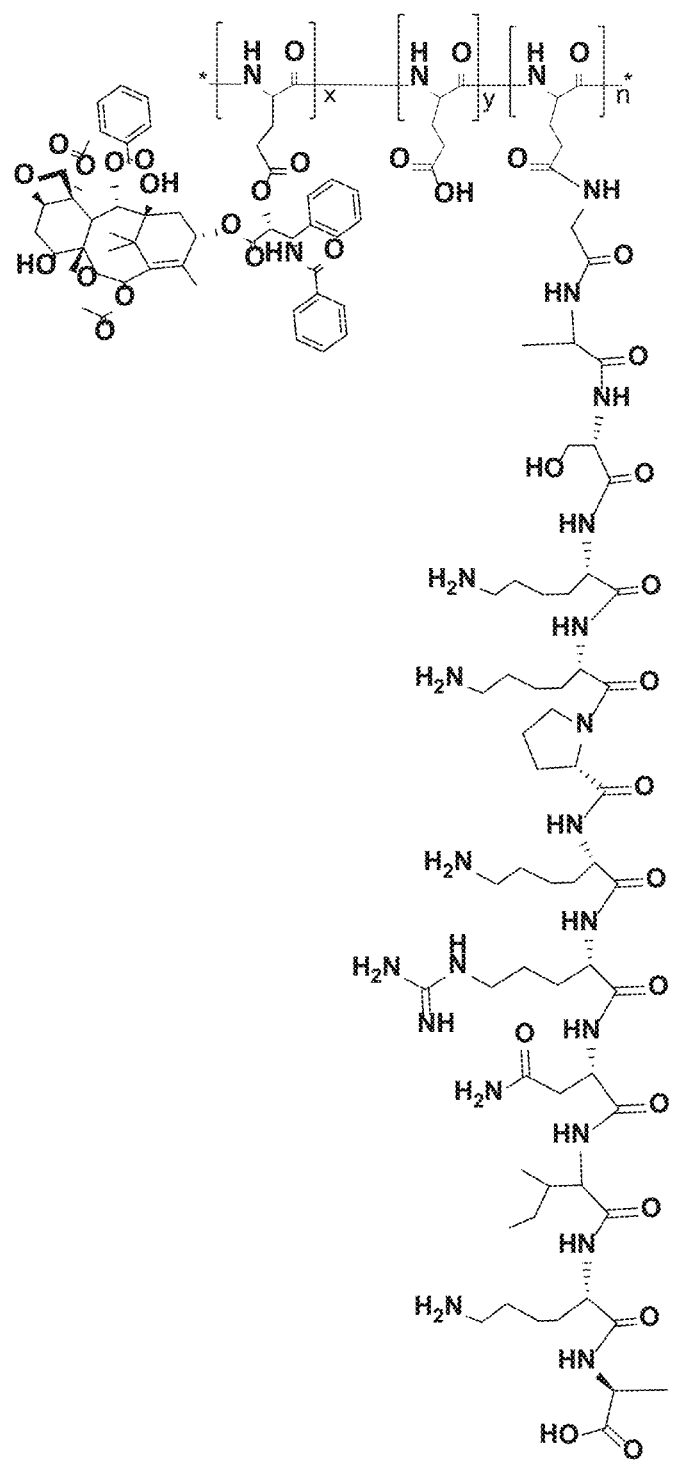
Figure 34:
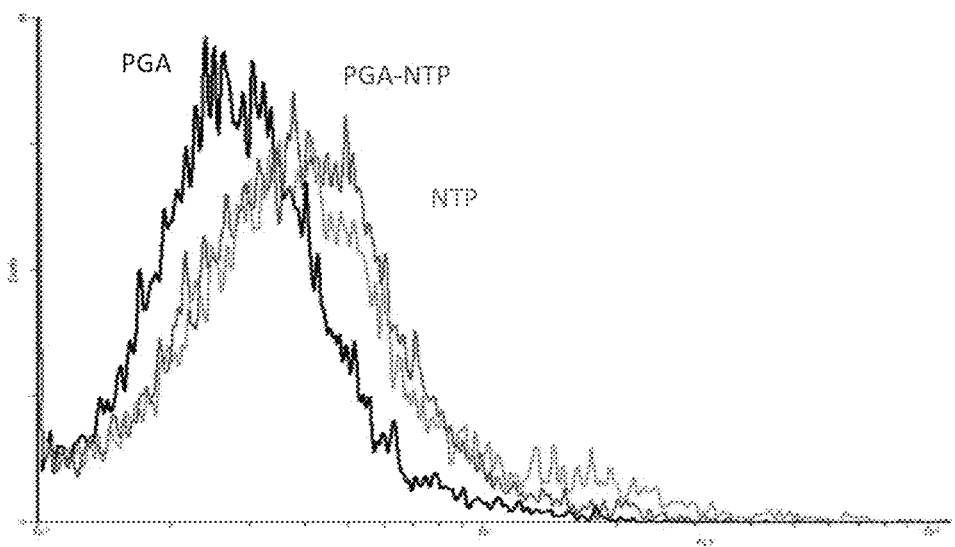
Figure 35:
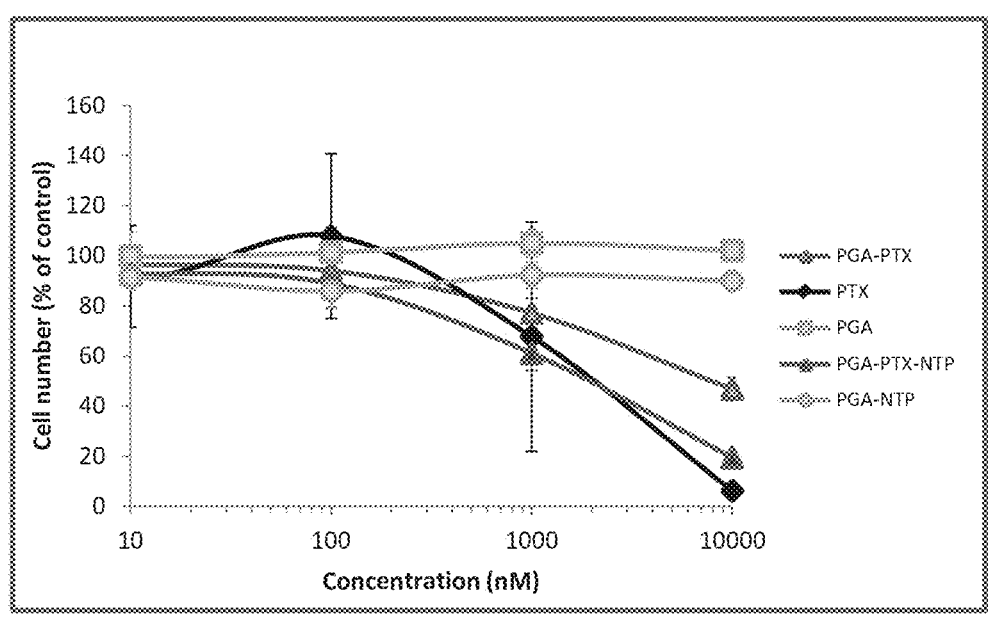
Figure 36:
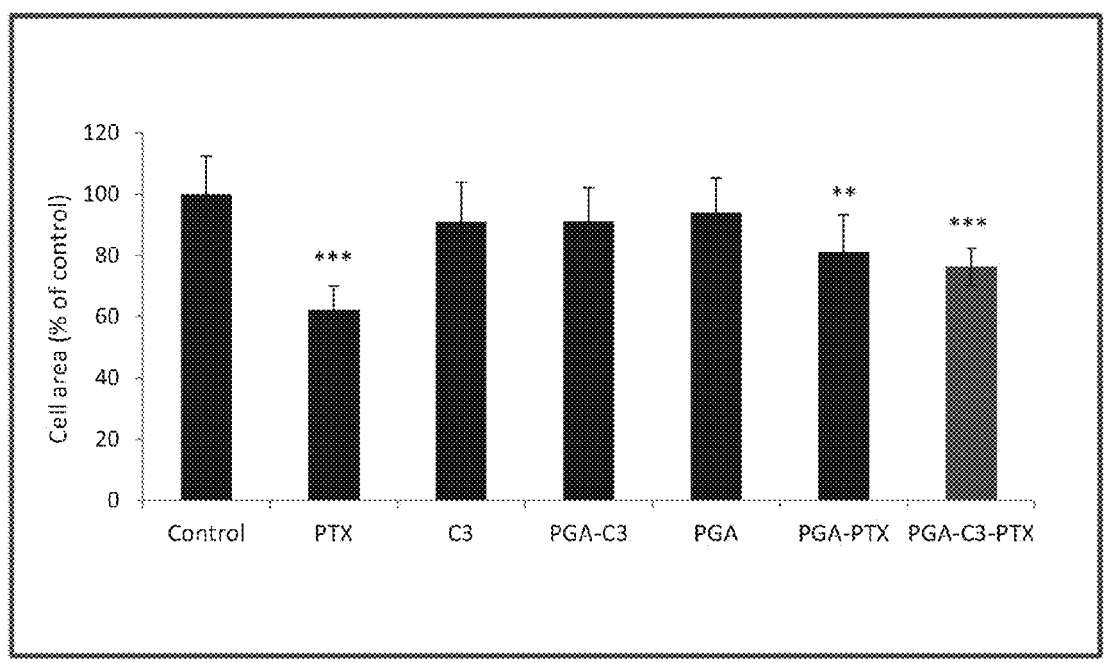

In the drawings:

FIGS. 1A-1B present the effect of PTX at various concentrations (FIG. 1A), and of doxorubicin at various concentrations (FIG. 1B) on the proliferation of HUVECs;

FIGS. 2A-2B present comparative plots showing the effect of PTX and DOX, each alone and in various combinations thereof, on the proliferation of HUVECs (FIG. 2A) and of HeLa HiFR cells (FIG. 2B);

FIGS. 3A-3B present the CI values and corresponding isobolograms demonstrating the synergistic effect exhibited by various combinations of PTX and DOX on HUVECs (FIG. 3A) and HeLa cells (FIG. 3B);

FIGS. 4A-4B present comparative plots showing the effect of PTX and DOX, each alone at various concentrations, and of a combination treatment of various concentrations of PTX and 50 nM DOX and of various concentrations of DOX and 50 nM PTX, on the viability of human ovarian carcinoma ES-2 cells (FIG. 4A), and isobolograms demonstrating the synergistic effect exhibited by the PTX and DOX combination on ES-2 cells (FIG. 4B);

FIGS. 5A-5B present comparative plots showing the effect of PTX and DOX, each alone at various concentrations, and of a combination treatment of various concentrations of PTX and 50 nM DOX, of various concentrations of PTX and 10 nM DOX, and of various concentrations of DOX and 1 nM PTX, on the viability of human osteosarcoma Saos-2 cells (FIG. 5A), and isobolograms demonstrating the synergistic effect exhibited by the PTX and DOX combination on Saos-2 cells (FIG. 5B);

FIGS. 6A-6B present comparative plots showing the effect of PTX and DOX, each alone at various concentrations, and of a combination treatment of various concentrations of PTX and 20 nM DOX, and of various concentrations of DOX and 1 nM PTX, on the viability of human MDA-MB-231 cells (FIG. 6A), and isobolograms demonstrating the synergistic effect exhibited by the PTX and DOX combination on human MDA-MB-231 cells (FIG. 6B);

FIGS. 7A-7B present comparative plots showing the effect of PTX and TNP-470, each alone and in various combinations thereof, on the proliferation of HUVECs, in the absence (FIG. 7A) and presence (FIG. 7B) of alendronate;

FIGS. 8A-8C present isobolograms calculated from $IC_{60}$ (FIG. 8A), $IC_{70}$ (FIG. 8B) and $IC_{90}$ (FIG. 8C) obtained for a combination treatment of PTX and TNP-470 on HUVECs;

FIG. 9 presents comparative plots showing the effect of PTX and TNP-470, each alone and in various combinations thereof, on the proliferation of DA3 cells;

FIG. 10 presents an exemplary isobologram demonstrating the synergistic/additive effect exhibited by a combination of PTX and TNP-470 on DA3 cells;

FIGS. 11A-11F present schematic illustrations of exemplary synthetic pathways and chemical structures of HPMA copolymer-(GGPNle)TNP-470-(GGPNle-FK)PTX conjugate (FIG. 11A), HPMA copolymer-(GGPNle)TNP-470-(GGPNle-FK)PTX-(GFLG)RGD conjugate (FIG. 11B), HPMA copolymer-(GGPNle)TNP-470-(GGPNle-FK)PTX-(GG)RGD conjugate (FIG. 11C), HPMA copolymer-(GFLG)TNP-470-(GGPNle-FK)PTX conjugate (FIG. 11D), HPMA copolymer-(GFLG)TNP-470-(GGPNle-FK)PTX-(GFLG)RGD conjugate (FIG. 11E) and HPMA copolymer-(GFLG)TNP-470-(GGPNle-FK)PTX-(GG)RGD conjugate (FIG. 11F);

FIGS. 12A-12F present schematic illustrations of exemplary synthetic pathways and chemical structures of HPMA copolymer-(GGPNle)DOX-(GGPNle-FK)PTX conjugate (FIG. 12A), HPMA copolymer-(GGPNle)DOX-(GGPNle-FK)PTX-(GFLG)RGD conjugate (FIG. 12B), HPMA copolymer-(GGPNle)DOX-(GGPNle-FK)PTX-(GG)RGD conjugate (FIG. 12C), HPMA copolymer-(GFLG)DOX-(GGPNle-FK)PTX conjugate (FIG. 12D), HPMA copolymer-(GFLG)DOX-(GGPNle-FK)PTX-(GFLG)RGD conjugate (FIG. 12E), and HPMA copolymer-(GFLG)DOX-(GGPNle-FK)PTX-(GG)RGD conjugate (FIG. 12F);

FIGS. 13A-13B present schematic illustrations of the syntheses and chemical structures of exemplary MA monomeric units having a Gly linker attached thereto (FIG. 13A) and a GFLG linker (FIG. 13B), according to some embodiments of the present invention;

FIGS. 14A-14B present schematic illustrations of the chemical structure of a BOC-protected FK linker conjugates to PTX, obtained by coupling PTX to FK linker via p-aminobenzylalcohol (PABA) (FIG. 14A) and the coupling of PTX to the MA-GFLG described in FIG. 13B to thereby obtain an exemplary MA monomeric unit having PTX attached thereto according to some embodiments of the present invention;

FIG. 15 presents schematic illustration of the chemical structure and synthesis of An exemplary monomeric MA unit having attached thereto DOX, obtained by coupling DOX to the activated MA-GFLG monomeric unit presented in FIG. 13B, according to some embodiments of the present invention;

FIGS. 16A-16B present a schematic illustration of an exemplary synthesis of PGA, by synthesis of NCA glutamic acid from a protected glutamic acid (the γCOOH is protected with OBzl) (FIG. 16A), following by polymerization of the NCA monomer (FIG. 16B, exemplifying the First step of polymerization);

FIG. 17 presents a schematic illustration of an exemplary synthetic pathway for conjugating FITC to PGA, via formation of a thiourea bond between FITC and the N-terminal amine of PGA;

FIG. 18 presents a schematic illustration of a chemical structure of an exemplary conjugate PGA-PTX-DOX, in which PTX is bound to the PGA polymeric backbone via a hydrolysable ester bond and DOX is bound to the PGA backbone via cathepsin B-cleavable GFLG linker;

FIGS. 19A-19D present a schematic illustration of a synthetic pathway for preparing another exemplary PDA-PTX-DOX conjugate, in which PTX is bound to the PGA polymeric backbone via a hydrolysable ester bond and DOX is bound to the PGA backbone via an acid-sensitive hydrazone linker;

FIGS. 20A-20D present schematic illustrations of the chemical structures of exemplary PGA-PTX-DOX conjugates having the NCAM targeting peptide NTP (FIGS. 20A and 20C) and C3 peptide (FIGS. 20B and 20D) attached to some of the PGA backbone units, in which DOX is attached to the PGA backbone units via a GFLG linker (FIGS. 20A and 20B) or via a hydrazone linker (FIGS. 20C and 20 D);

FIG. 21 presents comparative plots showing the effect of an exemplary PGA-PTX-DOX conjugate (depicted in FIG. 18) and of the free drugs, each alone and in combination, on the proliferation of HUVECs (Data represents mean±SD);

FIGS. 22A-22B present representative images (FIG. 22A) and a bar graph (FIG. 22B) showing the effect of a PGA-PTX-DOX conjugate (depicted in FIG. 18), compared to controls, on capillary-like tube formation in HUVECs;

FIGS. 23A-23B present comparative plots demonstrating the effect of exemplary PGA-PTX-DOX conjugates (a conjugate as depicted in FIG. 18 in FIG. 23A and a conjugate as depicted in FIG. 19D in FIG. 23B) and control conjugates, free drugs and polymer, on proliferation of ES-2 cells, following 72 hours incubation (Data represents mean±SD);

FIG. 24 presents comparative plots demonstrating the effect of an exemplary PGA-PTX-DOX conjugate (as depicted in FIG. 18) and control conjugates, free drugs and polymer, on proliferation of murine 4T1 cells, following 72 hours incubation (Data represents mean±SD);

FIG. 25 presents comparative plots demonstrating the effect of an exemplary PGA-PTX-DOX conjugate (depicted in FIG. 19D) and control conjugates, free drugs and polymer, on proliferation of MDA-MB-231 cells, following 72 hours incubation (Data represents mean±SD);

FIG. 26 presents bar graph showing the effect of PGA-PTX-DOX conjugate (depicted in FIG. 19D) and control conjugates, free drugs and polymer, on migration of ES-2 cells, as seen in a scratch assay, following 17 hours incubation;

FIG. 27 presents bar graph showing the effect of PGA-PTX-DOX conjugate (depicted in FIG. 19D) and control conjugates, free drugs and polymer, on migration of MDA-MB-231 cells, as seen in a scratch assay, following 24 hours incubation;

FIG. 28 presents confocal microscopy images showing internalization of DOX to MDA-MB-231 cells, following 24 hours incubation with free DOX, PGA-DOX and PGA-DOX-PTX, at 400 nM equivalent DOX-concentrations, wherein nuclear stain (DAPI) shown in blue, DOX shown in red and colocalization (DOX in the nucleus) shown in purple, and colocalization of DAPI and DOX is shown at the different time points;

FIGS. 29A-29B present comparative plots showing the effect of treatment with PGA-PTX-DOX conjugate (depicted in FIG. 19D) and control conjugates, free drugs and vehicle (PBS) on tumor volume (FIG. 29A) and body weight (FIG. 29B) on mice inoculated with MDA-MB-231 cancer cells;

FIG. 30 presents the chemical structure of an exemplary conjugate according to some embodiments of the present invention, comprising PGA having attached thereto the NCAM targeting moiety having SEQ ID NO:1 (a PGA-NTP conjugate);

FIG. 31 presents the chemical structure of an exemplary conjugate according to some embodiments of the present invention, comprising PGA having attached thereto the NCAM targeting moiety having SEQ ID NO:3 (a PGA-PTX-C3 conjugate);

FIGS. 32A-32D present confocal microscopy images of Saos2 cells (control; FIG. 32A), of Saos-2 cells stained with fluorescein-labeled NTP (SEQ ID NO:1) in full medium, Saos-2 cells stained with NTP (SEQ ID NO:1)+transferrin in serum free medium (FIG. 32C) and of Saos-2 cells stained with scrambled NTP sequence (sNTP) (SEQ ID NO:2)+ transferrin in serum free medium (FIG. 32D) [Blue: Hoecst (nuclei), green: CF (peptides), red: Alexa Fluor 555 (transferrin)];

FIG. 33 presents images of FACS analysis demonstrating the binding of the NCAM targeting peptide C3 (SEQ ID NO:3) and of NCAM-specific antibody (coupled to Allophycocyanin (APC) dye) to ES2 cells. X axis: green (CF), Y axis: red (antibody coupled to Allophycocyanin (APC) dye);

FIG. 34 presents data obtained by FACS analysis for PGA-C3 binding to NCAM-expressing ES-2 cells (red), compared to non-targeted PGA (black) and free C3 peptide (green);

FIG. 35 presents comparative plots showing the effect of the conjugate PGA-C3-PTX and of the free components and control conjugates on the proliferation of ES-2 cells; and FIG. 36 is a bar graph showing the effect of the conjugate PGA-C3-PTX and of the free components and control conjugates on capillary-like tubes formation of HUVECs.

DESCRIPTION OF SPECIFIC EMBODIMENTS
OF THE INVENTION

The present invention, in some embodiments thereof, relates to chemical conjugates and to uses thereof and, more particularly, but not exclusively, to polymeric conjugates having attached thereto a therapeutically active agent and an additional therapeutically active agent and/or a targeting moiety, to processes of preparing such conjugates and to uses thereof.

The principles and operation of the conjugates, compositions, use, methods and processes according to the invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

A polymeric drug delivery system can be designed for passive or active targeting. Passive targeting refers to the exploitation of the natural (passive) distribution pattern of a drug-carrier in vivo. The latter is based upon the phenomenon named the "enhanced permeability and retention (EPR) effect", and is attributed to two factors: (I) the disorganized pathology of the angiogenic tumor vasculature with its discontinuous endothelium, leading to hyperpermeability to circulating macromolecules, and (II) the lack of effective tumor lymphatic drainage, which leads to subsequent macromolecular accumulation. The active approach relies upon the selective localization of a ligand at a cell-specific receptor.

A well-designed polymeric drug delivery system, whether it is targeting the tumor site passively or actively, improves the therapeutic index of anti-angiogenic agents by increasing the half-life of low molecular weight drugs, their water-solubility and their time of exposure to the tumor vasculature (i.e. to the tumor endothelial cells), while reducing their toxicity.

Attachment of drugs to polymeric carriers typically imparts: limited cellular uptake to the endocytic route; long-circulation conjugates (e.g., minutes vs. hours); improved drug targeting to the tumor; reduce drug toxicity; and overcoming the mechanisms of drug resistance.

Design of polymer-drug conjugate is typically made as follows: polymer should be non-toxic & non-immunogenic; molecular weight should be less than 60,000 grams/mol, preferably less than 40,000 grams/mol, if the polymer is not biodegradable; conjugate should improve drug targeting to the tumor; conjugate should have adequate drug payload; polymer-drug linker must be stable during transport to the tumor; access to the correct intracellular compartment is essential.

Coupling the conjugates to targeting ligands further promotes increased tumor targeting by receptor mediated delivery.

Due to the molecular complexity of many diseases, combination therapy is becoming increasingly important. Unlike single-agent therapy, multi-agent therapy can modulate different signaling pathways in diseased cells, maximizing the therapeutic effect and, possibly, overcoming mechanisms of resistance. Whereas chemotherapy drugs are normally associated with severe side-effects, administration of a combination of agents hitting different targets and displaying different toxicity profiles can improve the therapeutic index either in the form of better efficacy or in the form of comparable efficacy and reduced toxicity. If two agents that act synergistically are combined, lower concentrations of each agent can be administered, increasing their combined antitumor efficacy and decreasing their toxicity and side effects. Polymeric systems are an ideal platform for true combination therapy, where the therapeutics are given simultaneously in one injection and share the same pharmacokinetic profile (Greco et al., Adv Drug Deliv Rev, 2009. 61(13): p. 1203-13).

The present inventors have now devised and successfully prepared and practiced novel conjugates of a copolymer having attached thereto one or more therapeutically active agent(s), optionally in combination with a ligand of a cell-surface receptor.

According to an aspect of some embodiments of the present invention there is provided a polymeric conjugate comprising a polymeric backbone having attached thereto two or more therapeutically active agent(s).

In some embodiments, such a polymer further comprises and a targeting moiety such as, for example, a ligand of a cell-surface receptor.

According to an aspect of some embodiments of the present invention there is provided a polymeric conjugate comprising a polymeric backbone having attached thereto one or more therapeutically active agent(s) and a targeting moiety, wherein the targeting moiety is a ligand of the cell-surface receptor neural cell adhesion molecule (NCAM).

As used herein throughout, the term "polymer" describes an organic substance composed of a plurality of repeating structural units (backbone units) covalently connected to one another. The term "polymer" as used herein encompasses organic and inorganic polymers and further encompasses one or more of a homopolymer, a copolymer or a mixture thereof (a blend). The term "homopolymer" as used herein describes a polymer that is made up of one type of monomeric units and hence is composed of homogenic backbone units. The term "copolymer" as used herein describes a polymer that is made up of more than one type of monomeric units and hence is composed of heterogenic backbone units. The heterogenic backbone units can differ from one another by the pendant groups thereof.

Polymers which are suitable for use in the context of the present embodiments are biocompatible, non-immunogenic and non-toxic. The polymers serve as carriers that enable specific delivery into tumor tissue. As described hereinabove, the specific delivery is due to the enhanced permeability and retention (EPR) effect discussed hereinabove. Furthermore, conjugation to polymers may restrict the passage through the blood brain barrier and may prolong the circulating half-life of the drugs, hence inhibiting the growth of tumor endothelial and epithelial cells by exposing the cells to the conjugated drugs in the circulation for a longer time compared to the free drugs. Additionally, polymer-drug conjugates may act as drug depots for sustained release, producing prolonged drug exposure to tumor cells. Water soluble polymers may be used to stabilize drugs, as well as to solubilize otherwise insoluble compounds such as, for example, TNP-470 and Paclitaxel.

A polymer from which the polymeric backbone of the polymeric conjugate described herein is derived, or corresponds to, as discussed hereinafter, may be a biostable polymer, a biodegradable polymer or a combination thereof.

The term "biostable", as used in this context of embodiments of the invention, describes a compound or a polymer that remains intact under physiological conditions (e.g., is not degraded in vivo).

The term "biodegradable" describes a substance which can decompose under physiological and/or environmental conditions into breakdown products. Such physiological and/or environmental conditions include, for example, hydrolysis (decomposition via hydrolytic cleavage), enzymatic catalysis (enzymatic degradation), and mechanical interactions. This term typically refers to substances that decompose under these conditions such that 50 weight percents of the substance decompose within a time period shorter than one year.

The term "biodegradable" as used in the context of embodiments of the invention, also encompasses the term "bioresorbable", which describes a substance that decomposes under physiological conditions to break down products that undergo bioresorption into the host-organism, namely, become metabolites of the biochemical systems of the host-organism.

The polymers can be water-soluble or water-insoluble. In some embodiments, the polymers are water soluble at room temperature.

The polymers can further be charged polymers or non-charged polymers. Charged polymers can be cationic polymers, having positively charged groups and a positive net charge at a physiological pH; or anionic polymers, having negatively charged groups and a negative net charge at a physiological pH. Non-charged polymers can have positively charged and negatively charged group with a neutral net charge at physiological pH, or can be non-charged.

In some embodiments, the polymer has an average molecular weight in the range of 100 Da to 800 kDa. In some embodiments, the polymer has an average molecular weight lower than 60 kDa. In some embodiments, the polymer's average molecular weight range is 15 to 60 kDa.

Polymeric substances that have a molecular weight higher than 10 kDa typically exhibit an EPR effect, as described herein, while polymeric substances that have a molecular weight of 100 kDa and higher have relatively long half-lives in plasma and an inefficient renal clearance. Accordingly, a molecular weight of a polymeric conjugate can be determined while considering the half-life in plasma, the renal clearance, and the accumulation in the tumor of the conjugate.

The molecular weight of the polymer can be controlled, at least to some extent, by the degree of polymerization (or co-polymerization).

The polymer used in the context of embodiments of the invention can be a synthetic polymer or a naturally-occurring polymer. In some embodiments, the polymer is a synthetic polymer.

The polymeric backbone of a polymeric conjugate as described herein may be derived from, or correspond to a polymeric backbone of polymers such as, for example, polyacrylates, polyvinyls, polyamides, polyurethanes, polyimines, polysaccharides, polypeptides, polycarboxylates, and mixtures thereof.

Exemplary polymeric backbones which are suitable for use in the context of the present embodiments are polymeric backbones which correspond to the polymeric backbones of polymers such as, but are not limited to, polyglutamic acid (PGA), a poly(hydroxyalkylmethaacrylamide) (HPMA), a polylactic acid (PLA), a polylactic-co-glycolic acid (PLGA), a poly(D,L-lactide-co-glycolide) (PLA/PLGA), a polyamidoamine (PAMAM), a polyethylenimine (PEI), dextran, pollulan, a water soluble polyamino acid, a polyethylenglycol (PEG).

These polymers can be of any molecular weight, as described herein, and preferably have a molecular weight within the range of 10 to 60 kDa, or of 10 to 40 kDa.

It is to be understood that the polymers as discussed herein describe those polymers that are formed from homogenic or heterogenic, non-functionalized monomeric units, and that the polymeric backbone constituting the polymeric conjugate disclosed herein corresponds to such polymers by being comprised of the same monomeric units, while some of these monomeric backbone units have moieties attached thereto, as described herein. Thus, the polymeric backbone of the polymeric conjugate is similar to that of the polymers described herein, and differs from the polymers by having the above-described agents attached to some of the backbone units therein.

In some of any of the embodiments described herein, the polymeric backbone of the conjugate corresponds to (as described herein), or is derived from (as described herein, a polymeric backbone of a poly(hydroxyalkylmethaacrylamide) or a copolymer thereof. Such a polymeric backbone comprises methacrylamide backbone units having attached thereto either 2-hydroxypropyl groups or such 2-hydroxypropyl groups that have been modified by attaching thereto (directly or indirectly) the moieties described herein (e.g., therapeutically active agent(s) and/or targeting moiety).

Poly(hydroxyalkylmethacrylamide) (HPMA) polymers are a class of water-soluble synthetic polymeric carriers that have been extensively characterized as biocompatible, non-immunogenic and non-toxic. One advantage of HPMA polymers over other water-soluble polymers is that they may be tailored through relatively simple chemical modifications, in order to regulate their respective drug and targeting moiety content. Further, the molecular weight and charge of these polymers may be manipulated so as to allow renal clearance and excretion from the body, or to alter biodistribution while allowing tumor targeting.

In some of any of the embodiments described herein, the polymeric backbone is derived from, or corresponds to, polyglutamic acid (PGA). PGA is a polymer composed of units of naturally occurring L-glutamic acid linked together through amide bonds. The pendant free γ-carboxyl group in each repeating unit of L-glutamic acid is negatively charged at a neutral pH, which renders the polymer water-soluble. The carboxyl groups also provide functionality for drug attachment. PGA is biodegradable and FDA-approved.

Cysteine proteases, particularly cathepsin B, play key roles in the lysosomal degradation of PGA to its nontoxic basic components, L-glutamic acid, D-glutamic acid and D,L-glutamic acid. The cellular uptake of negatively charged polymers can be hindered due to electrostatic repulsion forces between the polymers and the rather negatively charged surface of the cells. Although PGA is no exception to this rule, it does not diminish the EPR effect and the accumulation and retention of PGA-drug conjugates in solid tumors. Specific receptor-mediated interactions of PGA-drug conjugates containing targeting ligands may also increase the rate of polymer uptake into the target cells.

As used herein, "a polyglutamic acid" or "polyglutamic acid polymer" encompasses poly(L-glutamic acid), poly(D-glutamic acid), poly(D,L-glutamic acid), poly(L-gamma glutamic acid), poly(D-gamma glutamic acid) and poly(D,L-gamma glutamic acid).

PGA is usually prepared from poly(γ-benzyl-L-glutamate) by removing the benzyl protecting group with the use of hydrogen bromide. A sequential copolymer of protected PGA may be synthesized by peptide coupling reactions. For the preparation of high-molecular-weight homopolymers and block or random copolymers of protected PGA, triethylamine-initiated polymerization of the N-carboxyanhydride (NCA) of γ-benzyl-L-glutamate is used.

Water-soluble copolymers such as N-2-hydroxypropyl methacrylamide (HPMA) copolymer and polyglutamic acid (PGA) are biocompatible, non-immunogenic and non-toxic carriers that enable specific delivery into tumor tissue (Satchi-Fainaro et al. *Nat Med* 2004; 10: 255-261). These macromolecules do not diffuse through normal blood vessels but rather accumulate selectively in the tumor site because of the EPR effect. This phenomenon of passive diffusion through the hyperpermeable neovasculature and localization in the tumor interstitium is observed in many solid tumors for macromolecular agents and lipids.

For any of the polymeric conjugates described herein, the plurality of the backbone units forming the polymeric backbone in the conjugate comprises two or more different portions of backbone units that differ from one another by the presence and/or nature of the moiety attached thereto. For example, one portion of the backbone units are "free" backbone units, and one portion of the backbone units have a therapeutically active agent attached thereto. In another example, a third portion of the backbone units have another therapeutically active agent attached thereto, or a targeting moiety attached thereto.

The different backbone units that have a moiety attached thereto can be randomly dispersed within the polymeric backbone.

In some of any of the embodiments of the invention, a polymeric conjugate as described herein comprises a polymeric backbone comprised of a plurality of backbone units, whereby a portion of these backbone units have a therapeutically active agent attached thereto. When the conjugate comprises two or more therapeutically active agents, the polymeric backbone is further comprised of other portions of the backbone units, each comprises a different therapeutically active agent attached to the backbone unit. When the polymer also comprises a targeting moiety, another portion of these backbone units have the targeting moiety attached thereto. Those backbone units within the polymeric backbone that do not have a moiety attached thereto are referred to herein as "free" or "non-functionalized" backbone units.

Thus, in some embodiments, a polymeric backbone as described herein is formed of a plurality of backbone monomeric units, which are covalently linked to one another so as to form the polymeric backbone. The backbone units are therefore such that, if not having certain moieties attached thereto, as described herein, form a polymeric backbone of a polymer. The plurality of backbone units as described herein, and the polymeric backbone comprised thereof, are therefore also defined herein as derived from, or corresponding to, the polymeric backbone of such a polymer. The plurality of backbone units as described herein, and the polymeric backbone comprised thereof, therefore correspond to, or are derived from, a polymer, whereby one or more moieties, as described herein, are attached to one or more portions of the backbone units. Since once the one or more moieties are attached to one or more portions of the backbone units forming the polymeric backbone, the backbone units forming the polymeric backbone are not identical to one another, as in the case of an "intact" polymer, and hence the polymeric conjugate is actually a copolymer, or has a copolymeric backbone, which is comprised of two or more types of backbone units. The phrase "polymeric backbone" as used herein therefore describes a "copolymeric backbone" comprised of at least two different types of backbone units.

It is to be noted that portions of the backbone units differ from one another by the presence and type of the moiety or agent that are attached to the backbone unit, but maintain the chemical structure of the portion of the backbone unit that forms the polymeric backbone. In analogy to a peptide, the portions of the backbone units differ from one another by the side chain of the amino acid. The portions of the backbone units thus differ from one another by the presence and/or nature of the pendant group thereof.

In some of any of the embodiments described herein, a polymeric conjugate as described herein comprises a polymeric (or copolymeric) backbone formed from a plurality of backbone units, and the plurality of backbone units comprise the following backbone units:

-A-, which represents a backbone unit within the polymeric backbone, or, in other words, a backbone unit of the polymer from which the polymeric backbone is derived, and is "free" of moieties that attached thereto, and one or more of the following backbone units:

-A-T1-, which represents a backbone unit of the polymer from which the polymeric backbone is derived (a backbone unit within the polymeric backbone), having a first therapeutically active agent (T1) attached thereto;

-A-T2-, which represents a backbone unit of the polymer from which the polymeric backbone is derived (a backbone unit within the polymeric backbone), having a second therapeutically active agent (T2) attached thereto, the second therapeutically active agent being different T1; and -A-L-, which represents a backbone unit of the polymer from which the polymeric backbone is derived (a backbone unit within the polymeric backbone), having a targeting moiety attached thereto.

The backbone units can be arranged within the polymeric backbone in any order.

In some embodiments, the plurality of backbone units forming the polymeric backbone comprises the following portions of backbone units:

-(A)$_y$-;
-(A-T1)$_x$-
-(A-T2)$_z$-; and
-(A-L)$_n$, wherein:

A is a backbone unit within the polymeric backbone, as described herein;

A-T1 is a backbone unit within the polymeric backbone having attached thereto a first therapeutically active agent (T1), as described herein;

A-T2 is a backbone unit within the polymeric backbone having attached thereto a second therapeutically active agent (T2), as described herein;

A-L is a backbone unit within the polymeric backbone having attached thereto a targeting moiety (L), as described herein;

y ranges from 50 to 99.9 mol percents, or from 70 to 99.9 mol percents;

x ranges from 0.1 to 20 mol percents; and each of z and n independently ranges from 0 to 20 mol percents.

In some of any of the embodiments described herein, the polymeric conjugate comprises a polymeric backbone comprised of a plurality of backbone monomeric units as described herein, the polymeric backbone being represented by Formula I as follows:

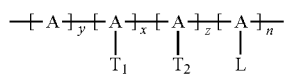

Formula I wherein:

A is a backbone unit forming said polymeric backbone;
T1 is the first therapeutically active agent (e.g. paclitaxel);
T2 is a second therapeutically active agent (e.g., doxorubicin or TNP-470);
L is a targeting moiety;
y ranges from 50 to 99.9 mol percents;
x ranges from 0.1 to 20 mol percent; and
z ranges from 0.1 to 20 mol percent; and
n ranges from 0 to 10 mol percent.

Herein, the phrases "loading onto the polymer", or simply "load", are used to describe the amount of an agent or moiety that is attached to the polymeric backbone of the conjugates described herein, and is represented herein by the mol percent (mol %) of this agent or moiety in the conjugate, as defined hereinafter.

Herein "mol percent" represents the number of moles of an attached moiety per 1 mol of the polymeric conjugate, multiplied by 100.

The % loading can be measured by methods well known by those skilled in the art, some of which are described hereinbelow under the Materials and Methods of the Examples section that follows.

In some of any of the embodiments described herein, when n is 0, such that none of the backbone units are backbone units have a targeting moiety attached thereto, the plurality of backbone units comprises, in addition to a plurality of -A- units, as described herein, both -A-T1- and -A-T2- units, such that the polymeric conjugate comprises two therapeutically active agents attached thereto. Thus, in these embodiments, z ranges from 0.1 to 20 mol percent and is different from 0.

In some of these embodiments, the plurality of backbone units may comprise also -(A-T3)k- units. A "A-T3" unit is a backbone unit within the polymeric backbone that has attached thereto a third therapeutically active agent, being different from T1 and T2. "k" ranges from 0.1 to 20 mol percent.

In some of any of the embodiments described herein, when z is 0, such that the plurality of backbone units comprises, in addition to a plurality of -A- units, as described herein, -A-T1- units, but not -A-T2- units, n is different from 0 and ranges from 0.1-10 mol percents, such that the polymeric conjugate comprises a therapeutically active agent and a targeting moiety attached thereto.

In some of these embodiments, the targeting moiety L is a ligand of a cell-surface receptor, whereby the receptor is neural cell adhesion molecule (NCAM). Thus, in these embodiments, the targeting moiety is an NCAM targeting moiety, which comprises a ligand of NCAM.

In some of any of the embodiments described herein, a load of any of therapeutically active agents, when present within the polymeric conjugate, denoted by "x", "z" or "k", ranges from 0.1 to 20 mol percent, or from 1 to 20 mol percent, and can be, for example, 0.1, 0.5, 1, 2, 3, 4, 5, 6, 7 8, 9, 10, 11, 12, 13, 14, 15, 16, 17, 18, 19 and 20, and even higher values, including any value therebetween.

In some of any of the embodiments described herein, the load of the targeting moiety, when different from 0, denoted as "n" in Formula I, ranges from 0.1 to 20 mol percent, or from 0.1 to 10 mol percent, or from 1 to 10 mol percent, and can be, for example, 0.1, 0.5, 1, 2, 3, 4, 5, 6, 7 8, 9, 10, 11, 12, 13, 14, 15, 16, 17, 18, 19 and 20, and even higher values, including any value therebetween.

In any of the embodiments described herein, the (one or more) therapeutically active agent(s) is an anti-cancer agent and/or an anti-angiogenic agent.

The phrase "therapeutically active agent", which is interchangeably referred to herein as "drug", describes a compound which exhibits a beneficial pharmacological effect when administered to a subject and hence can be used in the treatment of a condition that benefits from this pharmacological effect.

The term "subject" (alternatively referred to herein as "patient") as used herein refers to an animal, preferably a mammal, most preferably a human, who has been the object of treatment, observation or experiment.

The phrase "anti-cancer agent", as used herein, describes a therapeutically active agent that directly or indirectly kills cancer cells or directly or indirectly inhibits, stops or reduces the proliferation of cancer cells. Anti-cancer agents include those that result in cell death and those that inhibit cell growth, proliferation and/or differentiation. In some embodiments, the anti-cancer agent is selectively toxic against certain types of cancer cells but does not affect or is less effective against normal cells. In some embodiments, the anti-cancer agent is a cytotoxic agent.

The phrase "cytotoxic agent", as used herein, describes a compound that mediates cell death. Cell death mediation can be exhibited by a mechanism such as, but not limited to, apoptosis, inhibition of metabolism or DNA synthesis, interference with cytoskeletal organization, destabilization or chemical modification of DNA, etc. The agent may act, for example, as an anti-proliferative agent or as a pro-apoptotic agent, which induces apoptosis.

In some embodiments, the anti-cancer agent is doxorubicin.

Some anti-cancer agents act as angiogenesis inhibitors, as discussed hereinabove.

The phrase "anti-angiogenesis agent", which is also referred to herein interchangeably as "anti-angiogenic agent" or "angiogenesis inhibitor", describes an agent having the ability to (a) inhibit endothelial cell proliferation or migration, (b) kill proliferating endothelial cells, and/or (c) inhibit the formation of new blood vessels in a tissue.

As discussed hereinabove, some anti-angiogenic agents are useful in the treatment of cancer and hence can also be referred to as anti-cancer agents.

Exemplary anti-angiogenic agents include Paclitaxel and TNP-470.

In embodiments where the conjugate comprises two therapeutically active agents, these agents act in synergy or at least exhibit an additive therapeutic effect.

As described in the Examples section that follows, the present inventors have demonstrated that paclitaxel and doxorubicin act in synergy, at almost all tested concentrations and ratios, and on various cell lines. The present inventors have also demonstrated that a synergistic effect is exhibited by a combination of paclitaxel and TNP-470.

According to some embodiments, there is provided a polymeric conjugate comprising a polymeric backbone formed of a plurality of backbone units "A" as described herein, in which T1 in "A-T1" backbone units is paclitaxel, and in which z is different from 0 (ranges from 0.1-20 mol percent as described herein), and T2 in "A-T2" backbone units is doxorubicin.

In some of these embodiments, the polymeric backbone of the conjugate corresponds to a polymeric backbone of HPMA. Such a polymeric conjugate is referred to herein as HPMA-PTX-DOX. An exemplary such conjugate was shown to exhibit exceptional activity and synergism, in in vitro studies conducted on various cell lines.

In some of these embodiments, the polymeric backbone is derived from PGA. Such a polymeric conjugate is referred to herein as PGA-PTX-DOX. An exemplary such conjugate was shown to exhibit exceptional activity and synergism, both in in vitro studies conducted on various cell lines, and in in vivo studies.

According to some embodiments, there is provided a polymeric conjugate comprising a polymeric backbone formed of a plurality of backbone units "A" as described herein, in which T1 in "A-T1" backbone units is paclitaxel, and in which z is different from 0 (ranges from 0.1-20 mol percent as described herein), and T2 in "A-T2" backbone units is TNP-470.

As demonstrated in the Examples section that follows, a combination of PTX and TNP-470 was shown to exhibit a synergistic effect when combined also with alendronate, when the latter is present in an amount where it exhibits a therapeutic activity.

Thus, in some of the embodiments of a polymeric conjugate which comprises a polymeric backbone formed of a plurality of backbone units "A" as described herein, in which T1 in "A-T1" backbone units is paclitaxel, and in which z is different from 0 (ranges from 0.1-20 mol percent as described herein), and T2 in "A-T2" backbone units is TNP-470, the plurality of backbone units further comprises units of the type -(A-T3)-, and T3 is alendronate.

In some of these embodiments, the mol percent of units A-T3, is denoted as "k" and ranges from 0.1 to 20 mol percent.

The alendronate can serve both as a therapeutically active agent and as a targeting moiety.

In some of any of the embodiments described herein for polymeric conjugates having attached thereto two or more therapeutically active agents, the plurality of backbone units may further comprise backbone units to which a targeting moiety is attached, and which are referred to herein as -(A-L)n- backbone units.

As described herein, in some embodiments, the targeting moiety is a ligand of a cell-surface receptor which is expressed in tumor cells and/or endothelial cells.

In some embodiments, the targeting moiety is a ligand of a cell-surface receptor that is expressed in endothelial cells, e.g., proliferating endothelial cells.

In some embodiments, the targeting moiety is an angiogenesis targeting moiety.

The phrase "angiogenesis targeting moiety" describes a chemical moiety that can bind to a location in a mammal in which neovascularization, such as neovascularization of tumor cells, occurs (e.g., can bind to an angiogenesis-associated receptor). The phrase "neovascularization" is meant to encompass two unique processes: vasculogenesis, the de novo assembly of blood vessels, and angiogenesis, the formation of new capillary sprouts from pre-existing vessels.

The angiogenesis targeting moiety described herein is derived from compounds that can selectively bind to a location in a mammal in which neovascularization occurs and hence may serve to deliver the conjugate described herein to the desired location.

In some embodiments the targeting moiety is capable of binding to an angiogenesis-associated integrin as a cell-surface receptor expressed in proliferating endothelial cells. In some embodiments, the targeting moiety targets the $\alpha_v\beta_3$ integrin receptor.

The $\alpha_v\beta_3$ integrin is overexpressed on proliferating endothelial cells such as those present in growing tumors, as well as on some tumor cells of various origins. The RGD sequence represents the minimal amino acid domain, in several extracellular matrix proteins, which has been demonstrated to be the binding site of the transmembrane integrins proteins family [Bazzoni et al. 1999, *Current Opinion in Cell Biology*; (11) pp. 573-581].

Accordingly, in some embodiments, the angiogenesis targeting moiety comprises at least one Arg-Gly-Asp (RGD; SEQ ID NO:7) moiety, or a peptidomimetic thereof (e.g. E-[c(RGDfK)$_2$]), and can optionally further include other amino acids, amino acid derivatives, or other chemical groups (e.g., alkylene chains).

In some embodiments, the RGD-containing moiety is an oligopeptide. The oligopeptide can be a cyclic oligopeptide (including, for example, monocyclic, bicyclic and tricyclic oligopeptides) or a linear oligopeptide, and can include, in addition to the Arg-Gly-Asp amino acid sequence, from 1 to 10 amino acids.

It has been further found that the substrate specificity of RGD-containing moieties results from the different conformations of the RGD sequence in different matrix proteins.

In an embodiment, the oligopeptide is a cyclic peptide comprising a c[Arg-Gly-Asp-Phe-Lys] amino acid sequence (SEQ ID NO:8).

In some embodiments, the angiogenesis targeting moiety comprises two or more Arg-Gly-Asp-containing moieties, wherein the moieties can be the same or different.

Exemplary Arg-Gly-Asp-containing moieties that are suitable for use in the context of embodiments of the invention include, but are not limited to c(RGDfk) (SEQ ID NO:8), RGD4C (SEQ ID NO:9), E-[c(RGDfK)$_2$] (SEQ ID NO:10) and other RGD-containing cyclic peptides such as those described in Haubner et al. [*J. Am. Chem. Soc.* 1996, 118, 7881-7891] and Capello, et al. [*J. Nucl. Med.* 2004, 45(10), 1716-20] and in WO 97/06791 and U.S. Pat. No. 5,773,412. Exemplary effective RGD cyclic peptides are the Arg-Gly-Asp (RGD) cyclic pentapeptides in which two amino acids such as D-tyrosine and lysine were added to the RGD and the pentapeptide was transformed into cyclic pentapeptide.

In some embodiments, the RGD-containing moiety can comprise two or more -Arg-Gly-Asp- moieties, being either linked to one another or being spaced by one or more amino acids or any other spacer, as defined herein.

In some embodiments, the cell-surface receptor is NCAM and the targeting moiety is NCAM targeting moiety.

In some embodiments, the NCAM targeting moiety is a ligand of the NCAM receptor, and, in some embodiments, it is a ligand that is specific to NCAM receptor.

In some embodiments, the ligand of NCAM is a peptide. Such peptides are referred to herein and in the art as NCAM-targeting peptides or abbreviated as NTP.

In some embodiments, the peptide comprises the amino acid sequence DDSDEEN (SEQ ID NO:5), which is known to target NCAM. In some of these embodiments, the NTP may further comprise one or more amino acid residues, at each terminus thereof, which may serve, for example, to facilitate attachment to the polymeric backbone and/or to improve its targeting by improved exposure (reduced stearic hindrance by the polymer). In some embodiments, the NCAM targeting peptide is of the 8-amino acid sequence GDDSDEEN (SEQ ID NO:1).

In some embodiments, the NCAM targeting peptide comprises an amino acid sequence of the C3 peptide, ASKKP-KRNIKA (SEQ ID NO:6). In some of these embodiments, the peptide may further comprise one or more amino acid residues, at each terminus thereof, which may serve, for example, to facilitate attachment to the polymeric backbone and/or to improve its targeting by improved exposure (reduced stearic hindrance by the polymer). In some embodiments, the NCAM targeting peptide is of the sequence GASKKPKRNIKA (SEQ ID NO:3), with added glycine spacer at the N-terminal.

Additional targeting moieties which are ligands of cell-surface receptors expressed in tumor cells or endothelial cells are also contemplated.

According to another aspect of some embodiments of the present invention there is provided a polymeric conjugate which comprises a polymeric backbone having attached thereto a therapeutically active agent and a targeting moiety which is an NCAM targeting moiety. The NCAM targeting moiety can be a ligand of NCAM as described herein.

In some of these embodiments the polymeric backbone is comprised of a plurality of backbone units which comprises the following backbone units:

-A-, -A-T1- and -A-L-, as described herein, wherein T1 is paclitaxel and L is an NCAM targeting peptide as described herein.

The mol percents "x" of the A-T1 backbone units in the polymeric backbone is as described hereinabove.

The mol percent "n" of the A-L backbone units in the polymeric backbone can range from 0.1 to 10 mol percent.

In each of the conjugates described herein, the therapeutically active agent(s) and the targeting moiety can each independently be linked to the respective portion of the backbone units in the polymeric backbone directly, or indirectly, through a linker moiety (also referred to herein as a linker, a linker group or a linking group), whereby, in some embodiments, the direct/indirect linkage is designed as being cleavable at conditions characterizing the desired bodily site (e.g., by certain enzymes or pH), as detailed hereinbelow.

Hence, according to some of any of the embodiments described herein, at least one of the therapeutically active agent(s) and/or the targeting moiety, if present, is attached to the respective backbone units via a linker. The linker linking each of the therapeutically active agent(s) to the polymer and the linker linking the targeting moiety to the polymer may be the same or different.

The linker described herein refers to a chemical moiety that serves to couple the targeting moiety and/or the therapeutically active agent(s) to the polymeric backbone (to the respective portion of backbone units) while not adversely affecting either the targeting function of the targeting moiety or the therapeutic effect of the targeting moiety and/or the therapeutically active agent(s).

In some embodiments, the linker is a biodegradable linker.

The phrase "biodegradable linker", as used herein, describes a linker that is capable of being degraded, or cleaved, when exposed to physiological conditions. Such physiological conditions can be, for example, pH, a certain enzyme, and the like. This phrase as is also referred to herein interchangeably as "biocleavable linker".

In some embodiments, the linker is designed as being cleavable at conditions characterizing the desired bodily site (e.g., by certain enzymes or pH), as detailed hereinbelow.

According to some embodiments, the biodegradable linker is a pH-sensitive linker, a hydrolysable linker or an enzymatically cleavable linker.

In some embodiments, the linker is capable of being cleaved by pre-selected cellular enzymes, for instance, those found in osteoblasts, osteoclasts, lysosomes of cancerous cells or proliferating endothelial cells. Alternatively, an acid hydrolysable linker could comprise an ester or amide linkage.

In some embodiments the biodegradable linker is an enzymatically cleavable linker. Such a linker is typically designed so as to include a chemical moiety, typically, but not exclusively, an amino acid sequence that is recognized by a pre-selected enzyme. Such an amino acid sequence is often referred to in the art as a "recognition motif". A conjugate comprising such a linker typically remains substantially intact in the absence of the pre-selected enzyme in its environment, and hence does not cleave or degrade so as to the release the agent attached thereto until contacted with the enzyme.

In some embodiments, the enzymatically cleavable linker is cleaved by an enzyme which is overexpressed in tumor tissues. A conjugate comprising such a linker ensures, for example, that a substantial amount of a conjugated therapeutically active agent is released from the conjugate only at the tumor tissue, thus reducing the side effects associated with non-selective administration of the drug and further enhancing the concentration of the drug at the tumor site.

Exemplary enzymes which are suitable for use in the context of these embodiments include, but are not limited to the group consisting of Cathepsin B, Cathepsin K, Cathepsin D, Cathepsin H, Cathepsin L, legumain, MMP-2 and MMP-9.

Suitable linkers include, but are not limited to, alkyl chains; alkyl chains optionally substituted with one or more substituents and in which one or more carbon atoms are optionally interrupted by a nitrogen, oxygen and/or sulfur heteroatom.

Other suitable linkers include amino acids and/or oligopeptides.

Such alkyl chains and/or oligopeptides can optionally be functionalized so as allow their covalent binding to the moieties linked thereby (e.g., the polymeric backbone and the targeting moiety, the polymer and the therapeutically active agent). Such a functionalization may include incorporation or generation of reactive groups that participate in such covalent bindings, as detailed hereinunder.

In some embodiment, the linker is a biodegradable oligopeptide which contains, for example, from 2 to 10 amino acid residues.

In some embodiments, the linker is a Cathepsin B-cleavable linker.

Cathepsin B is a lysosomal enzyme overexpressed in both epithelial and endothelial tumor cells. Suitable exemplary linkers having cathepsin-B cleavable sites include amino acid sequences such as, but are not limited to -[Cit-Val]- (SEQ ID NO:11), -[Arg]- (SEQ ID NO:21), -[Arg-Arg]- (SEQ ID NO:22), -[Phe-Lys]- (SEQ ID NO:12) -[Val-Arg]- (SEQ ID NO:13), -[Phe-Arg]- (SEQ ID NO:14), -[6-Glu-8-Asp]- (SEQ ID NO:23), -[Gly-Phe-Leu-Gly]- (SEQ ID NO:15), -[Gly-Phe-Ala-Leu]- (SEQ ID NO:16) and -[Ala-Leu-Ala-Leu]- (SEQ ID NO:17), -[Gly-Leu-Gly]- (SEQ ID NO:18), -[Gly-Phe-Gly]- (SEQ ID NO:19), -[Gly-Phe-Leu-Gly-Phe-Lys]- (SEQ ID NO:20) and combinations thereof.

In some embodiments the enzymatically cleavable linker is cleaved by cathepsin K.

Cathepsin K is a lysosomal cysteine protease involved in bone remodeling and resorption and is predominantly expressed in osteoclasts. Its expression is stimulated by inflammatory cytokines that are released after tissue injury and in bone neoplasms [Pan et al. 2006, *J Drug Target* 14:425-435; Husmann et al. 2008, *Mol Carcinog* 47: 66-73; Segal et al. *PLoS One* 2009, 4(4):e5233].

A non-limiting example of a linker having cathepsin K cleavable sites is -[Gly-Gly-Pro-Nle]- (SEQ ID NO:24).

In some embodiments the linker comprises the amino acid sequences -[Gly-Leu-Gly]- (SEQ ID NO:25), -[Gly-Phe-Gly]- (SEQ ID NO:26), -[Gly-Leu-Phe-Gly]- (SEQ ID NO:27), -[Gly-Phe-Leu-Gly]- (SEQ ID NO:28), -[Phe-Lys]- (SEQ ID NO:29) and -[Gly-Phe-Leu-Gly-Phe-Lys]- (SEQ ID NO:30) and -[Gly-Gly-Pro-Nle]- (SEQ ID NO:24). In some embodiments, the linker consists of these amino acid sequences or a combination thereof.

An oligopeptide linker which contains the pre-selected amino acid sequence (recognition motif) can also be constructed such that the recognition motif is repeated several times within the linker, to thereby enhance the selective release of the attached agent. Various recognition motifs of the same or different enzymes can also be incorporated within the linker. Similarly, the linker may comprise multiple pH sensitive bonds or moieties. Linkers comprising such multiple cleavable sites can enhance the selective release of the therapeutically active agent at the desired bodily site, thereby reducing adverse side effects, and further enhance the relative concentration of the released drug at the bodily site when it exhibits its activity.

In cases where the targeting moiety and/or the therapeutically active agent(s) is/are bound directly to the polymeric backbone, the bond linking these moieties can also be biodegradable, for example, a hydrolysable bond, an enzymatically-cleavable bond or a pH-sensitive bond. Such a bond can be formed upon functionalizing the polymeric backbone, the targeting moiety and/or the therapeutically active agent, so as to include compatible reactive groups, as defined herein, for forming the required bond.

According to some embodiments, the biodegradable linker is a pH-sensitive linker or an enzymatically-cleavable linker.

A pH-sensitive linker comprises a chemical moiety that is cleaved or degraded only when subjected to a certain pH condition, such as acidic pH (e.g., lower than 7), neutral pH (6.5-7) or basic pH (higher than 7).

Such a linker may, for example, be designed to undergo hydrolysis under acidic or basic conditions, and thus, the conjugate remains intact and does not release the agents attached to the polymer in the body, until it reaches a physiological environment where a pH is either acidic or basic, respectively.

Exemplary pH-sensitive linkers include, but are not limited to, a hydrazone bond, ester (including orthoester) bond, amide bond of cis-aconytil residue, a trityl group, acetals, ketals, Gly-ester and a -[Gly-Phe-Gly]- moiety.

The peptide linker may also include a peptide sequence which serves to increase the length of the linker. Longer peptides may be advantageous due to a more efficient steric interaction of the linker with the cleaving enzyme due to enhanced accessibility.

In some embodiments, when the therapeutically active agent is paclitaxel, it is attached to a backbone unit within the polymeric backbone via a hydrolysable linker (e.g., an ester bond or a linker that comprises an ester bond), which can be, for example, cleavable by hydrolases.

In some embodiments, paclitaxel is attached the backbone units by an enzymatically cleavable linker, such as cathepsin C cleavable linker, as described herein.

In some embodiments, when the therapeutically active agent is doxorubicin, it is attached to the backbone unit by an acid-cleavable linker, which can comprise, for example, a hydrazone moiety.

In some embodiments, doxorubicin is attached the backbone units by an enzymatically cleavable linker, such as cathepsin C cleavable linker, as described herein.

In some embodiments, when the therapeutically active agent is TNP-470, it is attached to the backbone unit by an enzymatically cleavable linker, such as cathepsin C cleavable linker, as described herein.

In some embodiments the targeting moiety is linked to the polymeric backbone or to the linker via a spacer. In some embodiments the therapeutically active agent is linked to the polymeric backbone or to the linker via a spacer. The spacers can be the same or different.

The term "spacer" as used herein describes a chemical moiety that is covalently attached to, and interposed between, the polymeric backbone and the linker, or the targeting moiety/therapeutically active agent, thereby forming a bridge-like structure between the polymeric backbone and/or the targeting moiety/therapeutically active agent. Alternatively, the spacer may be covalently attached to, and interposed between, the linker and the therapeutically active agent and/or the targeting moiety.

Hence, according to some embodiments at least one of the therapeutically active agent(s) and the targeting moiety is attached to the polymeric backbone and/or to the linker via a spacer.

Suitable spacers include, but are not limited to, alkylene chains, optionally substituted by one or more substituents and which are optionally interrupted by one or more nitrogen, oxygen and/or sulfur heteroatom.

Other suitable spacers include amino acids and amino acid sequences, optionally functionalized with one or more reactive groups for being coupled to the polymeric backbone/targeting moiety/therapeutically active agent/linkers.

In some embodiments, the spacer has the formula G-$(CH_2)$n-K, wherein n is an integer from 1 to 10; and G and K are each a reactive group such as, for example, NH, O or S. In some embodiments, G and K are each NH and n is 2.

An exemplary spacer is —[NH—$(CH_2)_m$NH$_2$]— wherein "m" stands for an integer ranging from 1-10. Preferably m is 2.

In some embodiments, the spacer is an amino acid sequence, optionally an inert amino acid sequence (namely, does not affect the affinity or selectivity of the conjugate). Such a spacer can be utilized for elongating or functionalizing the linker.

Exemplary such sequences include, for example, -[Gly-Gly-] and -[Phe-Lys]-.

In some cases, a spacer is utilized for enabling a more efficient and simpler attachment of the targeting moiety and/or therapeutically active agent to the polymeric backbone or linker, in terms of steric considerations (renders the site of the polymer to which coupling is effected less hindered) or chemical reactivity considerations (adds a compatible reactive group to the site of the polymer to which coupling is effected). In some cases, the spacer may contribute to the performance of the resulting conjugate. For example, the spacer may render an enzymatically cleavable spacer less sterically hindered and hence more susceptible to enzymatic interactions.

In some embodiments, the spacer facilitates the attachment of the moiety or agent to the polymeric backbone or the linker. This may be effected by imparting a reactive group to the moiety to be attached, which is chemically compatible with functional groups in the polymeric backbone and/or the linker attached to the polymeric backbone, and/or by modifying the solubility of the moiety to be attached to the polymer, so as to facilitate the reaction between the polymer (or co-polymer) and the moiety.

In some embodiments, the spacer is a degradable spacer, which is capable of undergoing degradation reactions so as to release the agent attached thereto. In some embodiments, the spacer is biodegradable, as defined herein.

A spacer may also be used in order to attach other agents (e.g., a labeling agent, as described hereinbelow) to the conjugate.

The spacer may be varied in length and in composition, depending on steric consideration and may be used to space the angiogenesis targeting moiety and/or therapeutically active agent form the polymeric backbone.

In some embodiments the spacer is a substituted or unsubstituted aryl group and substituted or unsubstituted heteroaryl group whereby the substituents can be carbonate, C-amido, N-amido and amine, whereby the spacer may be linked to the anti-angiogenic agent/bone targeting moiety/linker/polymer either directly, through the aromatic group or alternatively, via one or more of the substituents.

In some embodiments, the spacer is a degradable spacer selected such that it undergoes a spontaneous degradation once it is cleaved from the polymeric conjugate. In some embodiments, the spacer is a degradable spacer selected such that it undergoes a spontaneous degradation once it is cleaved from the polymeric conjugate.

Such a spacer can be, for example, attached to a biodegradable linker at one end and to an anti-angiogenic agent or a bone targeting moiety at another end, such that once the biodegradable linker is cleaved, so as to release the spacer and the moiety attached thereto, the spacer undergoes a spontaneous degradation so as to release the moiety attached thereto.

Exemplary spacers that can undergo such a spontaneous degradation include, but are not limited, chemical moieties that can undergo a spontaneous 1,4-, 1,6-, 1,8-, etc. elimination, via a cascade of immolative electronic reactions. Such chemical groups are known in the art, or, otherwise, can be devised by those skilled in the art.

In an exemplary embodiment, the spacer is such that can undergo a spontaneous 1,6-benzyl elimination. An example of such a spacer is p-aminobenzyl carbonate (PABC). Such a spacer can be used, for example to attach paclitaxel to PGA-derived backbone units, and is obtained by conjugating PTX with p-aminobenzyl alcohol (PABA). Such a spacer results in forming an ester bond between PTX and the polymer.

The spacer may be varied in length and in composition, depending on steric consideration and may be used to space the anti-angiogenic agent and/or bone targeting moiety form the polymeric backbone.

The following describes exemplary polymeric conjugates according to some embodiments of the present invention.

In some embodiments, the polymeric conjugate comprises an NCAM targeting peptide and paclitaxel bound to PGA backbone. The targeting peptide and paclitaxel can be conjugated to the pendant carboxylic acid groups on PGA backbone via the N-terminal amine of the peptide, to form an amide bond, and a hydroxyl group of the paclitaxel to form an ester bond.

In some embodiments, the polymeric conjugate comprises an NCAM targeting peptide and doxorubicin bound to polyglutamic acid (PGA) backbone. Peptide and doxorubicin can be conjugated to the pendant carboxylic acid groups on PGA backbone via the N-terminal amine of the peptide and the amino group on doxorubicin. Alternatively, doxorubicin is attached to the backbone units via a hydrozaone-containing linker and/or an enzymatically-cleavable linker as described and exemplified herein.

In some embodiments, the polymeric conjugate comprises an NCAM targeting peptide, doxorubicin and paclitaxel bound to polyglutamic acid (PGA) backbone.

In some embodiments, the targeting peptide is the C3 peptide with added glycine spacer at the N-terminal, having the amino acid sequence GASKKPKRNIKA (SEQ ID NO:3).

In some embodiments, the polymeric conjugate comprises paclitaxel and doxorubicin bound to PGA or to HPMA.

The chemical structures of exemplary conjugates are presented, inter alia, in FIGS. 18 and 19D.

Additional exemplary conjugates can be represented by the following formulae:

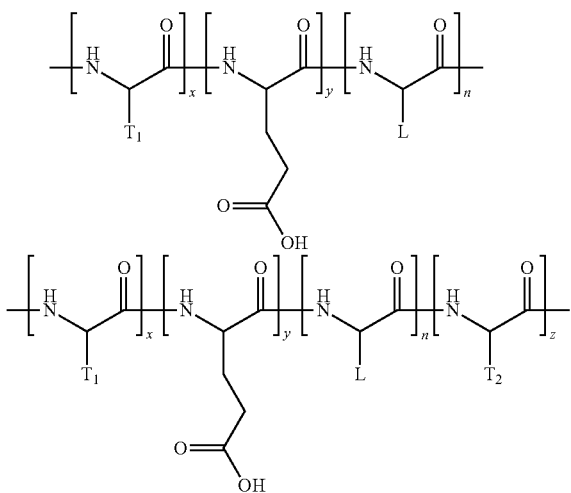

with T1, T2, L, x, y, z and n are as described herein.

In the course of practicing embodiments of the present invention, it was uncovered that a successful attachment of the highly-sensitive drug doxorubicin is facilitated by using a hydrazone-containing linker. Such a linker enables attachment of the doxorubicin under conditions in which the doxorubicin's structure is not affected, and further enables smooth release of the drug at the desired site, as demonstrated in the Examples section that follows.

Thus, according to an aspect of some embodiments of the present invention there is provided a chemical conjugate that comprises a polymeric backbone as described herein wherein doxorubicin is attached to a portion of the backbone units forming the polymeric backbone via a hydrazone-containing moiety.

A "hydrazone-containing moiety" encompasses a —NH—NH—C(=O)— group, which may further comprise linking moieties for attaching it to the drug and/or the backbone units. Such linking moieties include, for example, alkylene chain that bears one or more functional groups that may be coupled with functional groups of the backbone unit and/or doxorubicin. An exemplary moiety is described in the Examples section that follows.

Each of the polymeric conjugates described herein may further comprise a labeling agent attached to the polymeric backbone. The labeling agent can be attached to the N-terminus of the polymeric backbone, either directly, or by means of a spacer, as described herein. Alternatively, the labeling agent can be attached to a portion of the backbone units forming the polymeric backbone, directly or via a spacer, such that the plurality of backbone units forming the polymeric backbone further comprises units of the type -[A-P]m, whereas:

P is the labeling moiety;
A-P is a backbone unit having the labeling moiety attached thereto; and
m ranges from 0.1 to 10 mol percent.

In some embodiments, the labeling agent can be attached to any of the therapeutically active agent(s) and/or targeting moieties attached to the polymeric backbone. For example, the labeling agent can be attached to a targeting moiety which is a peptide, as described herein.

The attachment of a labeling agent to the conjugate, enables utilizing these conjugates for monitoring bone related disease or disorders, for example, monitoring the therapeutic effect exhibited by the conjugate described herein.

As used herein, the phrase "labeling agent" describes a detectable moiety or a probe. Exemplary labeling agents which are suitable for use in the context of these embodiments include, but are not limited to, a fluorescent agent, a radioactive agent, a magnetic agent, a chromophore, a bioluminescent agent, a chemiluminescent agent, a phosphorescent agent and a heavy metal cluster.

The phrase "radioactive agent" describes a substance (i.e. radionuclide or radioisotope) which loses energy (decays) by emitting ionizing particles and radiation. When the substance decays, its presence can be determined by detecting the radiation emitted by it. For these purposes, a particularly useful type of radioactive decay is positron emission. Exemplary radioactive agents include $^{99m}$Tc, $^{18}$F, $^{131}$I and $^{125}$I.

The term "magnetic agent" describes a substance which is attracted to an externally applied magnetic field. These substances are commonly used as contrast media in order to improve the visibility of internal body structures in Magnetic resonance imaging (MRI). The most commonly used compounds for contrast enhancement are gadolinium-based. MRI contrast agents alter the relaxation times of tissues and body cavities where they are present, which depending on the image weighting can give a higher or lower signal.

As used herein, the term "chromophore" describes a chemical moiety that, when attached to another molecule, renders the latter colored and thus visible when various spectrophotometric measurements are applied.

The term "bioluminescent agent" describes a substance which emits light by a biochemical process.

The term "chemiluminescent agent" describes a substance which emits light as the result of a chemical reaction.

The phrase "fluorescent agent" refers to a compound that emits light at a specific wavelength during exposure to radiation from an external source.

The phrase "phosphorescent agent" refers to a compound emitting light without appreciable heat or external excitation as by slow oxidation of phosphorous.

A heavy metal cluster can be for example a cluster of gold atoms used, for example, for labeling in electron microscopy techniques.

As discussed hereinabove, the tumor vasculature possesses an enhanced capacity for the uptake of macromolecules and colloidal drug carriers having a high molecular weight and large hydrodynamic diameter due to the EPR effect. Therefore, a conjugate as described herein, having a large enough hydrodynamic diameter is beneficial. The term "large enough" is used herein to describe a conjugate having a hydrodynamic diameter which leads to an increase in the ratio of conjugate accumulated in the tumor tissue as compared to other tissues. The determination of the optimal ratio is well within the capability of those skilled in the art. For example, the ratio may be 1.1, 2, 3, 4, 5 etc. In some embodiments, the hydrodynamic diameter is in the range of from 3 nm to 200 nm. In some embodiments, the hydrodynamic diameter is in the range of from 3 nm to 100 nm. In some embodiments the hydrodynamic diameter is in the range of from 3 nm to 50 nm. In yet another embodiment the hydrodynamic diameter is in the range of from 3 nm to 20 nm.

The hydrodynamic diameter can be measured as described below under the Materials and Methods of the Example section which follows hereinbelow.

The conjugates described hereinabove may be administered or otherwise utilized in this and other aspects of the present invention, either as is, or as a pharmaceutically acceptable salt, enantiomer, diastereomer, solvate, hydrate or a prodrug thereof.

The phrase "pharmaceutically acceptable salt" refers to a charged species of the parent compound and its counter ion, which is typically used to modify the solubility characteristics of the parent compound and/or to reduce any significant irritation to an organism by the parent compound, while not abrogating the biological activity and properties of the administered compound. The neutral forms of the compounds are preferably regenerated by contacting the salt with a base or acid and isolating the parent compound in a conventional manner. The parent form of the compound differs from the various salt forms in certain physical properties, such as solubility in polar solvents, but otherwise the salts are equivalent to the parent form of the compound for the purposes of the present invention.

The phrase "pharmaceutically acceptable salts" is meant to encompass salts of the moieties and/or conjugates which are prepared with relatively nontoxic acids or bases, depending on the particular substituents found on the compounds described herein. When conjugates of the present invention contain relatively acidic functionalities, base addition salts can be obtained by contacting the neutral (i.e., non-ionized) form of such conjugates with a sufficient amount of the desired base, either neat or in a suitable inert solvent. Examples of pharmaceutically acceptable base addition salts include sodium, potassium, calcium, ammonium, organic amino, or magnesium salt, or a similar salt. When conjugates of the present invention contain relatively basic functionalities, acid addition salts can be obtained by contacting the neutral form of such conjugates with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", Journal of Pharmaceutical Science, 1977, 66, 1-19). Certain specific conjugates of the present invention contain both basic and acidic functionalities that allow the conjugates to be converted into either base or acid addition salts.

The neutral forms of the conjugates are preferably regenerated by contacting the salt with a base or acid and isolating the parent conjugate in a conventional manner. The parent form of the conjugate differs from the various salt forms in certain physical properties, such as solubility in polar solvents, but otherwise the salts are equivalent to the parent form of the conjugate for the purposes of the present invention.

In an example, a pharmaceutically acceptable salt of PGA is utilized. An exemplary such salt is a sodium salt.

The term "prodrug" refers to an agent, which is converted into the active compound (the active parent drug) in vivo. Prodrugs are typically useful for facilitating the administration of the parent drug. The prodrug may also have improved solubility as compared with the parent drug in pharmaceutical compositions. Prodrugs are also often used to achieve a sustained release of the active compound in vivo.

The conjugates described herein may possess asymmetric carbon atoms (optical centers) or double bonds; the racemates, diastereomers, geometric isomers and individual isomers are encompassed within the scope of the present invention.

As used herein, the term "enantiomer" describes a stereoisomer of a compound that is superposable with respect to its counterpart only by a complete inversion/reflection (mirror image) of each other. Enantiomers are said to have "handedness" since they refer to each other like the right and left hand. Enantiomers have identical chemical and physical properties except when present in an environment which by itself has handedness, such as all living systems.

The conjugates described herein can exist in unsolvated forms as well as solvated forms, including hydrated forms. In general, the solvated forms are equivalent to unsolvated forms and are encompassed within the scope of the present invention.

The term "solvate" refers to a complex of variable stoichiometry (e.g., di-, tri-, tetra-, penta-, hexa-, and so on), which is formed by a solute (the conjugate described herein) and a solvent, whereby the solvent does not interfere with the biological activity of the solute. Suitable solvents include, for example, ethanol, acetic acid and the like.

The term "hydrate" refers to a solvate, as defined hereinabove, where the solvent is water.

Certain conjugates of the present invention may exist in multiple crystalline or amorphous forms. In general, all physical forms are equivalent for the uses contemplated by the present invention and are intended to be within the scope of the present invention.

As described hereinabove, the conjugates described herein are capable of inhibiting angiogenesis and/or cell proliferation and therefore can be utilized for the treatment of conditions characterized by pathologically excessive angiogenesis and/or conditions where the inhibition of angiogenesis and/or cell proliferation is beneficial.

Thus, according to another aspect of embodiments of the invention there is provided a method of treating cancer and/or a medical condition associated with angiogenesis in a subject in need thereof. The method is effected by administering to the subject a therapeutically effective amount of any of the conjugates described herein.

Accordingly, according to another aspect of some embodiments of the present invention there are provided uses of the conjugates described herein as a medicament. In some embodiments, the medicament is for treating cancer and/or a medical condition associated with angiogenesis.

According to another aspect of some embodiments of the present invention, the conjugates described herein are identified for use in the treatment of a medical condition associated with angiogenesis and/or cancer.

As used herein, the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is understood that the conjugates of the present invention may be administered in conjunction with other drugs, including other anti-cancer and anti-angiogenic drugs. Such combinations are known in the art.

When the treatable condition is cancer the term would encompass any inhibition of tumor growth or metastasis, or any attempt to inhibit, slow or abrogate tumor growth or metastasis. The method includes killing cancer cells by non-apoptotic as well as apoptotic mechanisms of cell death.

It is noted herein that by targeting a therapeutically active agent via the methodologies described herein, the toxicity of the therapeutically active agent is substantially reduced, due to the conjugate selectivity towards sites of excessive angiogenesis. Consequently, besides the use of the conjugates described herein in a clinically evident disease, optionally in combination with other drugs, these conjugates may potentially be used as a long term-prophylactic for individuals who are at risk for relapse due to residual dormant cancers. The use of non-toxic targeted conjugates for the treatment of asymptomatic individuals who are at risk for relapse of a cancer, may lead to a major paradigm shift in cancer treatment from current methods where treatment is generally not initiated until the cancer becomes clinically evident.

The term "cancer cells" describes a group of cells which display uncontrolled growth (division beyond the normal limits).

The phrase "therapeutically effective amount" describes the amount of a compound which is sufficient to effect treatment when administered to a subject in need of such treatment or prevention. As used herein this phrase describes the amount of conjugate which is sufficient to reduce or prevent angiogenesis (i.e. inhibit the formation of new blood vessels in a tissue) and/or cell proliferation and/or kill preexisting cancer cells in tissue.

Medical conditions associated with angiogenesis and which are treatable by the conjugates described herein include, but are not limited to, atherosclerosis, cancer, hypertension, rheumatoid arthritis, diabetes and diabetes related complications such as diabetic retinopathy and macular degeneration (MD). The terms "cancer" and "tumor" are used interchangeably herein to describe a class of diseases in which a group of cells display uncontrolled growth (division beyond the normal limits). The term "cancer" encompasses malignant and benign tumors as well as disease conditions evolving from primary or secondary tumors. The term "malignant tumor" describes a tumor which is not self-limited in its growth, is capable of invading into adjacent tissues, and may be capable of spreading to distant tissues (metastasizing). The term "benign tumor" describes a tumor which is not malignant (i.e. does not grow in an unlimited, aggressive manner, does not invade surrounding tissues, and does not metastasize). The term "primary tumor" describes a tumor that is at the original site where it first arose. The term "secondary tumor" describes a tumor that has spread from its original (primary) site of growth to another site, close to or distant from the primary site.

Cancers treatable by the conjugates described herein include, but are not limited to, solid, including carcinomas, and non-solid, including hematologic malignancies. Carcinomas include and are not limited adenocarcinomas and epithelial carcinomas. Hematologic malignancies include leukemias, lymphomas, and multiple myelomas. The following are non-limiting examples of the cancers treatable with the conjugates described herein: ovarian, pancreas, brain, colon, rectal, colorectal, melanoma, lung, breast, kidney (renal), and prostate cancers.

The term "cancer metastases" describes cancer cells which have "broken away", "leaked", or "spilled" from a primary tumor, entered the lymphatic and/or blood vessels, circulated through the lymphatic system and/or bloodstream, settled down and proliferated within normal tissues elsewhere in the body thereby creating a secondary tumor.

According to another aspect of some embodiments of the present invention there are provided uses of any of the conjugates described herein, having a labeling agent as described herein, as diagnostic agents and/or in the manufacture of a diagnostic agent for monitoring cancer and/or a medical condition associated with angiogenesis.

According to another aspect of some embodiments of the present invention, each of the conjugates described herein, which comprises a labeling agent, is identified for use a diagnostic agent, for monitoring cancer and/or a medical condition associated with angiogenesis.

Suitable imaging techniques include but are not limited to positron emission tomography (PET), gamma-scintigraphy, magnetic resonance imaging (MRI), functional magnetic resonance imaging (fMRI), magnetoencephalography (MEG), single photon emission computerized tomography (SPECT) computed axial tomography (CAT) scans, ultrasound, fluoroscopy and conventional X-ray imaging. The choice of an appropriate imaging technique depends on the nature of the labeling agent, and is within the skill in the art. For example, if the labeling agent comprises Gd ions, then the appropriate imaging technique is MRI; if the labeling agent comprises radionuclides, an appropriate imaging technique is gamma-scintigraphy; if the labeling agent comprises an ultrasound agent, ultrasound is the appropriate imaging technique, etc.

According to another aspect of embodiments of the invention there is provided a pharmaceutical composition comprising, as an active ingredient, any of the conjugates described herein and a pharmaceutically acceptable carrier.

Accordingly, in any of the methods and uses described herein, any of the conjugates described herein can be provided to an individual either per se, or as part of a pharmaceutical composition where it is mixed with a pharmaceutically acceptable carrier.

As used herein a "pharmaceutical composition" refers to a preparation of one or more of the conjugates described herein (as active ingredient), or physiologically acceptable salts or prodrugs thereof, with other chemical components including but not limited to physiologically suitable carriers, excipients, lubricants, buffering agents, antibacterial agents, bulking agents (e.g. mannitol), antioxidants (e.g., ascorbic acid or sodium bisulfite), anti-inflammatory agents, antiviral agents, chemotherapeutic agents, anti-histamines and the like. The purpose of a pharmaceutical composition is to facilitate administration of a compound to a subject. The term "active ingredient" refers to a compound, which is accountable for a biological effect.

The terms "physiologically acceptable carrier" and "pharmaceutically acceptable carrier" which may be interchangeably used refer to a carrier or a diluent that does not cause significant irritation to an organism and does not abrogate the biological activity and properties of the administered compound.

Herein the term "excipient" refers to an inert substance added to a pharmaceutical composition to further facilitate administration of a drug. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences" Mack Publishing Co., Easton, Pa., latest edition, which is incorporated herein by reference.

Pharmaceutical compositions for use in accordance with the present invention thus may be formulated in conventional manner using one or more pharmaceutically acceptable carriers comprising excipients and auxiliaries, which facilitate processing of the compounds into preparations which can be used pharmaceutically. Proper formulation is dependent upon the route of administration chosen. The dosage may vary depending upon the dosage form employed and the route of administration utilized. The exact formulation, route of administration and dosage can be chosen by the individual physician in view of the patient's condition (see e.g., Fingl et al., 1975, in "The Pharmacological Basis of Therapeutics", Ch. 1 p. 1).

The pharmaceutical composition may be formulated for administration in either one or more of routes depending on whether local or systemic treatment or administration is of choice, and on the area to be treated. Administration may be done orally, by inhalation, or parenterally, for example by intravenous drip or intraperitoneal, subcutaneous, intramuscular or intravenous injection, or topically (including ophthalmically, vaginally, rectally, intranasally, intrathecally).

Formulations for topical administration may include but are not limited to lotions, ointments, gels, creams, suppositories, drops, liquids, sprays and powders. Conventional pharmaceutical carriers, aqueous, powder or oily bases, thickeners and the like may be necessary or desirable.

Compositions for oral administration include powders or granules, suspensions or solutions in water or non-aqueous media, sachets, pills, caplets, capsules or tablets. Thickeners, diluents, flavorings, dispersing aids, emulsifiers or binders may be desirable.

Formulations for parenteral administration may include, but are not limited to, sterile solutions which may also contain buffers, diluents and other suitable additives. Slow release compositions are envisaged for treatment.

The amount of a composition to be administered will, of course, be dependent on the subject being treated, the severity of the affliction, the manner of administration, the judgment of the prescribing physician, etc.

The pharmaceutical composition may further comprise additional pharmaceutically active or inactive agents such as, but not limited to, an anti-bacterial agent, an antioxidant, a buffering agent, a bulking agent, a surfactant, an anti-inflammatory agent, an anti-viral agent, a chemotherapeutic agent and an anti-histamine.

According to an embodiment of the present invention, the pharmaceutical composition described hereinabove is packaged in a packaging material and identified in print, in or on the packaging material, for use in the treatment of cancer and/or a medical condition associated with angiogenesis.

According to another embodiment of the present invention, the pharmaceutical composition is packaged in a packaging material and identified in print, in or on the packaging material, for use in monitoring cancer and/or a medical condition associated with angiogenesis.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert.

Further according to embodiments of the present invention there are provided processes of preparing any of the conjugates described herein. Exemplary processes are effected via living polymerization, such as RAFT polymerization. Exemplary processes are described in the Examples section that follows.

Conjugates can be prepared by attaching the agents/moieties to the backbone units of already polymerized monomers or by attaching each of the agents/moieties to monomeric units and then polymerizing the monomeric units, or by any combination of the above.

Exemplary processes are presented in the Examples section that follows and accompanying Figures.

In general, polymerization technique is selected so as to allow controlling on the degree of polymerization and/or on the load of the moieties that are attached to the backbone. Exemplary techniques include RAFT polymerization, which is suitable for example for HPMA polymeric backbones, and NCT polymerization, which is suitable for PGA polymeric backbones.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non-limiting fashion.

Materials and Methods

Materials:
Paclitaxel (PTX), doxorubicin (DOX) and alendronate (ALN) were purchased from Petrus chemicals.
TNP-470 was purchased from Sigma-Aldrich.
All other chemicals were purchased from known vendors unless otherwise indicated.
Cell Cultures:
Human umbilical vein endothelial cells (HUVECs) were isolated from umbilical cords and were cultured in EGM-2 media.
DA3 cells were derived from the D1-DMBA-3 transplantable mammary tumor and obtained from a laboratory in Tel Aviv University, Israel and were cultured in DMEM supplemented with 10% FBS, 100 μg/ml penicillin, 100 U/ml streptomycin, 12.5 U/ml nystatin.

HeLa HiFR cells were derived from HeLa cells (purchased from the ATCC) by culturing in folate-depleted media for several passages within 3 weeks and were cultured in DMEM-folate-depleted supplemented with 10% FBS, 100 μg/ml penicillin, 100 U/ml streptomycin, 12.5 U/ml nystatin.

Saos2 human osteosarcoma cells were purchased from American Tissue Culture Collection (ATCC).

ES-2 human ovarian carcinoma cells were purchased from the ATCC.

ES-2 and Saos2 cells were cultured in DMEM supplemented with 10% FBS, 100 μg/ml penicillin, 100 U/ml streptomycin, 12.5 U/ml nystatin and 2 mM L-glutamine, and for Saos2 cells also with 1 mM sodium pyruvate.

Human MDA-MB-231 cells were purchased from American Tissue Culture Collection (ATCC), and were cultured in DMEM supplemented with 10% FBS, 100 μg/ml penicillin, 100 U/ml streptomycin, 12.5 U/ml nystatin. All Cells were grown at 37° C., 5% $CO_2$.

Cell Proliferation Assay:
In an exemplary procedure, cells were plated onto 96-well plates in appropriate complete medium for each cell line as described above, and incubated for 24 hours (37° C.; 5% $CO_2$). On the following day cells were treated with e.g., paclitaxel at various concentrations (e.g., 0.0001, 0.001, 0.01, 0.1, 1, 10, 100, 1000, 10,000 nM) or, e.g., doxorubicin at various concentrations (e.g., 0.001, 0.001, 0.01, 0.1, 1, 10, 100, 1000, 10,000, 100,000 nM) for 72 hours. After incubation cell viability was determined by MTT assay.

For evaluating anti-proliferative activity of a combination of PTX and DOX, cells were treated with varying concentrations of DOX with a set concentration of PTX or varying concentrations of PTX with a set concentration of DOX.

Selected inhibition concentration values (e.g., $IC_{50}$, $IC_{40}$, $IC_{60}$ and $IC_{80}$ values (growth inhibition by 50, 40, 60 and 80% respectively) were derived from the obtained growth charts.

Same procedure was followed for other drugs and combination treatments.

Evaluation of Synergism:
In an exemplary procedure, selected inhibition concentration values (e.g., $IC_{40}$, $IC_{60}$ and $IC_{80}$) of PTX, DOX and combinations thereof from a respective cell proliferation assay were collected. The selected inhibition concentration values of DOX and PTX were marked on X and Y axes respectively and a line which represents additive effect was drawn between each inhibitory concentration (IC). The combination index (CI) of each treatment was calculated according to the classic isobologram equation $CI=[(D)1/(Dx)1]+[(D)2/(Dx)2]$. Area on the right side of each IC additive line represents antagonist effect and area on the left side represents synergistic effect. In other words, CI of 1 represents additive effect, CI>1 antagonistic effect and CI<1 synergistic effect.

The same procedure was followed when other combination treatments were tested.

Solid Phase Peptide Synthesis (SPPS):
NCAM-targeting peptide (NTP) with the sequence GDDSDEEN and scrambled peptide with the sequence GESDDEND were synthesized using solid phase peptide synthesis (SPPS) method. Amino acids, protected at α-amine and side chains (Chem-Impex Int.) were added in a sequential manner from C-terminal to N-terminal on 2-chlorotrityl chloride resin. The first coupling step to resin was done in dry dichloromethane (Sigma-Aldrich) and all additional coupling steps were done in dimethylformamide (DMF, Sigma-Aldrich). Amino acids were activated at the C-terminal with O-Benzotriazole-N,N,N',N'-tetramethyl-uronium-hexafluoro-phosphate (HBTU, Chem-Impex Int.) and N,N-Diisopropylethylamine (DIPEA, Sigma-Aldrich) was added as a base. The amino protecting Fmoc group was removed to reveal a new N-terminal amine using 25% piperidine (Sigma-Aldrich) in DMF. The procedure was continued until the desired sequence was obtained. The removal of side-chain protecting groups and the cleavage of the peptide from the resin was done by incubating the resin with mixture of trifluoroacetic acid (TFA, Sigma-Aldrich), deionized water and triisopropylsilane (TIS, Sigma-Aldrich) (95:2.5:2.5). The product was precipitated using cold ether (Bio-Lab, Israel) and washed twice in cold ether, dissolved in deionized water and lyophilized.

The same procedure was followed for SPPS of other peptides.

Fast Protein Liquid Chromatography (FPLC):

FPLC (AKTA) equipped with UV detector was used for preparative separation of various substances.

Small molecules were separated by reversed phase chromatography, using Jupiter C-18 RP, 5 µm, 250×21.20 mm column (Phenomenex).

Polymers were separated from small molecules by size exclusion chromatography using 200 ml column packed with sephadex G75, with water as eluent.

High Pressure Liquid Chromatography (HPLC):

Analytical HPLC was used for the characterization of the various substances. UltiMate® 3000 Nano LC systems (Dionex) was used equipped with 3000 pump, VWD-3000 UV-Vis detector and Chromeleon® 6.80 software. The column is LiChroCART® 250-4,6 Purospher® STAR (5 µm) C-18 RP (reverse phase). Chromatographic conditions: flow: 1.0 ml/min, gradient: 1% sol. B to 90% sol. B in 20 minutes (solution A—0.1% TFA in water; solution B—0.1% TFA in ACN).

Mass Spectroscopy (MS):

Mass of peptides and fluorescein-labeled peptides was determined by MS, to confirm that the correct product was obtained. Samples were dissolved in methanol or acetonitrile for analysis.

Nuclear Magnetic Resonance (NMR):

NMR spectroscopy was performed on 200 MHz Avance, Bruker (Karlshruhe, Germany) system. The samples were dissolved in $CDCl_3$.

Quantitative Evaluation of Conjugate Hydrodynamic Diameter:

The mean hydrodynamic diameter of a polymeric conjugate is evaluated using a real time particle analyzer (NanoSight LM20™) containing a solid-state, single mode laser diode (<20 mW, 655 nm) configured to launch a finely focused beam through a 500 µL sample chamber. The particles dynamics are visualized at 30 frames per second (fps) for 30 sec at 640×480 resolution by the device CCD camera. The paths the particles take under Brownian motion over time are analyzed using Nanoparticle Tracking Analysis (NTA) software.

FACS Analysis:

Cells were washed with PBS, harvested using a cell scraper and labeled by incubation with APC-conjugated CD-56 antibody (Biolegend) for 45 min at 4° C. in the dark. Cells were washed three times with PBS and filtrated with 100 µm cell strainer (BD Falcon).

FACS Sorting:

Cells were harvested and labeled as described above, and resuspended in the appropriate cell culture medium (according to cell type) with 5% FBS. Cells were filtrated with 100 µm cell strainer before sorting. Sorted cells were collected into tubes containing complete medium with 0.5 mg/ml gentamycin (Biological Industries, Israel). All work was done in sterile conditions.

Sphere Formation Assay:

Cells were plated in 6-well plates coated with poly(2-hydroxyethyl methacrylate) to prevent adhesion, in a medium consisting of Knockout DMEM, 20% FBS, 10% non-essential amino acids (Gibco-Invitrogen), 100 µg/ml Penicillin, 100 U/ml Streptomycin, 12.5 U/ml Nystatin, 2 mM L-glutamine, 100 ng/ml EGF, 100 ng/ml bFGF and 10 ng/ml SCF (Peprotech Asia, Israel) at concentration of 50,000 cells/well. After 5-7 days sphere formation was evaluated.

Clonogenicity Assay:

Cells were plated onto 96-well plates in complete medium at concentration of 1 cell/well. Number of colonies was counted after 2 weeks for ES2 cells and after 4 weeks for SK N MC cells.

Capillary-Like Tube Formation Assay:

The surface of 24-well plates is coated with Cultrex® basement membrane (50 µl/well; 10 mg/ml) on ice and then allowed to polymerize at 37° C. for 30 minutes. HUVECs ($3\times10^4$) are seeded on coated plates in the presence of conditioned media of tumor cells treated with the conjugate and its controls. After 8 hours of incubation (37° C.; 5% $CO_2$), wells are imaged using bright-field technique (Nikon TE2000E inverted microscope integrated with Nikon DS5 cooled CCD camera by 4× objective).

Migration Assay:

Cell migration assays are performed using modified 8 µm Boyden chambers (Transwell-Costar Corp.) coated with 10 µg/ml fibronectin. Cells are allowed to migrate towards conditioned media of tumor cells treated with the conjugate and its controls to the underside of the chamber. Cells are fixed and stained (Hema 3 Stain System; Fisher Diagnostics). The number of migrated cells per membrane is captured using bright-field microscopy connected to a spot digital camera (Diagnostic Instruments) and counted using NIH ImageJ software.

Confocal Microscopy:

Cell specificity and uptake of the fluorescently labeled peptides was monitored utilizing a Zeiss Meta LSM 510 confocal imaging system. Cells were plated on glass slides and incubated overnight. The following day cells were incubated with 100 µM of CF-NTP or CF-scrambled peptide for 30 minutes at 37° C., washed several times with PBS, fixated with 4% paraformaldehyde, stained with Hoechst stain and mounted on slides. In order to examine intracellular trafficking of the peptide, cells were incubated with the peptides in serum free medium, washed several times with cold PBS and incubated with 40 mg/ml AlexaFluor 594 human transferrin for 1 h at 37° C. Cells were washed several times with PBS, fixated with 4% PFA, stained with Hoechst stain and mounted on slides.

Example 1

PTX and DOX Combination Treatment

Experimental Results

Effect of Doxorubicin and Paclitaxel Combination Treatment on HUVECs Proliferation:

The effect of PTX at various concentrations (0.0001, 0.001, 0.01, 0.1, 1, 10, 100, 1000, and 10,000 nM), and of doxorubicin at various concentrations (0.001, 0.001, 0.01, 0.1, 1, 10, 100, 1000, 10,000, 100,000 nM) on the proliferation of HUVEC p3 cells was tested. The obtained data is presented in FIG. 1A for PTX and in FIG. 1B for DOX.

For evaluating the effect of the combination treatment, 0.1 or 1 nM DOX with various concentrations of PTX and 0.1 or 1 nM PTX with various concentrations of DOX were tested.

FIG. 2 presents comparative plots showing the effect of PTX and DOX, each alone and in various combinations thereof, on the proliferation of HUVECs.

The corresponding $IC_{50}$ values are presented in Table 1 below.

TABLE 1

|  | $IC_{50}$ [nM] |
|---|---|
| DOX | 40 |
| DOX + 0.1 nM PTX | 20 |
| DOX + 1 nM PTX | 10 |
| PTX | 7 |
| PTX + 0.1 nM DOX | 5 |
| PTX + 1 nM DOX | 3 |

The corresponding $IC_{40}$, $IC_{60}$ and $IC_{80}$ values of 2 sets of combinations (for 0.1 nM DOX and 0.1 nM PTX) are presented in Table 2 below.

TABLE 2

| COMBINATION I (PTX + DOX 0.1 nM) | | | | COMBINATION II (DOX + PTX 0.1 nM) | | | |
|---|---|---|---|---|---|---|---|
| IC | DOX (nM) | PTX (nM) | CI | IC | DOX (nM) | PTX (nM) | CI |
| 40 | 0.1 | 4 | 0.805 | 40 | 20 | 0.1 | 1.020 |
| 60 | 0.1 | 8 | 0.802 | 60 | 40 | 0.1 | 0.810 |
| 80 | 0.1 | 40 | 0.401 | 80 | 80 | 0.1 | 0.801 |

FIG. 3A presents the corresponding isobolograms demonstrating the synergistic effect exhibited by the PTX and DOX combination, and clearly show the synergistic effect exhibited at all tested combinations.

Additional studies were performed on HeLa HiFR cells treated with PTX, DOX and a combination thereof, and demonstrated an additive and/or synergistic effect of the combined treatment. Data is presented in FIGS. 2B and 3B and in Table 3 below.

TABLE 3

| COMBINATION I (PTX + DOX 10 nM) | | | | COMBINATION II (DOX + PTX 1 nM) | | | |
|---|---|---|---|---|---|---|---|
| IC | DOX (nM) | PTX (nM) | CI | IC | DOX (nM) | PTX (nM) | CI |
| 40 | 1 | 10 | 0.500 | 40 | 3000 | 0.1 | 1.005 |
| 60 | 1 | 30 | 0.750 | 60 | 5000 | 0.1 | 1.003 |
| 80 | 1 | 75 | 0.500 | 80 | 9000 | 0.1 | 1.001 |

Effect of Doxorubicin and Paclitaxel Combination Treatment on the Proliferation of ES2 and Saos2 Cells:

The effect of DOX and PTX combinations on viability of ES2 and Saos2 cells was examined. Cells were treated with PTX alone, DOX alone, varying concentrations of DOX with a set concentration of PTX (10 or 50 nM for ES2, 1 nM for Saos2) or varying concentrations of PTX with a set concentration of DOX (10 or 50 nM). $IC_{20}$, $IC_{40}$ and $IC_{60}$ values (growth inhibition by 20, 40 and 60% respectively) were derived from the growth charts and combination index (CI) values were calculated.

FIG. 4A presents the effect of PTX and DOX, each alone and in combination, on the viability of human ovarian carcinoma ES-2 cells.

FIG. 4B presents isobolograms demonstrating the synergistic effect exhibited by the PTX and DOX combination on ES-2 cells.

FIG. 5A presents the effect of PTX and DOX, each alone and in combination, on the viability of human osteosarcoma Saos-2 cells.

FIG. 5B presents isobolograms demonstrating the synergistic effect exhibited by the PTX and DOX combination on human osteosarcoma Saos-2 cells.

Overall, the obtained data clearly demonstrate a synergism between PTX and DOX in both cell lines.

Effect of Doxorubicin and Paclitaxel Combination Treatment on MDA-MB-231 Cells Proliferation.

The effect of PTX, DOX and combinations thereof on the proliferation of human MDA-MB-231 cells was tested. Several concentrations and PTX/DOX ratios were tested, and the obtained data showed that the combination treatment of PTX and DOX decreased the IC's of the drugs as single treatments.

FIG. 6A presents the results obtained for PTX and DOX, each alone, at various concentrations within a range of 0.01-10000 nM, and for various concentrations of PTX with 20 nM DOX, and for various concentrations of DOX with 1 nM PTX. As can be seen in FIG. 6A, PTX inhibited cells proliferation at IC 20, 40, 60 of 2.5, 7, 100 nM, respectively, and DOX at 60, 250, 950 nM. Data represents mean±SD.

In order to evaluate the combination treatment effect, data from combination treatment results were collected, analyzed and calculated according to CI equations. The results are presented in Table 4 below and in FIG. 6B. Combination treatments I (PTX+DOX 20 nM) and II (DOX+PTX 1 nM) inhibited MDA-MB-231 cells proliferation of IC 20, 40, 60 at 0.8, 4, 25 and 4, 150, 700 nM respectively. These combination treatments of PTX and DOX have synergistic effect on MDA-MB-231 proliferation.

TABLE 4

| IC | DOX (nM) | PTX (nM) | CI |
|---|---|---|---|
| COMBINATION I (PTX + DOX 20 nM) | | | |
| 20 | 20 | 0.8 | 0.653 |
| 40 | 20 | 4 | 0.651 |
| 60 | 20 | 25 | 0.271 |
| COMBINATION II (DOX + PTX 1 nM) | | | |
| 20 | 4 | 1 | 0.467 |
| 40 | 150 | 1 | 0.743 |
| 60 | 700 | 1 | 0.747 |

Example 2

Paclitaxel and TNP-470 Combination Treatment

The effect of PTX at various concentrations, TNP-470 at various concentrations and of various combinations of a set concentration of PTX and variable concentrations of TNP-470 and a set concentration of TNP-470 and variable concentrations of PTX, on proliferation of HUVECs, was tested. Similar assays were performed in the presence of 10,000 nM alendronate. The obtained data is presented in FIG. 7A (no alendronate) and in FIG. 7B (in the presence of alendronate).

The synergism of the drugs combination was calculated as described hereinabove.

Table 5 below presents exemplary calculations made for TNP-470 at 0.0001 nM and PTX as the variable treatment.

FIGS. 8A-C present the corresponding isobologram analyses.

Table 6 below presents additional calculations made for various ratios of PTX and TNP-470.

TABLE 5

| CI | TNP (nM) | PTX (nM) | IC |
|---|---|---|---|
| 1 | 0.0001 | 0.0000001 | 60 |
| 0.001 | 0.0001 | 0.000001 | 70 |
| 0.0001 | 0.0001 | 0.7 | 90 |

TABLE 6

| TNP-470:PTX | CI | PTX (nM) | TNP-470 (nM) |
|---|---|---|---|
| 1:100 | 0.5 | 1 | 0.01 |
| 10:1 | 0.25 | 0.0001 | 0.001 |
| 1:10,000 | 0.01 | 100 | 0.01 |
| 1:50 | 0.001 | 0.05 | 0.001 |
| 1:4,000 | 0.001 | 4 | 0.001 |
| 100:1 | 0.001 | 0.000001 | 0.0001 |
| 1:2000 | 0.0003 | 2 | 0.001 |
| 1:1000 | 0.0001 | 0.7 | 0.0001 |

The obtained data show synergism at high concentrations of PTX; and an additive effect (CI=1) at low concentrations of PTX. The data further show that a synergistic effect (CI<1) is seen at variable concentration ratios of TNP-470 and PTX, with the highest synergistic effect seen in ratios of 1:1000-2000 (TNP-470:PTX).

Calculations made for TNP-470 as the variable treatment are shown in Table 7 below.

TABLE 7

| CI | PTX (nM) | TNP470 (nM) | IC |
|---|---|---|---|
| 0.3 | 0.00001 | 6,000 | 30 |
| 0.75 | 0.00001 | 30,000 | 50 |
| 1 | 0.00001 | 70,000 | 70 |

FIG. 10 presents the corresponding isobologram analysis.

Table 8 below presents additional calculations made for various ratios of PTX and TNP-470.

TABLE 8

| TNP-470:PTX | CI | PTX (nM) | TNP-470 (nM) |
|---|---|---|---|
| $7 \times 10^9$:1 | 1 | 0.00001 | 70,000 |
| $4 \times 10^5$:1 | 1 | 0.00001 | 4 |
| $5 \times 10^8$:1 | 1 | 0.00001 | 5000 |
| $3 \times 10^9$:1 | 0.75 | 0.00001 | 30,000 |
| $1.5 \times 10^8$:1 | 0.5 | 0.00001 | 1500 |
| $6 \times 10^8$:1 | 0.3 | 0.00001 | 6000 |

The obtained data show an additive effect at high concentrations of TNP-470; and synergism at low concentrations of TNP-470.

It is further shown that all combinations of TNP-470 and 0.00001 nM PTX demonstrated synergism/additive effect, with the strongest synergistic effect seen in ratios of about $10^8$:1 (TNP-470:PTX).

Example 3

Conjugates Comprising HPMA Having Attached Thereto PTX and DOX or PTX and TNP-470

In some embodiments, conjugates comprising HPMA having attached thereto two drugs and optionally a targeting moiety and/or a labeling moiety (e.g., FITC), are prepared using a reversible addition-fragmentation chain transfer (RAFT) polymerization technique.

In some embodiments, RAFT polymerization is effected while dissolving in water functionalized and non-functionalized monomeric MA units, and optionally also HPMA, in the presence of 2,2'-Azobis[2-(2-imidazolin-2-yl)propane] dihydrochloride (VA-044) as an initiator and S,S'-bis($\alpha,\alpha'$-dimethyl-$\alpha''$-acetic acid) trithiocarbonate as a chain transfer agent (TTC). The solution is bubbled with nitrogen for 30 minutes, sealed in ampoule, and co-polymerization is performed at 30° C.

In some embodiments, some of the functionalized monomeric MA units have one drug attached thereto and some of the functionalized MA monomeric units have another drug attached thereto. In some embodiments, in the obtained HPMA conjugate, one or both drugs are attached to the polymeric backbone units via a linker.

In some embodiments, the MA monomeric units used in the polymerization have a linker suitable for attaching a drug thereto. In these embodiments, the drug is conjugated to the obtained polymer. In some embodiments, the MA monomeric units have the drug attached thereto via a suitable linker, and are then subjected to polymerization.

The obtained polymers are purified by being dissolved in water and precipitated into an excess of acetone. Further work-up procedures can be performed to remove excess of reactants. The sample is freeze-dried after dialysis.

FIGS. 11A-11F present chemical structures of, and synthetic routes for, preparing, exemplary conjugates of HPMA copolymer having attached thereto TNP-470 and PTX, via various linkers, optionally further having a targeting moiety attached to the copolymer, by RAFT polymerization, according to some embodiments of the present invention.

FIGS. 12A-12F present the chemical structures of, and synthetic routes for preparing, conjugates of HPMA copolymer having attached thereto Doxorubicin (DOX) and paclitaxel (PTX), via various linkers, optionally having a targeting moiety (e.g., RGD-containing moiety) attached to the polymer via a linker, according to some embodiments of the present invention. Conjugates are prepared while using RAFT polymerization.

FIGS. 13-15 describe the synthetic steps for preparing a HPMA-PTX-DOX conjugate, according to some embodiments of the present invention, as follows:

FIGS. 13A-B describe the syntheses of exemplary MA monomers having a linker attached thereto according to some embodiments of the present invention.

FIG. 14A presents the BOC-protected PTX-linker molecule obtained by coupling PTX to FK linker via p-aminobenzylalcohol (PABA). In brief, Boc-Phe-p-nitrophenyl (PNP) was coupled with Lys(Alloc)-OH, the obtained Boc-FK(Alloc)-PNP was coupled to p-aminobenzylalcohol (PABA), and the obtained Boc-FK-PABC-PNP was coupled to PTX. The product was characterized by analytical HPLC, $^1$H-NMR and mass spectroscopy. FIG. 14B presents the coupling of PTX to the MA-linker described in FIG. 13B. In brief, the peptide MA-GFLG-OH was activated with coupling reagent (DCC/EDC) and N-hydroxy succinimide (NHS), the BocPG-protecting group was removed from Boc-FK-PABC-PTX, and the two fragments were coupled in DMF and Et₃N, to thereby obtain a MA monomer having a PTX molecule attached thereto via a linker, according to some embodiments of the present invention.

FIG. 15 presents the coupling of DOX to an activated MA-GFLG-OH monomeric unit in DMF.

The different MA monomers, substituted by PTX and DOX, are polymerized, in the presence of MA monomers, to thereby obtain the final copolymer.

Example 4

Conjugates Comprising PGA Having Attached Thereto PTX and DOX Chemical Syntheses PGA Synthesis:

PGA$_{100}$ was synthesized via the N-carboxyanhydride (NCA) polymerization of glutamic acid, as depicted in FIGS. 16A-B. First, NCA glutamate was prepared, using H-Glu(OBzl)-OH as a starting material (see, FIG. 16A). Following deprotection of the OBzl protecting group in TFA/HBr/AcOH mixture, the carboxyl group becomes available for coupling to the desired compounds. Then, polymerization of the NCA of the γ-benzyl-glutamate was initiated by R—NH$_2$ (e.g., diethylamine). FIG. 16B presents the first polymerization step. The reaction proceeds at the same manner. The length of the obtained polymer is determined by the amount of the initiator and the NCA. In an exemplary procedure, diethylamine, as an exemplary initiator, was added to NCA at molar ratio of 1:100 to obtain PGA$_{100}$ polymer. PGA was characterized by $^1$H-NMR and by FPLC. In order to render the polymer water soluble, a salt form of PGA was prepared by dissolving the PGA in 0.25M NaHCO$_3$ buffer and passing through sephadex G25 column using water as eluent.

FITC Labeling of PGA:

PGA was fluorescently labeled at the N-terminal of the polymer using fluorescein isothiocyanate (FITC), as depicted in FIG. 17. PGA salt and FITC at 5-folds molar excess were dissolved in 0.5M NaHCO$_3$ buffer with pH=9 and the reaction was allowed to proceed for 4 hours at room temperature. Following the incubation, FITC-PGA conjugate was separated from free FITC by FPLC using a sephadex G75 column, and a UV detector operated at 220 and 495 nm. The obtained FITC-PGA (retention time of about 30 minutes) was collected and the solution lyophilized to obtain the FITC-PGA conjugate as orange-yellow powder.

Synthesis of PGA-PTX Conjugate:

PTX was bound to the PGA backbone by carbodiimide coupling in DMF. PGA was dissolved in DMF and PTX and HBTU (activating agent) were added. Reaction was allowed to proceed under nitrogen for 24 hours. DMF was thereafter evaporated and the product was washed with chloroform: acetone 4:1 mixture.

Synthesis of PGA-DOX—Route 1:

DOX was attached to the PGA backbone through GLFG linker, as described herein and depicted in FIG. 18, by coupling DOX-GFLG (as described hereinabove) to PGA by carbodiimide coupling using Diisopropylcarbodiimide (DIC) and 1-hydroxy-benzotriazole (HOBt) in anhydrous DMF.

Synthesis of PGA-DOX—Route 2:

In an alternative strategy, DOX was attached to PGA through an acid-sensitive hydrazone bond, as depicted in FIG. 19. Cysteamine was bound to PGA, in order to introduce free SH groups to the PGA backbone, which are then utilized for DOX coupling. In parallel, DOX was coupled to acid-sensitive 3,3'-N-[ε-Maleimidocaproic acid] hydrazide (EMCH) linker (see, FIG. 19C). DOX-EMCH was coupled to PGA-SH, by selective reaction of the maleimide moiety of the linker with SH groups on PGA, to form the conjugate PGA-DOX.

Synthesis of PGA-DOX-PTX—Route 1:

A conjugate of PGA coupled to PTX and DOX as depicted in FIG. 18 was synthesized as follows: PTX was attached to PGA via a hydrolyzable ester bond, as described hereinabove for PGA-PTX, and DOX was attached through GFLG peptide linker cleavable by Cathepsin B, as described hereinabove for PGA-DOX. Loading of PTX was 6% mol and of DOX 6.8% mol, as determined indirectly by HPLC by analyzing the amounts of unbound drugs.

Figure 19A:
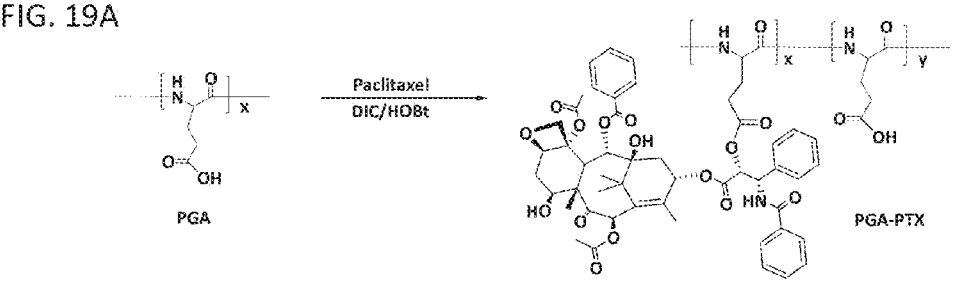
Figure 19B:
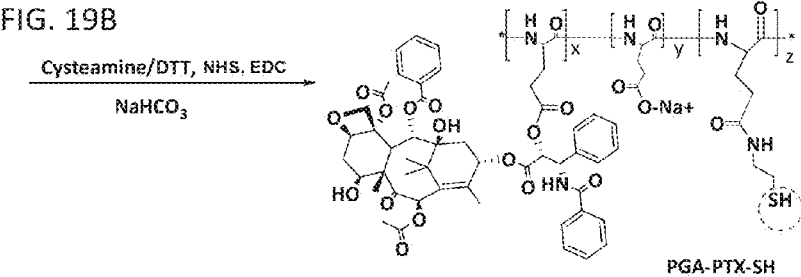
Figure 19C:
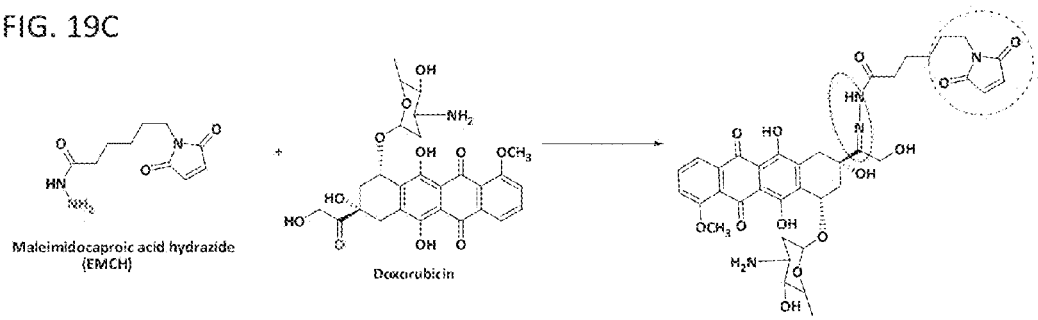
Figure 19D:
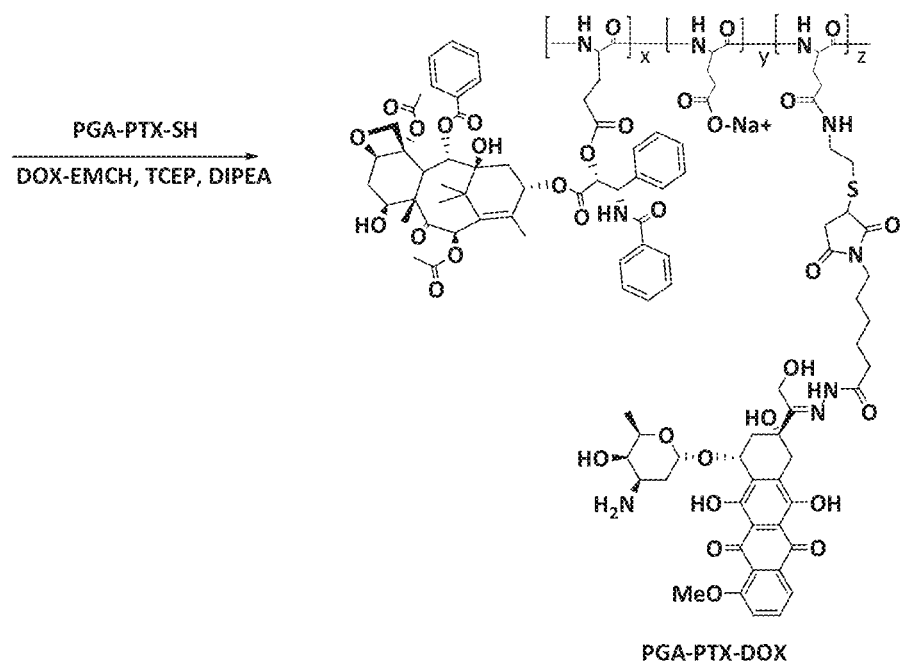

PGA-DOX-PTX Synthesis —Route 2:

A conjugate of PGA-PTX-DOX, in which DOX is bound through an acid-sensitive hydrazone linker and PTX is bound directly, via an ester bond, to the polyglutamic acid (PGA) polymer backbone was synthesized as depicted in FIGS. 19A-D. In brief, PTX was coupled to PGA as described hereinabove (FIG. 19A). Then cysteamine was conjugate to PGA to generate thiol groups (FIG. 19B). DOX was couples to EMCH so as to form a hydrazone bond (FIG. 19C), and the obtained DOX-EMCH was coupled to the PGA-PTX by selective reaction of the maleimide moiety with the thiol groups generated on the PGA-PTX conjugate (FIG. 19D).

Characterization of the conjugate was performed as follows:

PTX loading was determined by HPLC, by measuring the amount of unbound PTX in the reaction. DOX loading was determined by UV absorption using absorption constant of DOX-EMCH.

Table 9 below presents the physicochemical characterization of PGA-PTX, PGA-DOX (Route 2) and PGA-PTX-DOX (Route 2).

TABLE 9

| Conjugate | Zeta potential | Total PTX loading (% mol) | Total DOX loading (% mol) | Molecular weight (theoretical) |
|---|---|---|---|---|
| PGA-PTX | −30.4 | 13.5% | — | 26,089 |
| PGA-DOX | −35.9 | — | 2.8% | 17,306 |
| PGA-PTX-DOX | −27.3 | 2% | 5.0% | 20,668 |
| PGA | −42.5 | — | — | 15,100 |

Preparation of PGA-PTX-DOX-Targeting Moiety Conjugate:

Peptide-based targeting moieties are attached to a PGA-PTX-DOX conjugate as described herein by coupling the targeting peptide, via its N-terminus to the pendant carboxyl groups of PGA backbone units, so as to form an amide bond.

Figure 20D:
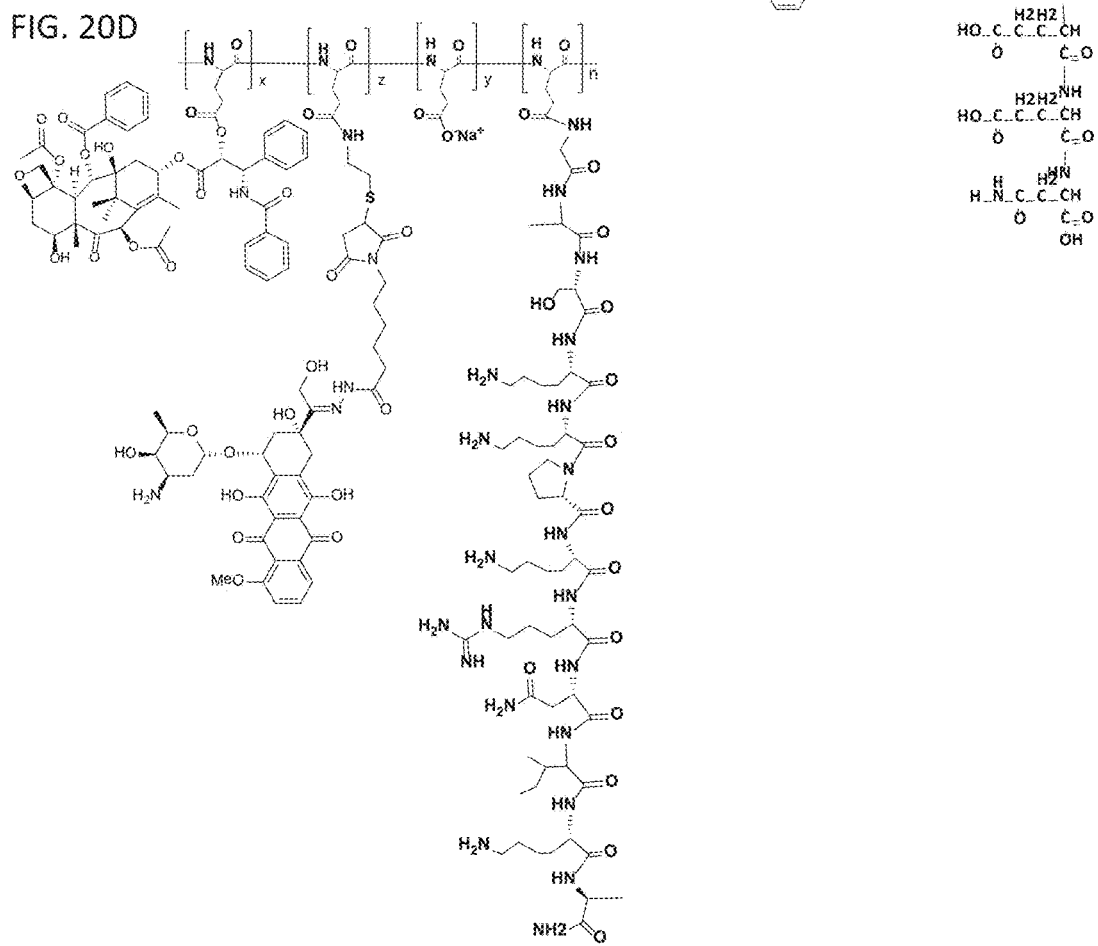

FIGS. 20A-B present the chemical structures of exemplary PGA-PTX-DOX conjugates (prepared by Route 1) having attached thereto an NCAM targeting peptide; NTP (FIG. 20A) and C3 peptide (FIG. 20B). Conjugation of NCAM targeting moieties is similarly performed on PGA-PTX-DOX conjugates prepared by Route 2 as described herein. FIGS. 20C-D present the chemical structures of exemplary PGA-PTX-DOX conjugates (prepared by Route 2) having attached thereto an NCAM targeting peptide; NTP (FIG. 20C) and C3 peptide (FIG. 20D). Other peptide-based targeting moieties (e.g., RGD-containing moieties) can be

Example 5

PGA-PTX-DOX—Activity Assays

Inhibition of the Proliferation of HUVECs:

The effect of the PGA-PTX-DOX conjugate (Route 1, see, FIG. 18) on HUVECs proliferation was tested and compared to the free drugs, each alone and in combination. The obtained data is presented in FIG. 21 and the $IC_{50}$ values are presented in Table 10 below. As can be seen, the PGA-PTX-DOX conjugate inhibited the proliferation of endothelial cells by one degree log less of the combination of the free drugs.

TABLE 10

HUVEC p3

| Treatment | $IC_{50}$ [nM] |
| --- | --- |
| PTX | 1 |
| DOX | 7 |
| PTX + DOX | 0.7 |
| PGA-PTX-DOX | 6 |

Inhibition of Tube Formation of HUVECs:

The effect of the PGA-PTX-DOX conjugate (Route 1, see, FIG. 18) on capillary-like tube formation of HUVECs was tested and compared to that of the free drugs, each alone and in combination, to that of PGA alone and to that of a PGA-PTX conjugate.

The obtained data is presented in FIGS. 22A-B. As can be seen, PGA-PTX-DOX inhibited the tube formation of endothelial cells similarly to the free PTX.

Inhibition of ES-2 Proliferation:

The activity of PGA-PTX-DOX conjugate (Route 1, see, FIG. 18) and of PGA-PTX-DOX conjugate (Route 2, see, FIG. 19D) was examined in vitro on proliferation of ES-2 ovarian carcinoma cells. Cells were incubated with the conjugates PGA-PTX-DOX, PGA-PTX, PGA-DOX and a combination of PGA-PTX and PGA-DOX (in the same ratio as on the PGA-PTX-DOX conjugate), with the free drugs PTX, DOX and their combination (in the same ratio as on the PGA-PTX-DOX conjugate) and with PGA, for 72 hours.

The results are presented in FIG. 23A for PGA-PTX-DOX conjugate (Route 1) and in FIG. 23B for PGA-PTX-DOX conjugate (Route 2).

The $IC_{50}$ values of PGA-PTX-DOX conjugate (Route 2, see, FIG. 19D) are presented in Table 11 below. Results are a summary of three separate experiments. As can be seen, both PGA-PTX-DOX conjugates had a high cytotoxic activity, showing that the drugs are released from the polymer and retain their activity.

TABLE 11

| Treatment | $IC_{50}$ (nM) |
| --- | --- |
| PTX | 6 |
| DOX | 25 |
| PTX + DOX | 5 |
| PGA-PTX-DOX | 40 |
| PGA-PTX | 150 |
| PGA-DOX | 400 |
| PGA-PTX + PGA-DOX | 55 |

Inhibition of Murine 4T1 Proliferation:

The activity of PGA-PTX-DOX conjugate (Route 1, see, FIG. 18) was examined in vitro on proliferation of murine 4T1 mammary carcinoma cells. Cells were incubated with the conjugate PGA-PTX-DOX, with the free drugs PTX, DOX and their combination (in the same ratio as on the PGA-PTX-DOX conjugate) and with PGA, for 72 hours.

The results are presented in FIG. 24. As can be seen, the PGA-PTX-DOX conjugate had a cytotoxic activity, showing that the drugs are released from the polymer and retain their activity.

Inhibition of MDA-MB-231 Proliferation:

The activity of a PGA-PTX-DOX conjugate (Route 2, see, FIG. 19D) was examined in vitro on proliferation of MDA-MB-231 human breast cancer cells. Cells were incubated with the conjugates PGA-PTX-DOX, PGA-PTX, PGA-DOX and combination of PGA-PTX and PGA-DOX (in the same ratio as on the PGA-PTX-DOX conjugate), the free drugs PTX, DOX and their combination (in the same ratio as on the PGA-PTX-DOX conjugate) and with PGA for 72 hours.

The results are presented in FIG. 25. The $IC_{50}$ values are presented in Table 12 below. Results are a summary of three separate experiments. As can be seen, treatment with free PTX and free DOX had an $IC_{50}$ value of 2 and 8 nM, respectively. The combined free drugs (PTX and DOX) exhibited similar activity as the free PTX alone. Expectedly, as PTX- and DOX-equivalent concentrations were used, PGA-PTX and PGA-DOX had a higher $IC_{50}$ value, of 40 and 150 nM, respectively. Combination of PGA-PTX with PGA-DOX, and the final conjugate PGA-PTX-DOX had lower $IC_{50}$ of 15 nM (see, Table 12), showing high cytotoxic activity, and demonstrating that the drugs are released from the polymer and retain their activity.

TABLE 12

| Treatment | $IC_{50}$ (nM) |
| --- | --- |
| PTX | 2 |
| DOX | 8 |
| PTX + DOX | 2 |
| PGA-PTX | 40 |
| PGA-DOX | 150 |
| PGA-PTX + PGA-DOX | 15 |
| PGA-PTX-DOX | 15 |

Inhibition of ES-2 Cells Migration:

The migration of ES-2 cells in the presence of PGA-PTX-DOX conjugate (FIG. 19D) was evaluated using the scratch assay. This method is based on the observation that, upon creation of a new artificial gap, so called "scratch", on a confluent cell monolayer, the cells on the edge of the newly created gap will move toward the opening to close the "scratch" until new cell-cell contacts are established again. A scratch was done on a confluent cell monolayer, and cells were incubated with the conjugates and the free drugs at PTX-equivalent concentrations of 100 nM and DOX-equivalent concentrations of 250 nM for 17 hours. Plates were imaged and width of the gap was measured in the beginning and end of the experiment.

The obtained data is presented in FIG. 26 and demonstrate that PGA-PTX-DOX significantly inhibited the migration of the cells.

Inhibition of MDA-MB-231 Cells Migration:

The migration of MDA-MB-231 cells in the presence of PGA-PTX-DOX (FIG. 19D) conjugate was evaluated using the scratch assay. Following 24 hours incubation of MDA-MB-231 cells in 24 wells plate (800,000 cells per well), the cells were treated with PGA-PTX-DOX, at PTX-equivalent concentrations of 100 nM and DOX-equivalent concentrations of 250 nM and the different controls (conjugates and free drugs at PTX-equivalent concentrations of 100 nM and DOX-equivalent concentrations of 250 nM). Time zero photos were taken by phase-contrast microscope in a reference point. Following another 24 hours of incubation, photos of the reference point were taken again. The samples were analyzed quantitatively by ImageJ software, relative to time zero photos.

The obtained data is presented in FIG. 27 and shows that PGA-PTX-DOX inhibited efficiently the migration of MDA-MB-231 cells by 10% of gap closure.

Cell Internalization into MDA-MB-231 Cells:

Internalization and intracellular release of DOX from the conjugates was evaluated by confocal microscopy (Leica SP5). MDA-MB-231 cells were incubated with free DOX and DOX-containing conjugates (PGA-DOX, PGA-PTX-DOX) at 400 nM equivalent concentrations for 20 minutes, 2, 6 or 24 hours. Following incubation, cells were washed, fixed with 4% PFA and mounted on glass slides using Prolong® Gold antifade reagent with DAPI (4'-6-Diamidino-2-phenylindole) (Invitrogen) for nucleus. DOX was excited at 488 nm and its emission was recorded at 550-700 nm.

The obtained images are presented in FIG. 28. As can be seen, both free DOX and the conjugates are rapidly internalized in the cells. Free DOX is seen to be accumulated in the nucleus following 6 hour incubation, and DOX from the PGA-PTX-DOX conjugate is accumulated in the nucleus following 24 hours of incubation.

In Vivo Studies:

MDA-MB-231 human mammary adenocarcinoma was inoculated orthotopically in mammary fat pad of nu/nu mice.

Mice bearing the mammary cancer cells were treated with the conjugate PGA-PTX-DOX (FIG. 19D), with the conjugates PGA-PTX, PGA-DOX and PGA-PTX+PGA-DOX in the same ratio as in PGA-PTX-DOX conjugate) and with free drugs (PTX, DOX, PTX+DOX in the same ratio as on PGA-PTX-DOX conjugate), according to the following dosing schedule:

Day 11—PTX-equivalent 4.5 mg/Kg, DOX-equivalent 7.5 mg/kg;

Day 14, 16, 18, 22—PTX-equivalent 3 mg/Kg, DOX-equivalent 5 mg/kg.

Tumor volume and body weight change of the mice were monitored. The results are presented in FIGS. 29A-B, and clearly show the minimal growth of tumor volume in mice treated with the PGA-PTX-DOX conjugate, while maintaining body weight within a normal range. Of significance is the substantially superior effect of the conjugate as compared to the free drugs combination treatment (PTX+DOX), and the reduced change in body weight of mice treated with PGA-PTX-DOX compared to PTX+DOX.

Summarizing Remarks:

PGA-PTX-DOX conjugates were successfully synthesized and characterized. In proliferation assays, PGA-PTX-DOX had a high cytotoxic activity, showing that the drugs are released from the polymer and retain their activity.

As expected, free drugs have a lower $IC_{50}$ in vitro, since they rapidly reach the target intracellular site, while conjugated drugs first need to be released from the polymer. This is also confirmed by confocal imaging, as free DOX is seen in the nucleus after 6 hours while DOX from the PGA-PTX-DOX conjugate reached the nucleus only after 24 hours.

The migration of ES-2 cells in the presence of PGA-PTX-DOX conjugate was evaluated using the scratch assay. PGA-PTX-DOX significantly inhibited migration of the cells.

The obtained in vivo data demonstrate the main advantage of the PGA-PTX-DOX conjugate compared with a combination of PTX and DOX and of PGA-PTX and PGA-DOX.

Example 6

Conjugate of PGA Having Attached Thereto NCAM-Targeting Peptide Doxorubicin and/or Paclitaxel Solid Phase Peptide Syntheses (SPPS) of NCAM-Targeting Peptides:

NCAM-targeting peptide (NTP) with the sequence GDDSDEEN (SEQ ID NO:1) and scrambled peptide with the sequence GESDDEND (SEQ ID NO:2) were synthesized using solid phase peptide synthesis (SPPS) method. The sequence DDDSDEEN (SEQ ID NO: 5) is known to bind NCAM and glycine was added as a linker to allow conjugation to PGA and fluorescent labeling. Molecular mass of the products was confirmed by mass spectroscopy to match the calculated mass of peptides, indicating that the correct compound was obtained (data not shown). Purity of the peptides was tested with HPLC. A single peak was obtained, indicating the product is pure (data not shown).

NCAM targeting peptide with the sequence GASKKPKRNIKA (SEQ ID NO:3; C3 peptide) and a control peptide with the sequence GASKKPAANIKA (SEQ ID NO:4; C3ala peptide) were synthesized using solid phase peptide synthesis (SPPS) method on Sieber amide resin. C3 peptide (ASKKPKRNIKA; SEQ ID NO:6) is a known NCAM agonist, which binds to Ig1 domain of NCAM and was also found to bind to FGFR1. Glycine was added at the N-terminal as a linker to allow conjugation to PGA or fluorescent labeling. Molecular mass of the products was confirmed by mass spectroscopy to match the calculated mass of peptides, indicating that the correct compounds were obtained (data not shown). Purity of the peptides was tested with HPLC. A single peak was obtained, indicating the product is pure (data not shown).

Peptides were fluorescently labeled at the N-terminal using 5(6)-carboxyfluorescein (Alfa-Aesar). 5(6)-carboxyfluorescein was activated with HBTU and coupled to the peptide on resin. 5(6)-carboxyfluorescein was used in 5× molar excess, DIPEA was added as a base. The labeled peptide was cleaved from resin as described above. CF labeled peptide was separated from unlabeled peptide by FPLC. The CF-peptide was collected and solution lyophilized to obtain orange-yellow powder. Molecular mass of the products was confirmed by mass spectroscopy to match the calculated mass of peptides, indicating that the correct compound was obtained (data not shown).

The structure of Flourescein-labeled NTP having SEQ ID NO:1 is depicted below.

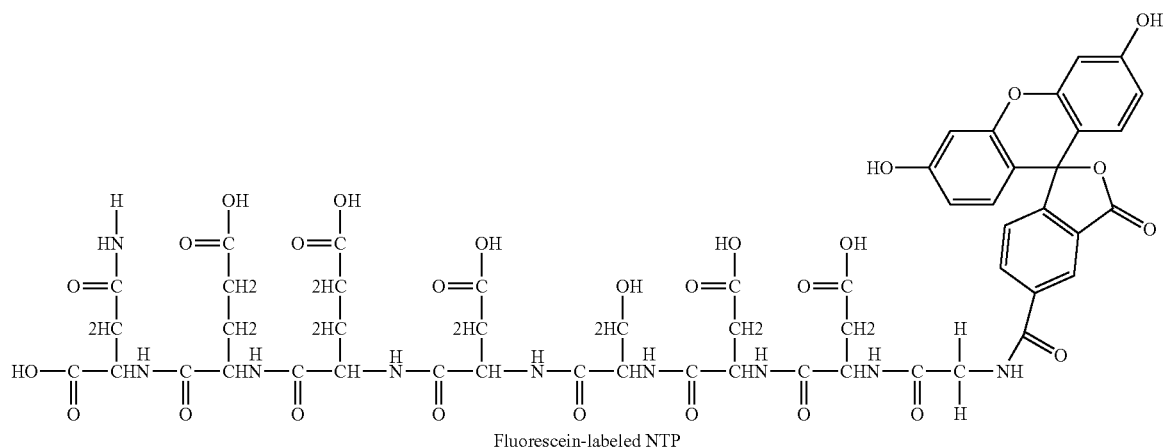

Fluorescein-labeled NTP

Syntheses and Physicochemical Characterization of Conjugates of PGA and NCAM-Targeting Peptide (NTP) and/or PTX:

Synthesis of PGA-NTP:

PGA was synthesized as described hereinabove. NTP (SEQ ID NO:1) was conjugated to PGA by carbodiimide coupling in DMF. Conjugation was done via the N-terminal of the peptide to γ-carboxyl groups on PGA, forming an amide bond. NHS and DIC were added at molar ratio of 1:20, to activate approximately 20% of carboxyl groups on PGA. Reaction was allowed to proceed under N2 for 24 hours. Reaction mixture was poured into CCl4 and acetone was added to precipitate the product. The precipitate was washed with a 4:1 CCl4:acetone mixture. NTP (SEQ ID NO:1) was added to the activated PGA and reaction was allowed to proceed under N2 for 24 hours. The product was precipitated and washed as described above and purified by FPLC with sephadex G75 column. Fractions corresponding to PGA-NTP (retention time of about 30 minutes) and to low MW compounds (retention time of about 90 minutes) were collected. Samples from the latter fraction and from washes of the product were injected in HPLC to test for presence of free peptide. No peak corresponding to NTP was seen in any of the samples, indicating all the NTP is bound to the polymer (data not shown).

FIG. 30 presents the chemical structure of the obtained PGA-NTP conjugate.

Synthesis of PGA-C3-PTX:

A protected from of C3 peptide having SEQ ID NO:3, prepared by SPPS, as described hereinabove, was cleaved from the resin using a "gentle" cleavage process that leaves protecting groups on the side chains of amino groups intact. This was done to achieve selective coupling to the PGA through N-terminal amine of the peptide and not through amines in the peptide sequence (lysines). The protected peptide was conjugated to PGA using carbodiimide coupling in dry DMF, followed by deprotection of the peptide side chains using concentrated TFA, to thereby obtain a PGA-C3 conjugate. Then, PTX was attached to the PGA-C3 as described above for the PGA-PTX conjugate. FIG. 31 presents the chemical structure of the obtained conjugate. PGA-C3ala-PTX control conjugate was synthesized by the same method.

PTX loading was determined by HPLC, by measuring the amount of unbound PTX in the reaction.

Table 13 below presents the physicochemical properties of the obtained conjugate, compared to those of PGA and PGA-PTX.

TABLE 13

| Conjugate | Zeta potential (mV) | PTX loading (% mol) | Molecular weight (theoretical) |
|---|---|---|---|
| PGA-PTX | −30.4 | 7.5% | 21,205 |
| PGA-C3-PTX | −27.3 | 1% | 17,193 |
| PGA | −42.5 | — | 15,100 |

As shown in Table 13, while the zeta potential of PGA is strongly negative since the polymer has multiple carboxyl groups, which are negatively charged, the zeta potential of the peptide-bound polymer is higher, as expected, due to the positively-charged amino groups of the peptide, yet it is still low enough to prevent aggregation in aqueous solution. Based on DLS analysis, it is estimated that the conjugate is 10 nm in size, which is a suitable size for selective distribution by the EPR effect.

NCAM Expression:

In order to select candidates for a model tumor cell line, NCAM expression of various cell lines was evaluated by FACS. The obtained data is presented in Table 14 below. Saos2 cells (>90% expression) were chosen for subsequent experiments as a model for high NCAM expressing tumors. Several cell lines with low to moderate expression were tested further to establish connection between NCAM expression and CSCs in these lines.

TABLE 14

| Cell line | Description | Average NCAM expression (%) |
|---|---|---|
| IMR-32 | Neuroblastoma | 80 |
| U87 | Glioblastoma | 60 |
| Saos2D | Osteosarcoma (dormant) | 91 |
| Saos2E | Osteosarcoma (aggressive) | 91 |
| SK-N-MC | Neuroepithelioma (Ewing) | 12 |
| A549 | Lung carcinoma | 15 |
| HPG2 | Hepatocellular carcinoma | 16 |
| HUH7 | Hepatocellular carcinoma | 18 |
| HCT116 | Colorectal carcinoma | 34 |
| ES2 | Ovarian carcinoma | 18 |
| SKOV | Ovarian carcinoma | 3 |
| OVCAR | Ovarian carcinoma | 92 |

TABLE 14-continued

| Cell line | Description | Average NCAM expression (%) |
|---|---|---|
| MEL-526 | Melanoma | 87 |
| A375 | Melanoma | 28 |
| HUVEC (on plate) | Endothelial cells | 0 |
| HUVEC (on matrigel) | Endothelial cells | 48 |

Sphere Formation Assays:

Ability of different cell lines (SK N MC, A549, HPG2, HUH7, HCT116, ES2) to form spheres after sorting to NCAM+/− was tested. Sphere formation is a known test for presence of cancer stem cells in population. Cells were plated in poly-HEMA coated plates immediately after sorting. It was shown that in ES2 and SK N MC cell lines NCAM+ cells formed significantly more spheres than NCAM− cells, while in various other cell lines there was no difference in sphere formation between NCAM+ and NCAM− cells (data not shown). Therefore, ES2 and SK N MC lines were also chosen for further tests for presence of NCAM expressing CSCs.

Clonogenicity Assays:

Ability of sorted ES2 and SK N MC cells to form single cell colonies was examined. Cells were plated in 96-well plated at a concentration of single cell/well immediately after sorting. In both ES2 and SK N MC lines NCAM+ cells formed significantly more colonies than NCAM− (data not shown).

Proliferation Assays:

Effect of DOX and PTX Treatments on Proliferation of Sorted Cells:

The effect of DOX and PTX treatments on proliferation of ES2 and SK N MC cells after sorting to NCAM+/− and/or on unsorted cells was examined, to test whether NCAM+ cells are more resistant to chemotherapeutic drugs.

$IC_{50}$ values were derived from the growth charts and are presented in Table 15. No significant difference of response between NCAM+ and NCAM− and unsorted cells was seen.

TABLE 15

|  | ES2 | | | SK N MC | | |
|---|---|---|---|---|---|---|
|  | NCAM+ | NCAM− | Unsorted | NCAM+ | NCAM− | Unsorted |
| Doxorubicin | 300 | 150 | 250 | 90 | 40 | 50 |
| Paclitaxel | 70 | 90 | 70 |  |  | 45 |

Binding of NCAM-Targeting Peptides to Cells:

NTP Binding to Saos2 Cells (Confocal Microscopy):

Binding of NTP (SEQ ID NO:1) to Saos-2 cells, compared to binding of sNTP (SEQ ID NO:2), was examined by confocal microscopy. FITC-labeled targeting peptides were used. The obtained images are presented in FIG. 32. As can be seen therein, NTP binds to the cells (see, FIGS. 32B and 32C), while the scrambled peptide does not (see, FIG. 32D). In experiments with transferrin, peptide was seen as intracellular aggregates or vesicles, though not colocalized with transferrin.

C3 Binding to ES2 Cells (FACS):

Binding of C3 (SEQ ID NO:3) to ES2 cells, and competition of binding of the NCAM-specific antibody APC-conjugated anti-human CD56 (NCAM) (BioLegend) and bFGF was examined by FACS. Cells were incubated with antibody, CF-labeled C3 (SEQ ID NO:3 bFGF or combinations of thereof. The observed data is presented in FIG. 33 and show that CF-labeled C3 bound at levels much higher than NCAM expression. When CF-labeled C3 was incubated with the antibody or bFGF, its binding decreased, indicating competition for the binding sites.

Binding of C3 (SEQ ID NO:3) and C3ala (SEQ ID NO:4) to NCAM-expressing Mel-526 human melanoma cells resulted in 50% and 20% binding, respectively (data not shown).

Binding of PGA-C3 to ES-2 Cells:

PGA and PGA-C3 were labeled with FITC on the N-terminal of the PGA chain. Binding to ES-2 cells was examined by FACS. The obtained data is presented in FIG. 34, and show that PGA-C3 bound more strongly than non-targeted PGA and similarly to free C3 peptide.

Proliferation Assays:

Effect of PGA-C3-PTX on Proliferation of ES-2 Cells:

The effect of PGA, free PTX and the conjugates PGA-PTX, PGA-C3, and PGA-PTX-C3 on proliferation of ES-2 cells was evaluated after incubation of the cells with each treatment for 7 minutes, washing the cells and incubation in medium for 72 hours.

Short incubation time was selected since in the usual 72-hour incubation time, both the targeted and non-targeted conjugates would have had sufficient time to internalize into the cells. Under these experiment conditions, only the targeted conjugate remained bound to the cells, while non-targeted polymers or conjugates washed off, resulting in lower efficacy.

The obtained data is presented in FIG. 25 and show that PGA-NTP-PTX inhibited the proliferation of ES-2 cells more than non-targeted PGA-PTX.

Effect of PGA-C3-PTX on Capillary-Like Tubes Formation of HUVECs:

The effect of PGA, free PTX (80 nM), free C3, the conjugate PGA-C3, and the conjugates PGA-PTX and PGA-PTX-C3, at PTX-equivalent concentrations of 80 nM, on capillary-like tube formation of human umbilical vein endothelial cells (HUVEC) was evaluated, in order to confirm that anti-angiogenic properties of PTX are maintained after conjugation. The results are presented in FIG. 36 and show that PGA-C3-PTX and PGA-PTX both inhibited the formation of capillary-like tubes at PTX-equivalent concentrations of 80 nM.

These results indicate that PGA-conjugated PTX retains its anti-angiogenic properties. The advantageous inhibition of tube formation by the targeted conjugate is due to NCAM expression on endothelial cells in the process of capillary-like tube formation.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A polymeric conjugate represented by the Formula:

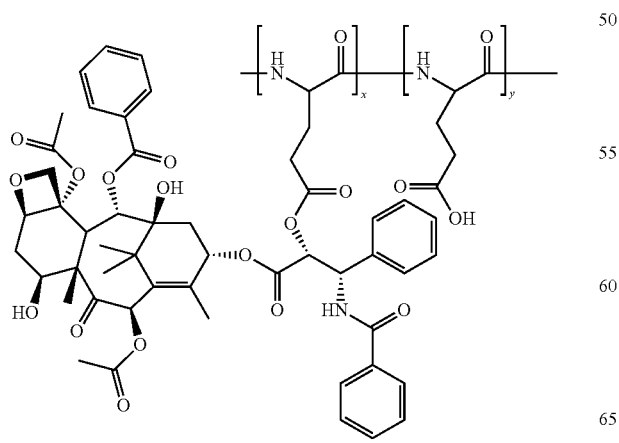

-continued

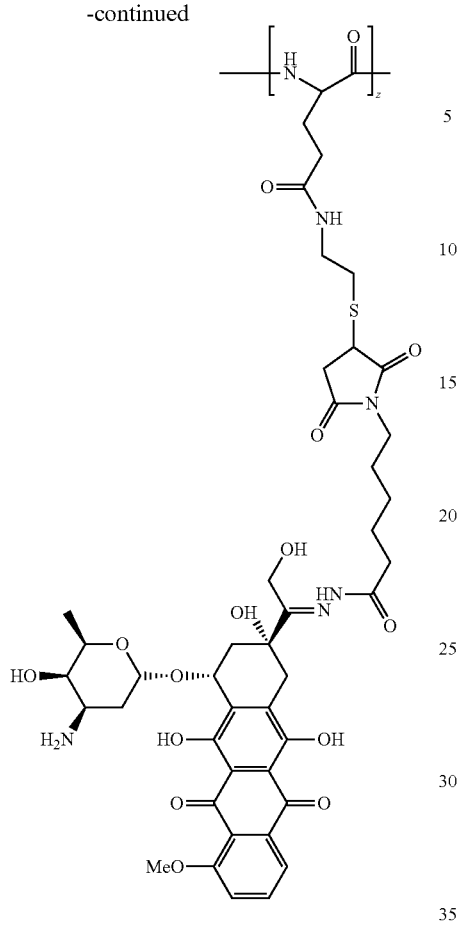

wherein:
y ranges from 50 to 99.9 mol percent;
x ranges from 0.1 to 20 mol percent; and
z ranges from 0.1 to 20 mol percent.

2. The conjugate of claim 1, further comprising a labeling moiety attached thereto.

3. The conjugate of claim 1, wherein x ranges from 1 to 20 mol percent.

4. The conjugate of claim 1, wherein z ranges from 1 to 20 mol percent.

5. A pharmaceutical composition comprising the conjugate of claim 1 and a pharmaceutically acceptable carrier.

* * * * *